US011633353B2

(12) United States Patent
Eriksson et al.

(10) Patent No.: US 11,633,353 B2
(45) Date of Patent: Apr. 25, 2023

(54) LEVODOPA INFUSION SOLUTION

(71) Applicant: DIZLIN PHARMACEUTICALS AB, Gothenburg (SE)

(72) Inventors: Elias Eriksson, Gothenburg (SE); Nil Dizdar Segrell, Linköping (SE); Mats Ehrnebo, Uppsala (SE); Leif Bring, Vimmerby (SE)

(73) Assignee: DIZLIN PHARMACEUTICALS AB, Gothenburg (SE)

( * ) Notice: Subject to any disclaimer, the term of this patent is extended or adjusted under 35 U.S.C. 154(b) by 211 days.

(21) Appl. No.: 16/619,176

(22) PCT Filed: Jun. 5, 2018

(86) PCT No.: PCT/EP2018/064774
§ 371 (c)(1),
(2) Date: Dec. 4, 2019

(87) PCT Pub. No.: WO2018/224501
PCT Pub. Date: Dec. 13, 2018

(65) Prior Publication Data
US 2020/0146986 A1    May 14, 2020
US 2021/0212945 A2    Jul. 15, 2021
US 2021/0378954 A9    Dec. 9, 2021

(30) Foreign Application Priority Data

Jun. 5, 2017  (SE) .................................... 1750707-0

(51) Int. Cl.
A61K 9/08        (2006.01)
A61K 31/198      (2006.01)
A61K 47/12       (2006.01)
A61K 9/00        (2006.01)
A61K 47/18       (2017.01)
A61K 45/06       (2006.01)
A61P 25/16       (2006.01)
A61K 47/02       (2006.01)
A61K 47/26       (2006.01)
A61P 25/00       (2006.01)
A61K 47/40       (2006.01)

(52) U.S. Cl.
CPC .............. *A61K 9/08* (2013.01); *A61K 9/0019* (2013.01); *A61K 31/198* (2013.01); *A61K 47/02* (2013.01); *A61K 47/12* (2013.01); *A61K 47/18* (2013.01); *A61K 47/26* (2013.01); *A61K 47/40* (2013.01); *A61P 25/00* (2018.01); *A61P 25/16* (2018.01); *A61K 45/06* (2013.01)

(58) Field of Classification Search
CPC ...... A61K 9/08; A61K 9/0019; A61K 31/198; A61K 47/02; A61K 47/12; A61K 47/18; A61K 47/26; A61K 47/40; A61K 45/06; A61P 25/00; A61P 25/16

USPC ......................................................... 514/567
See application file for complete search history.

(56) References Cited

U.S. PATENT DOCUMENTS

| 6,540,715 B1 | 4/2003 | Kühn et al. |
| 8,815,950 B2 | 8/2014 | Remenar et al. |
| 2005/0070608 A1 | 3/2005 | Remenar et al. |
| 2005/0203185 A1 | 9/2005 | Remenar et al. |
| 2011/0294889 A1 | 12/2011 | Segrell |
| 2015/0065993 A1 | 3/2015 | Arocha |
| 2021/0077442 A1 | 3/2021 | Yacoby-Zeevi et al. |

FOREIGN PATENT DOCUMENTS

| AU | 2011101361 A4 | 12/2011 |
| CN | 1845728 A | 10/2006 |
| CN | 101022784 A | 8/2007 |
| CN | 102755252 A | 10/2012 |
| JP | 54105221 A | 8/1979 |
| JP | 2007-504143 A | 3/2007 |
| JP | 2012-527447 A | 11/2012 |
| SE | 512655 C2 | 4/2000 |
| WO | 2006/006929 A1 | 1/2006 |
| WO | 2012/066538 A1 | 5/2012 |

OTHER PUBLICATIONS

Yang, Zongfa, Pharmaceutical Formulation Devices, Military Medical Publishers, p. 189-190 (Aug. 2014), please see p. 10 of corresponding Chinese Office Action.
Official Office Action from corresponding Chinese Application No. 201880037143.6 dated Sep. 3, 2021 with English Translation.
Search Report from corresponding Chinese Application No. 201880037143.6 dated Aug. 30, 2021.
Chaná, Pedro et al., Clinical/Scientific Notes, Gabapentin and Motor Fluctuations in Parkinson's Disease, Movement Disorders, vol. 12, No. 4, pp. 608-623 (1997).
Shoulson, M.D., Ira et al., On-Off response, Clinical and biochemical correlations during oral and intravenous evodopa administration in parkinsonian patients, Neurology, vol. 25, pp. 1144-1148 (1975).

(Continued)

*Primary Examiner* — Kristin A Vajda
(74) *Attorney, Agent, or Firm* — Porter Wright Morris & Arthur LLP

(57) ABSTRACT

The invention provides an aqueous pharmaceutical solution for use in the treatment of diseases of the central nervous system (CNS), the solution comprising at least 5 mg/ml dissolved levodopa, and having a pH in the range of 3.0 to 8.5. Said solution is provided by mixing a) an aqueous stock solution comprising levodopa, said stock solution having a pH of less than 2.8 at 25° C. and b) an aqueous buffering solution, for increasing the pH of said stock solution, said buffering solution having a pH of at least 4.0 at 25° C. The aqueous pharmaceutical solution is administered to a subject suffering from a disease of the central nervous system (CNS) shortly after mixing of the aqueous stock solution and the aqueous buffering solution. Furthermore, the invention provides a kit for administration of aqueous pharmaceutical solutions to subjects suffering from diseases of the central nervous system (CNS).

85 Claims, 13 Drawing Sheets

(56) References Cited

OTHER PUBLICATIONS

Buxton, Lain L. O. et al., Pharmacokinetics: The dynamics of drug absorption, distribution, metabolism and elimination, Goodman & Gilman's the Pharmacological Basis of Therapeutics, pp. 17-40 (2011).

Lambers, H. et al., Natural skin surface pH is on average below 5, which is beneficial for its resident flora, International Journal of Cosmetic Science, vol. 28, pp. 359-370 (2006).

Lewis, III, James L., Metabolic Alkalosis, Merck Manuals Professional Version, pp. 1-5 (Mar. 2018).

LEVODOPA INFUSION SOLUTION

FIELD OF THE INVENTION

The present invention relates to a pharmaceutical product for treatment of diseases of the central nervous system consisting of a levodopa solution suitable for continuous parenteral or enteral administration and an administration system suitable for administering the said solution.

BACKGROUND OF THE INVENTION

Dopamine [3,4-dihydroxyphenylethylamine] is an organic substance of the catecholamine and phenethylamine families that plays several important roles in the brain and body. In the brain, dopamine functions as a neurotransmitter released by neurons (nerve cells). The brain includes several distinct dopamine pathways and dopamine is vital to several of the functions of the central nervous system such as movement, attention, mood and motivation. Several diseases of the nervous system, e.g. Parkinson's disease, are associated with dysfunctions of the dopamine system and some of the key medications used are modulating the levels of dopamine in the brain.

Parkinson's disease (PD) is very common and is contracted by approximately 15 out of 10,000 people in the Western world. The age of debut is usually between 55 and 60 years. The disease is characterized by rigidity, tremor and bradykinesia (poverty of motion) caused by a massive loss of nigrostriatal neurons and subsequently a lack of dopamine. Later, during the course of the disease, cognitive and behavioural problems may arise. The symptoms of Parkinson's disease appear upon a loss of approximately 80% of dopamine neurons.

Nobel laureate Arvid Carlsson discovered in the late 1950s that the natural amino acid levodopa (L-dopa) is converted to dopamine when it reaches the brain. Levodopa is still—ever since—"the golden standard" for the treatment of PD. Levodopa treatment of patients suffering from PD improves the patient's ability to function in the society and their quality of life and reduces both individual and societal costs. Levodopa is the precursor to the neurotransmitters dopamine, norepinephrine and epinephrine. In spite of the massive loss of dopamine neurons in early stages of the disease, an adequate storage capacity is still maintained enabling an even release of dopamine into the synaptic cleft at oral intake of levodopa tablets.

Unfortunately, pharmacokinetic and pharmacodynamic problems (on-off symptoms) develop after several years of oral treatment with levodopa. The on-off symptoms arise after approximately five years of oral treatment in the form of motor fluctuations—ranging from disabling dyskinesia (involuntary movements) to akinesia (total lack of mobility). On-off symptoms worsen during the course of the disease. Researchers believe that on-off symptoms most likely are caused by the way in which levodopa is administered. More specifically, it is believed that the intermittent administration of levodopa through oral treatment, together with the degeneration of dopaminergic neurons, are the main causes of the development of on-off symptoms. Intermittent oral treatment eventually leads to a narrower therapeutic window for levodopa making oral administration even more problematic. It is a shared view that a more continuous administration of levodopa would be beneficial to the PD patients.

Shoulson et.al. showed already in 1979 that continuous administration of levodopa had a beneficial effect on on-off symptoms. Parenteral administration would be a preferred way of obtaining continuous administration. The problem is that it has not been possible to produce a physiologically acceptable infusion solution of a high enough levodopa concentration—which in turn provides a sufficiently small volume—making it suitable for continuous parenteral administration. In the experiments conducted by Shoulson et.al., patients were given several litres per day. The heart cannot handle such large infusion volumes for any extended period of time.

Numerous attempts have been made over a 30-year period to increase the levodopa concentration in a physiologically acceptable infusion solution, but without decisive success. The researchers have been facing a major problem in that levodopa precipitates at concentrations greater than in the range of 0.5-1.0 mg/ml at pH values acceptable—or at least desirable—at continuous parenteral administration. A levodopa concentration in the range of 0.5 to 1.0 mg/ml would result in volumes of 1-2 litres per day for patients in the late stages of PD, which normally requires about 1 000 mg oral levodopa per day. Such volumes cannot be continuously administered parenterally for long periods.

An infusion solution where an API (Active Pharmaceutical Ingredient) precipitates is not acceptable in a pharmaceutical product. An infusion solution for parenteral administration must be completely clean and free of particles.

The levodopa molecule is generally stable and readily soluble both at very low pH-values (typically pH<3) and at very high pH-values (typically pH>9) and levodopa concentrations exceeding 5 mg/ml may be obtained in these pH-ranges. Consequently, stable levodopa solutions with low pH-values are known from the art (e.g. the stock solutions presented in patent SE 512 655), as well as levodopa solutions with very high pH-values as presented in JP54105221 and WO 2012/066538 A1, which both present levodopa solutions with pH>9).

An infusion solution having a pH of <3 is not suitable for continuous parenteral administration but would result in severe adverse systemic acidosis and adverse skin effects (noduli). An infusion solution having a pH>9 is also connected with adverse skin effects such as severe noduli. In addition, an infusion solution with a pH>9, when infused parenterally, may cause adverse systemic effects such as Cardiac Arrhythmia (irregular heartbeats). Moreover, an infusion solution intended for subcutaneous infusion with a pH>9—which is required for an infusion solution in order to be long term stable at a concentration of, or above, 10 mg/ml—is distributed very poorly in the subcutaneous tissue, which in turn prevents e.g. PD be treated in an effective manner.

A levodopa infusion solution for continuous parenteral use should further preferably contain an inhibitor that reduces the metabolization of levodopa in the systemic circulation. Carbidopa is such an inhibitor that is frequently used at oral levodopa treatments. The volume of an infusion solution containing an inhibitor, such as carbidopa, may be reduced by 30-50% and still have the same clinical effect as a corresponding levodopa solution without carbidopa.

An infusion solution containing the APIs levodopa and an inhibitor, such as carbidopa, needs to fulfil several stringent conditions enabling it to be registered as a pharmaceutical product and thus becoming available to the patients suffering from PD. The degradation of the API:s—from the point of time the pharmaceutical product is produced up to the time it is administered to the patient—must stay within given limits. Often the degradation of the concentration of each API must be lower than 10% of its original value. Furthermore, the content of any toxic metabolite must stay within certain stipulated limits. It is thus demanding to successfully formulate an API typically being degraded in aqueous solution at physiological pH for infusion applications.

Any adverse effect must not violate what may be justified considering the advantage for the patient being treated with the pharmaceutical product concerned.

The prior art has failed to provide a solution containing levodopa and carbidopa suitable for continuous subcutaneous infusion, with sufficient uptake in the plasma enabling the treatment of PD-patients on an individual basis for maximal reduction of on-off symptoms, which fulfils the requirements for being approved as a pharmaceutical product.

Thus, there is great need for a pharmaceutical product containing levodopa and carbidopa suitable for continuous subcutaneous infusion, with sufficient subcutaneous absorption enabling the treatment of PD-patients on an individual basis for maximal reduction of on-off symptom, which at the same time cause minimal adverse effects. Moreover, there is a need for such a pharmaceutical product having a long shelf life—preferably up to one year or more.

In the late 1970s, the Japanese patent JP 54105221 introduced a method for preparing physically stable levodopa solutions, with levodopa concentrations up to 15 mg/ml, intended for injection. According to the description, the solutions were stable at a very high pH, which can also be expected given the chemical properties of levodopa (see further below). The highly basic (pH about 9) injection solutions presented allowed a levodopa concentration of up to 15 mg/ml. To achieve the concentration of 15 mg/ml, the injection solution was mixed with a gel. Injection solutions mixed in a gel are not intended for parenteral administration but may be advantageously used for oral or enteral injection. A solution for parenteral administration must be free of particles and must not be a suspension (cannot contain a gel). The presented injection solutions were all very basic. The disadvantages of very basic infusion solutions have been stated previously in the description.

In the early 1990s, a levodopa solution for continuous enteral administration was presented. A levodopa concentration of about 20 mg/ml was achieved by allowing the solution to take the form of a suspension, which however does not allow the solution to be used for parenteral administration. The solution, Duodopa, also contained carbidopa for reducing the metabolism of levodopa on its way from the intestine through the bloodstream to the brain. The use of inhibitors is well known and such are used in most cases of clinical use of levodopa. Duodopa have major disadvantages in that the use requires a surgical procedure at the start of treatment. Continuous administration via the duodenum means that a probe must be applied, which enters through the abdominal wall, and troublesome side effects are common. Inflammations frequently occur in and around the stoma in the abdominal wall. The probe sometimes moves, and if it gets misaligned, a new surgical intervention is required. The high viscosity of the gel-based suspension requires a powerful pump for the gel to be pressed through the probe, and the administration system thus becomes heavy and unwieldy. The limited durability constitutes a further disadvantage. The shelf life of unopened packages does not exceed three months, which means logistical disadvantages and a more expensive product.

In the early 2000s, a breakthrough was made when it comes to the development of levodopa infusion solutions for parenteral administration (patent SE 512 655). The patent discloses a levodopa solution for parenteral administration with a levodopa concentration of about 5 mg/ml in the pH range of 4-6. The patent does not teach how to include any inhibitor such as carbidopa. The presented infusion solution may be useful for intravenous infusion but a concentration of 5 mg/ml without inhibitors results in volumes which are too high for clinical treatment of on-off symptoms by continuous subcutaneous infusion. According to the patent, the infusion solution was physically stable up to 3 days. A shelf life not exceeding 3 days limits the practical use of the infusion solution.

Patent application PCT/SE2005/001135 describes an infusion solution for continuous parenteral administration of levodopa at a concentration of 10 mg/ml or more at a pH lower than or equal to 6. One objective of the invention according to PCT/SE2005/001135, is to avoid precipitation of levodopa. The described solution optionally also contains an inhibitor such as carbidopa. An inhibitor like carbidopa reduces the metabolism of levodopa in the systemic circulation resulting in an increased amount of levodopa reaching the brain. In turn, it allows the volume of such an infusion solution be reduced by up to 50% compared to an infusion solution lacking an inhibitor. An example is described in the application where a levodopa solution of 10 mg/ml containing 1 mg/ml carbidopa was physically stable for at least 3 days at a pH in the range of 3.5 to 4.0. It is unclear if the said solution may be physically stable for more than three days. An infusion solution with short physical stability entails serious logistical problems, which in reality may result in a product, which is not practical for use as a medical drug. Neither is there any information to be found about the chemical stability of the APIs nor the amount of any toxic metabolites. The description does not contain enough information about the properties of the solutions making it possible to determine whether or not the solution could be classified as a pharmaceutical product fulfilling regulatory requirements.

Patent application WO 2012/066538 A1 describes an infusion solution containing at least 4 weight percent (at least about 40 mg/ml) levodopa including the inhibitor carbidopa having a pH in the range of 9.1 to 9.8 at 25° C. The infusion product described in the said patent has an even higher pH-value than the earlier product described in Japanese patent JP 54105221. It follows from the chemical properties of levodopa and carbidopa that these components have a good chemical stability at very high (and very low) pH values, which also explains the results obtained in the experiments with levodopa at high pH values described in the Japanese patent JP 54105221. However, there are several problems associated with solutions having such high pH-values, in particular at parenteral administration.

Infusion solutions and injectable solutions with high pH-values (above 8-9) show decreased subcutaneous absorption. The latter is confirmed in clinical studies conducted on the product ND0062, a product based on patent application WO 2012/066538 A1, where a levodopa concentration of about 1,200 ng/ml in the plasma was reached first after about 6 hours of continuous subcutaneous infusion, and the maximum value of about 1,300 ng/ml was not reached until 8 hours of continuous infusion. It is not clear whether therapeutic levels are at all reached for PD-patients in late phases of the disease. Consequently, oral intake of an inhibitor, or levodopa combined with an inhibitor, is recommended as an add-on when PD-patients in late phases of the disease are treated with the infusion solution described in the said patent application. As a comparison, the levodopa concentration in the plasma, required for obtaining therapeutic effect, was 1,600 ng/ml on average for PD-patients in late phases participating in a clinical study on Duodopa.

Other disadvantages of infusion solutions having very high pH-values have been stated previously in the description.

It has never previously, prior to the invention, been taught in the art about a product, containing levodopa and at least one inhibitor, suitable for continuous parenteral or enteral administration (and especially continuous subcutaneous infusion), having a pH-value in the range of 3.0-8.5 (resulting in minimal adverse skin effects and low, if any, systemic adverse effects like Cardiac Arrhythmia and high subcutaneous absorption), which fulfils the stringent rules put up by medical authorities (the degradation of the APIs and the level of toxic by-products staying within stipulated limits) enabling it to be approved as a pharmaceutical product. Consequently, no infusion solution for parenteral administration previously presented in the art has managed to obtain a registration as a pharmaceutical product. This is in spite of the fact that there is a great need for such a product. Hence, there is a great need for the invention.

SUMMARY OF THE INVENTION

Accordingly, the present invention preferably seeks to mitigate, alleviate or eliminate one or more of the above-identified deficiencies and disadvantages of the products described in the art, singly or in any combination, and solves the above-mentioned problems by providing formulations of stock- and buffering solutions which allow for instant mixing of the solutions, providing a pharmaceutically acceptable infusion solution, to be administered shortly after the mixing. In some embodiments, the formulations allow for an "on line" mixing approach according to the invention, where the specified stock and buffering solutions are continuously mixed and the resulting infusion solution is continuously transported from the place of mixing to the infusion site where the pharmaceutical infusion solution is continuously administered to a patient via a parenteral or enteral route for up to 24 hours. This is especially favourable for administration through continuous subcutaneous infusion, where the on-line mixing enables the pharmaceutical infusion solution to have a pH in the range of 4.5-6.5, where the infusion solution has reduced stability but where the subcutaneous distribution (the uptake of the APIs in the blood) is optimal. Furthermore, the on-line mixing, and the corresponding low degradation of the APIs, results in a very low content of toxic by-products such as hydrazine in the infusion solution, which contributes to its approval as a pharmaceutical product. Since the inherent properties of the solutions of the invention allow for on line mixing followed by on line administration, any degradation of APIs will be well within allowable limits of pharmaceutical regulations (such as below 15% degradation of the original concentration of the APIs). This also allows for administration of solutions that are at risk of precipitating, such as supersaturated or metastable solutions. As such, according to a first aspect of the invention, there is provided an aqueous pharmaceutical solution for use in the treatment of diseases of the central nervous system (CNS), the solution comprising; at least 5 mg/ml dissolved levodopa, and having a pH in the range of 3.0 to 8.5, wherein said solution is provided by mixing; a) an aqueous stock solution comprising levodopa, said stock solution having a pH of less than 2.8 at 25° C.; and b) an aqueous buffering solution, for increasing the pH of said stock solution, comprising at least one buffer component and said buffering solution having a pH of at least 4.0 at 25° C., wherein the aqueous pharmaceutical solution is administered to a subject suffering from a disease of the central nervous system (CNS) within 24 hours, such as within 16 hours, 12 hours, 6 hours, 4 hours, 2 hours, 1 hour, 30 minutes, 20 minutes, 10 minutes, 5 minutes or 1 minute, from mixing the aqueous stock solution and the aqueous buffering solution.

Also, an aqueous pharmaceutical solution for use in the treatment of diseases of the central nervous system (CNS) is provided, the solution comprising at least 5 mg/ml dissolved levodopa and having a pH in the range of 3.0 to 8.5, wherein said aqueous pharmaceutical infusion or injection solution is supersaturated with levodopa.

The stability of levodopa decreases with increasing concentration. Therefore, more dilute formulations may be physically stable for longer periods of time. In some embodiments, the pharmaceutical solution comprises at most 10 mg/ml levodopa, and is administered within 24 hours of the stock solution and the buffering solution being mixed. These embodiments may be formulated for injection or infusion.

In further embodiments, the concentration of levodopa may be increased to the point of oversaturation. At levodopa concentrations higher than 10 mg/mL, precipitation of levodopa is observed more rapidly and, at very high concentrations, precipitation may be observed within 20 min. Due to the lower physical stability of oversaturated solutions, on line mixing may be used to rapidly administer the solution to a patient before the solution precipitates or degrades. The use of on line mixing allows for continuous mixing of an aqueous stock solution and an aqueous buffering solution, followed by continuous administration of the resulting aqueous pharmaceutical solution, where the infusion solution is transported from the mixing point to the infusion site, typically via plastic tubes, and administered to the patient, such as within two hours. In the event (for a specific formulation) the time period, when the degradation of an API reaches an acceptable limit, is shorter than two hours then the transport time from mixing till infusion may be reduced. In some embodiments, the aqueous pharmaceutical solution is thus administered within 1.5 hours, 1 hour, 50 minutes, 40 minutes, 30 minutes, 20 minutes, 10 minutes, 5 minutes or 1 minute, from mixing the aqueous stock solution and the aqueous buffering solution.

Further, according to one embodiment, the aqueous stock solution comprises at least one physiologically acceptable acid. The aqueous stock solution may further comprise at least one stabilizer. Also, according to some embodiment, the aqueous pharmaceutical solution further comprises at least one enzyme inhibitor. The aqueous buffering solution may further comprise at least one stabilizer. The aqueous buffering solution may further comprise at least one solubilizer.

According to a preferred embodiment of the invention, an aqueous pharmaceutical solution is provided, wherein the solution is provided by mixing:
I) An aqueous stock solution, having of pH of less than 2.8 at 25° C. containing;
   a) aqua sterile,
   b) levodopa,
   c) at least one enzyme inhibitor,
   d) at least one physiologically acceptable acid,
   e) at least one stabilizer,
wherein the stock solution is bubbled with nitrogen after mixing, and
II) An aqueous buffering solution, having a pH of at least 4.0 at 25° C., containing;
   f) aqua sterile,
   g) at least one buffer component,
   h) at least one stabilizer and/or solubilizer, wherein the aqueous pharmaceutical solution may be oversaturated and is administered to a subject suffering from a disease of the central nervous system (CNS) within 24 hours, such as within 16 hours, 12 hours, 6 hours, 4 hours, 2 hours, 1 hour, 30 minutes, 20 minutes, 10 minutes, 5 minutes or 1 minute, from mixing the aqueous stock solution and the aqueous buffering solution.

Furthermore, according to another aspect of the invention, a kit for providing an aqueous pharmaceutical solution, for use in the treatment of diseases of the central nervous system (CNS) is provided, the solution comprising at least 5 mg/ml dissolved levodopa, and having a pH in the range of 3.0 to 8.5, said kit comprising; a) an aqueous stock solution comprising levodopa according to any one of the preceding claims, said stock solution having a pH of less than 2.8 at 25° C., b) an aqueous buffering solution according to any one of the preceding claims, for increasing the pH of said stock solution, comprising a buffer and having a pH of at least 4.0 at 25° C.; c) mixing means (1) for mixing said solutions a) and b); and d) an output means (2) for said mixed solution of step c).

Also, a set for providing an aqueous pharmaceutical solution is provided, comprising: I) An aqueous stock solution, having of pH of less than 2.8 at 25° C. comprising; a) aqua sterile, b) levodopa, c) at least one enzyme inhibitor, d) at least one physiologically acceptable acid, and e) at least one a stabilizer, and II) An aqueous buffering solution, having a pH of at least 4.0 at 25° C., comprising; f) aqua sterile, g) at least one buffer component, and h) at least one stabilizer and/or solubilizer.

According to another aspect of the invention, there is provided a method of continuously preparing the previously described aqueous pharmaceutical solution. The method includes the step of continuously mixing a flow of the previously described stock solution and a flow of the previously described buffering solution. This may comprise using the previously described kit.

According to another aspect of the invention there is provided a method of continuously preparing an aqueous pharmaceutical solution for use in the treatment of diseases of the central nervous system (CNS), the aqueous pharmaceutical solution being suitable for continuous parenteral or enteral administration, wherein the method comprises: continuously mixing a flow of a stock solution comprising levodopa, said stock solution having a pH of less than 2.8 at 25° C. and a flow of an aqueous buffering solution, said buffering solution having a pH of at least 4.0 at 25° C.; and continuously obtaining from said mixing a continuous flow of an aqueous pharmaceutical solution comprising at least 5 mg/ml dissolved levodopa, such as at least 6, 7, 8, 9, 10, 15, or 20 mg/ml dissolved levodopa; preferably the concentration of levodopa being in the range of 5 to 20 mg/ml dissolved levodopa, such as in the range 5 to 15 mg/ml or 5 to 10 mg/ml dissolved levodopa.

According to another aspect of the invention there is provided a method of treating diseases of the central nervous system (CNS) comprising: continuously mixing a flow of an aqueous stock solution comprising levodopa, said aqueous stock solution having a pH of less than 2.8 at 25° C. and a flow of an aqueous buffering solution, said aqueous buffering solution having a pH of at least 4.0 at 25° C.; continuously obtaining from said mixing a continuous flow of an aqueous pharmaceutical solution comprising at least 5 mg/ml dissolved levodopa, such as at least 6, 7, 8, 9, 10, 15, or 20 mg/ml dissolved levodopa; preferably the concentration of levodopa being in the range of 5 to 20 mg/ml dissolved levodopa, such as in the range 5 to 15 mg/ml or 5 to 10 mg/ml dissolved levodopa; and continuously administering to a subject suffering from a disease of the central nervous system (CNS) the obtained aqueous pharmaceutical solution.

According to another aspect of the invention there is provided, an aqueous pharmaceutical solution containing one or more Active Pharmaceutical Ingredients (APIs) for use in the treatment of diseases of the central nervous system (CNS), the aqueous pharmaceutical solution comprising;

a1. at least 5 mg/ml of the API levodopa or a2. at least 5 mg/ml of the API levodopa and at least 0.25 mg/ml of at least one of the APIs belonging to the group of inhibitors, e.g. Carbidopa, having a pH in the range of 3.0 to 8.5, wherein the aqueous pharmaceutical solution is provided by mixing;

a) an aqueous stock solution comprising one or more APIs, the aqueous stock solution having a pH less than 2.8 at 25° C.; and b) an aqueous buffering solution, for adjusting the pH of said stock solution, comprising at least one buffer component, said buffering solution having a pH of at least 4 at 25° C., where the aqueous pharmaceutical solution is administered to a subject suffering from a CNS-disease and where the administration is commenced and on-going as long as the degradation of the concentration of any API does not exceed 15% of its concentration prior to mixing.

With this method any of the previously mentioned CNS diseases can be treated by any previously mentioned route of administration.

Further advantageous features of the invention are elaborated in embodiments disclosed herein. In addition, advantageous features of the invention are defined in the dependent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DETAILED DESCRIPTION

The following description focuses on an embodiment of the present invention applicable to a product intended for the treatment of diseases of the Central Nervous System (CNS) comprising a levodopa infusion or injection solution suitable for continuous parenteral administration and an administration system suitable for administering the infusion or injection solution to patients suffering from a CNS disease.

It has hitherto never been described how to produce a solution containing levodopa of a concentration high enough to allow for continuous parenteral administration and having a pH in the range of 3.0-8.5, which satisfies the product requirements for being registered as a pharmaceutical. Similarly, an injection solution for enteral administration having said advantages of the invention over existing products has never been shown.

Application PCT/SE2005/001135 describes how to obtain a physiologically acceptable infusion solution containing levodopa with a concentration of at least 10 mg/ml, which is physically stable (no precipitation) for more than 3 days and has a pH value that is lower than or equal to 6. The examples in application are however limited to solutions having a pH below 4. However, as shown in the instant application, this product is not sufficiently chemically stable (the degradation of both levodopa and carbidopa is too rapid to allow for approval as a pharmaceutical). The chemical decomposition also creates toxic degradation products, which prevent the product from being classified as a pharmaceutical product, that is, it would not be approved as a pharmaceutical. To address this previously unknown problem relating to chemical instability, the present invention presents a pharmaceutically viable product for which the degradation of the APIs is well within stipulated limits as well as methods for making and administering such products. In addition, the content of any toxic by-products of the invention is within stipulated limits. Furthermore, the aqueous stock solution and the aqueous buffering solution, which are mixed to produce the aqueous pharmaceutical solution of the invention, have a shelf life of at least one year, which means clear logistic advantages. The products and methods of the present invention also make continuous administration possible. Such continuous administration provides the advantage of adjusting the dose of levodopa administered to each patient to achieve a therapeutic level and minimize the on-off effects.

Figure 1:
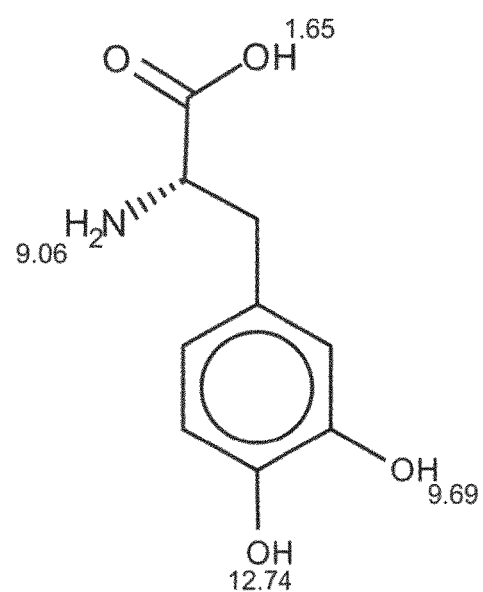
FIG. 1 is a structural representation of levodopa with calculated pKa-values indicated at each centre of the molecule.
Figure 2:
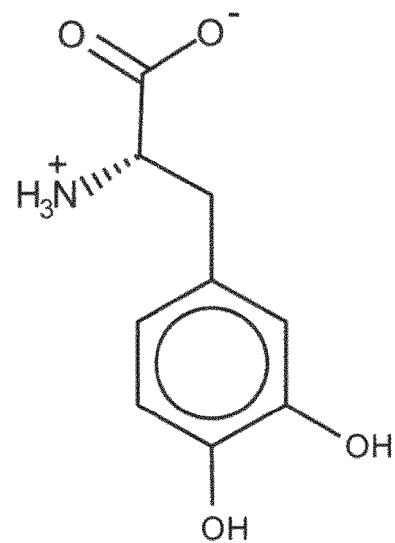
FIG. 2 is a structural representation of levodopa with the structure that will dominate at a pH in the range 4 to 7.
Figure 5A:
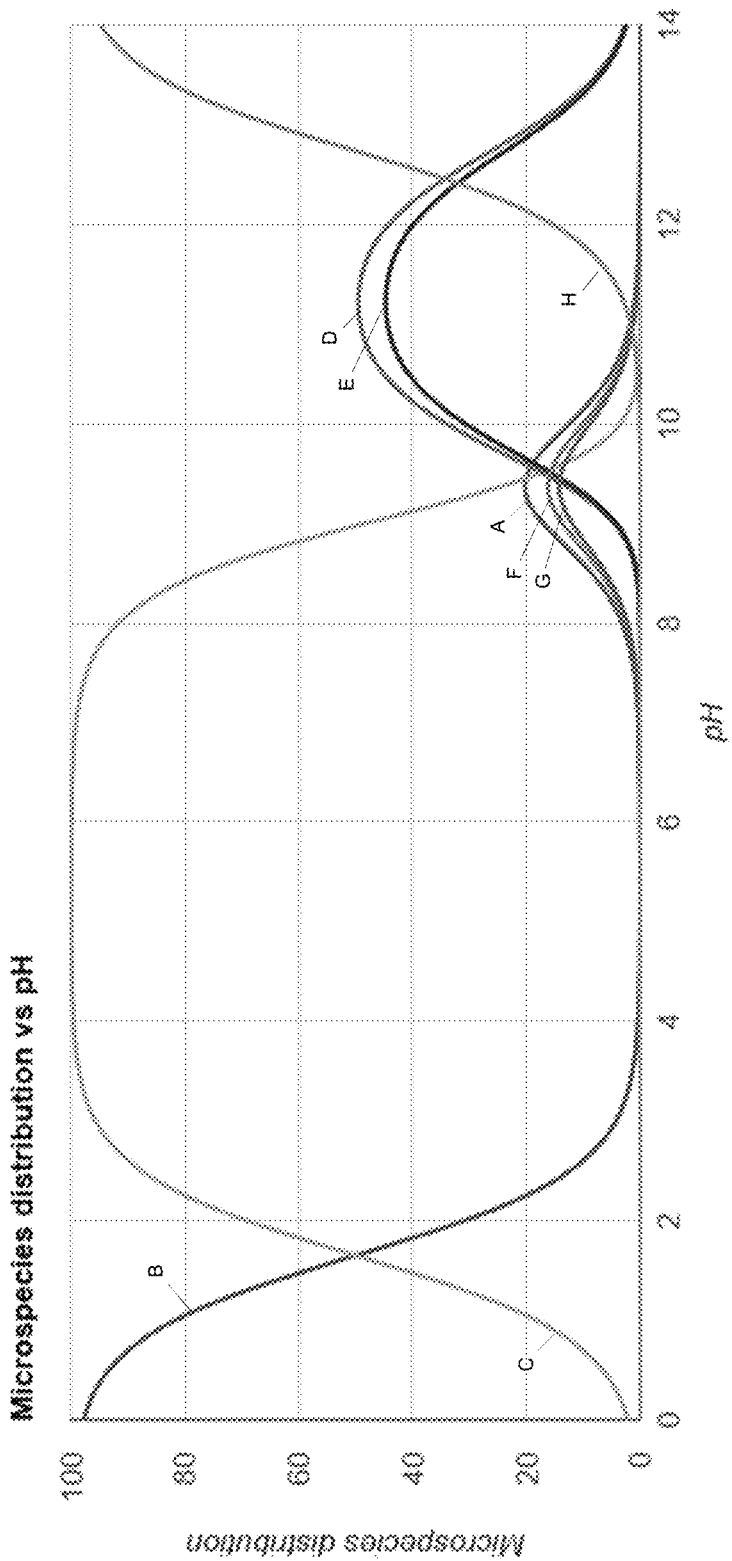
FIGS. 5A and 5B show a calculated micro-species distribution of levodopa vs. pH, where the y-axis denotes the molar percentage of each molecular form in relation to the total amount, and the x-axis is the pH.
Figure 5B:
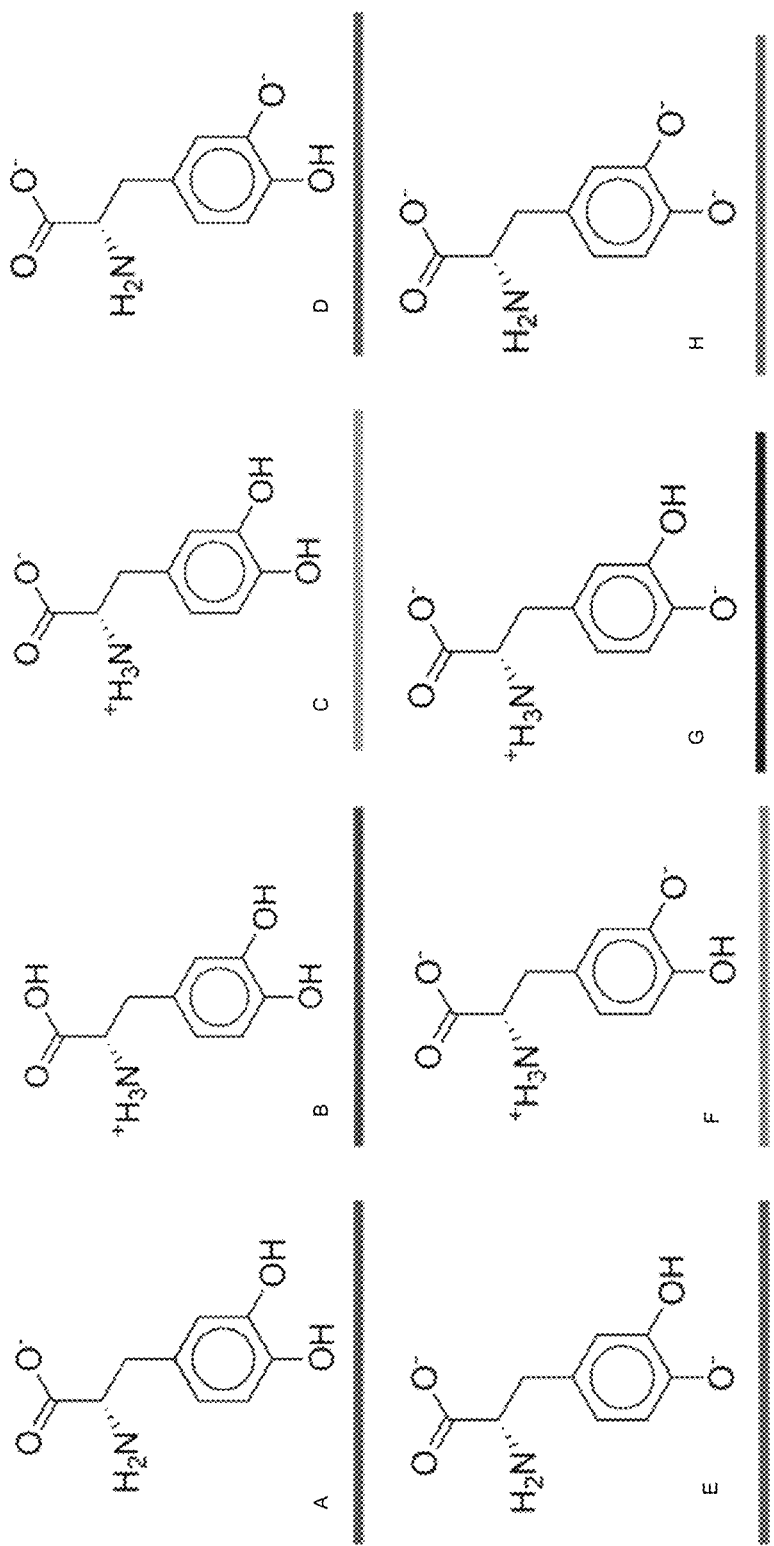

Developing a solution with high enough levodopa concentration making it suitable for continuous parenteral administration, with a pH value in the range of 3.0 to 8.5, which satisfies the product requirements of a medical drug is far from trivial. Levodopa has very poor solubility in the preferred pH range (pH=3.0 to 8.5) making it hard to prepare pharmaceutical formulations with levodopa concentrations high enough making them suitable for continuous parenteral administration, as levodopa tends to precipitate. The structure of levodopa is shown in FIG. 1, together with calculated pKa-values indicated at each centre of the molecule. Depending on the pH of the solution, these centres will be either protonated or deprotonated. A calculated micro-species distribution of levodopa is illustrated in FIGS. 5A and 5B, where the Y-axis denotes the percentage of each molecular form (in relation to the total amount), and the X-axis represents the pH-value. The pKa values of each centre give rise to the illustrated micro-species distribution. FIG. 2 shows the most dominating structure for levodopa in water at a pH in the range of 4 to 7. As illustrated by FIG. 2, levodopa will mainly be uncharged (neutral) at this pH interval.

Figure 3:
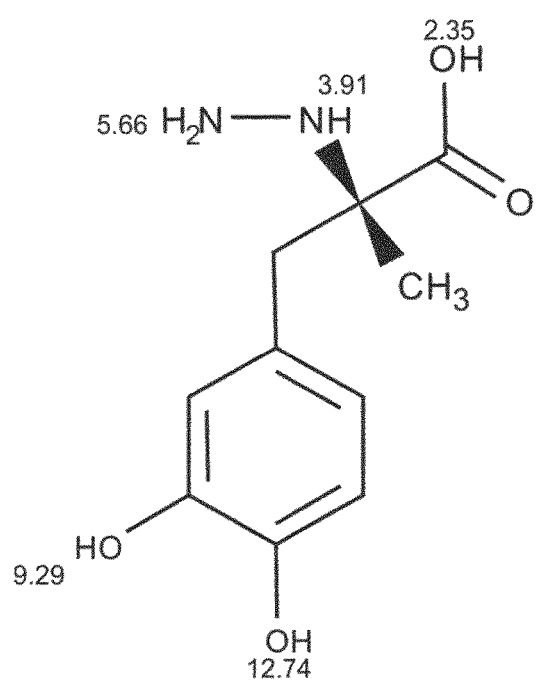
FIG. 3 is a structural representation of carbidopa with calculated pKa-values indicated at each centre of the molecule.
Figure 4:
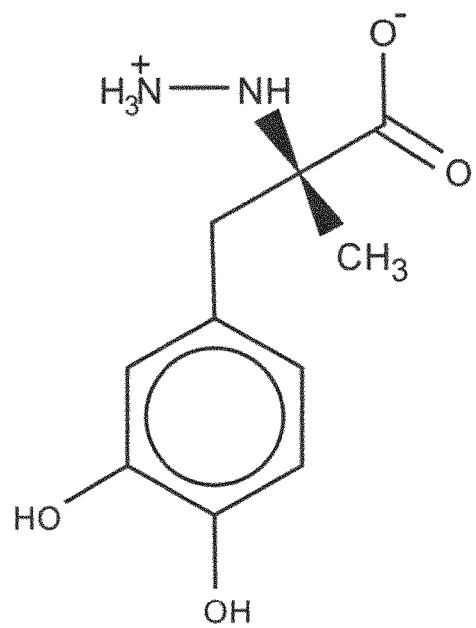
FIG. 4 is a structural representation of carbidopa with the structure that will dominate at a pH of approximately 5.
Figure 6A:
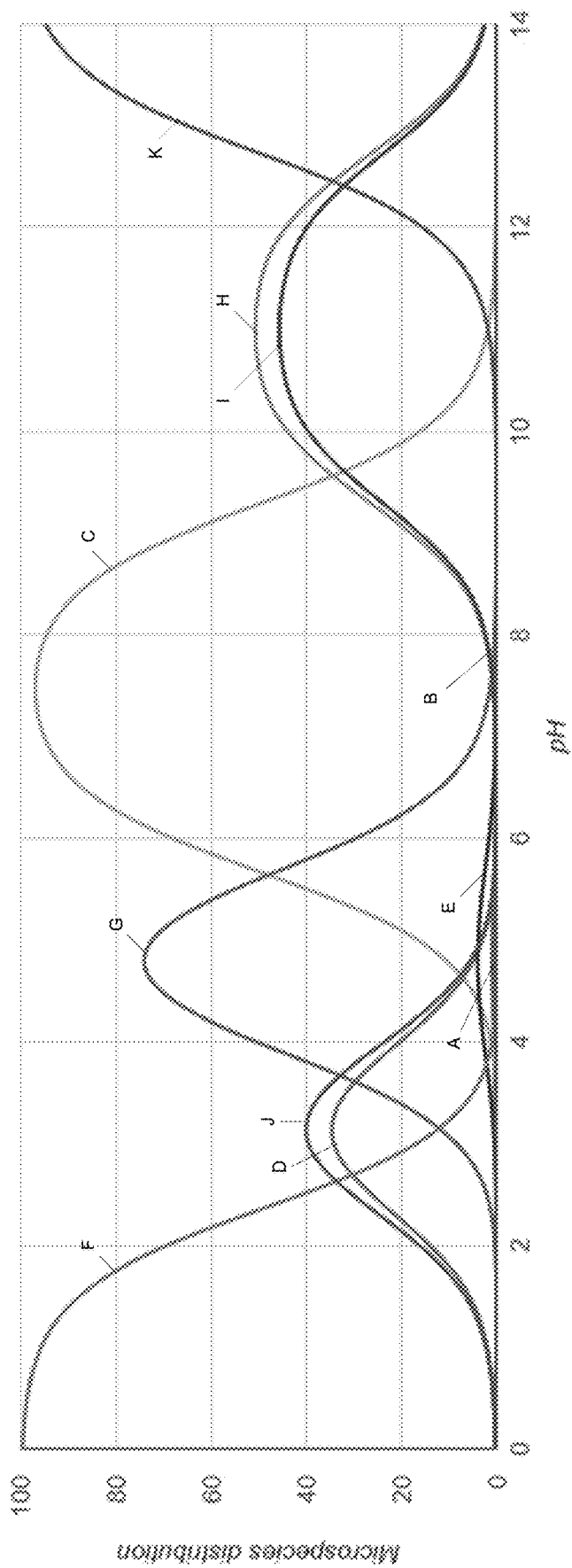
FIGS. 6A and 6B show a calculated micro-species distribution of carbidopa vs. pH, where the y-axis denotes the molar percentage of each molecular form in relation to the total amount, and the x-axis is the pH.
Figure 6B:
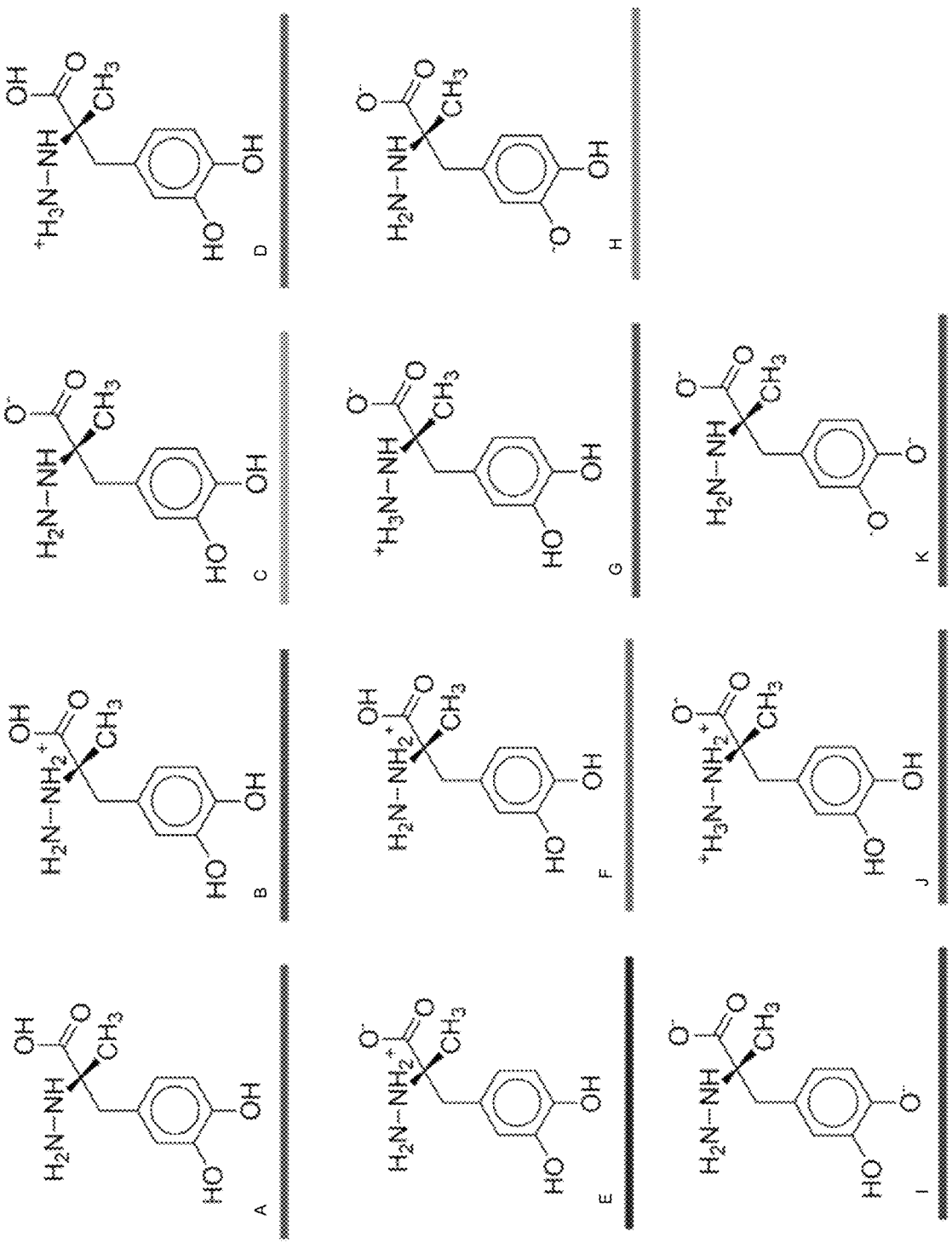

DOPA decarboxylase inhibitors; aromatic L-amino acid decarboxylase inhibitor (DDCI) are compounds, which inhibit the synthesis of dopamine by the enzyme aromatic L-amino acid decarboxylase. Peripheral DDCIs incapable of crossing the protective blood-brain-barrier (BBB) are used in augmentation of levodopa in the treatment of Parkinson's disease (PD) by blocking the peripheral conversion of levodopa into dopamine for reducing adverse side effects. Examples of such DOPA decarboxylase inhibitors are carbidopa, benserazide, and DFMD (alpha-Difluoromethyl-DOPA). The structure of the DOPA decarboxylase inhibitor carbidopa can be seen in FIG. 3, together with calculated pKa-values indicated at each centre of the molecule. A calculated micro-species distribution of carbidopa vs. pH is illustrated in FIGS. 6A and 6B, where the Y-axis denotes the percentage of each molecular form in relation to the total amount, and the X-axis represents the pH-value. FIG. 4 illustrates the most dominating structure for carbidopa in water at a pH around 5. At this pH, carbidopa will mainly be uncharged (neutral).

Figure 7:
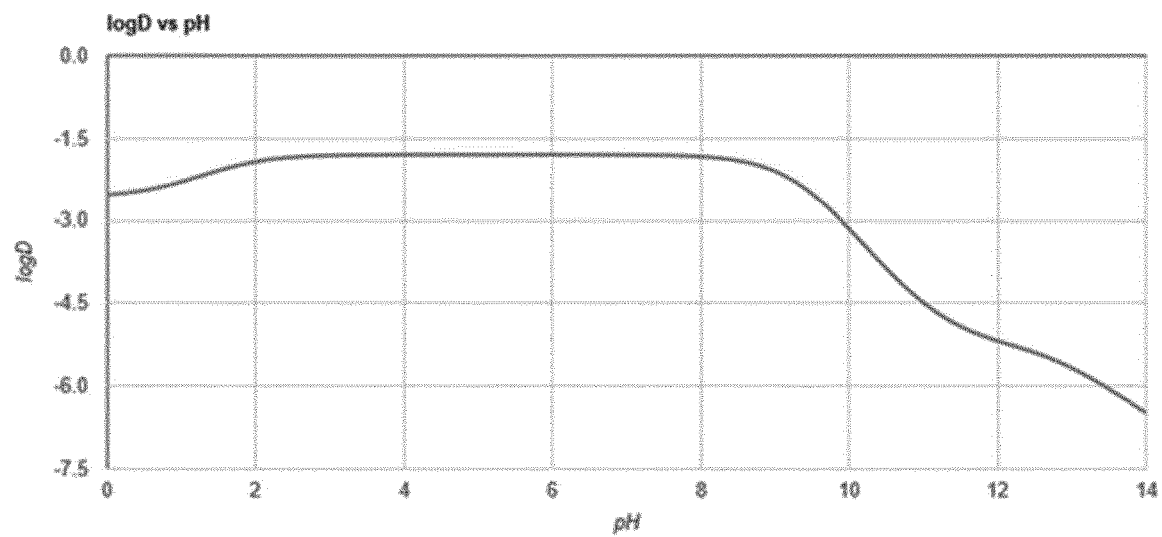
FIG. 7, shows a calculated distribution (D) between organic and aqueous phase (represented by the octanol-water distribution coefficient, log D) obtained for levodopa at different pH.
Figure 9:
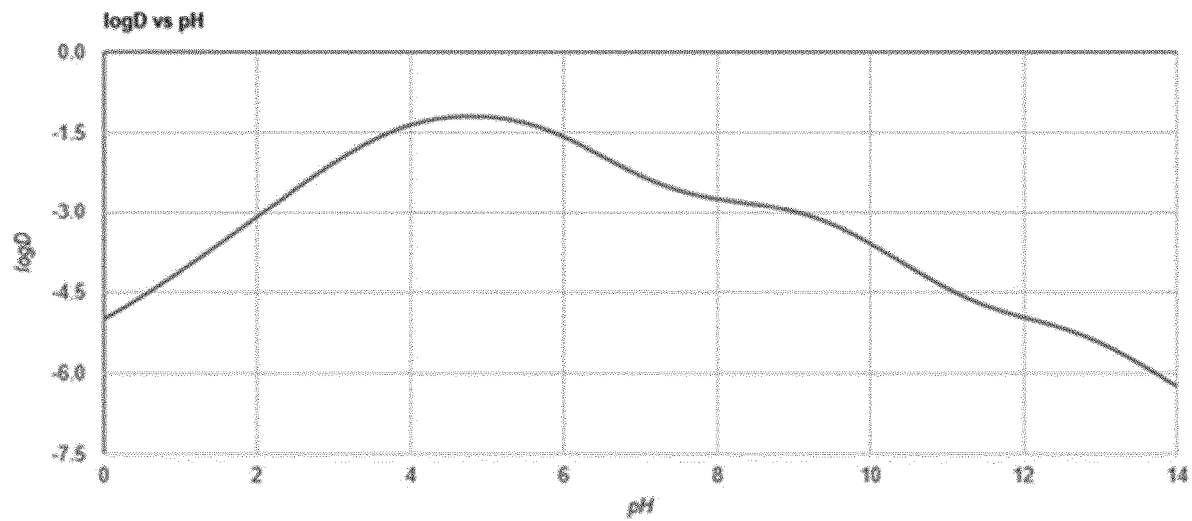
FIG. 9, shows a calculated distribution (D) between organic and aqueous phase (represented by the octanol-water distribution coefficient, log D) obtained for carbidopa at different pH.

Based on the above demonstrated micro distribution (where an uncharged compound will have higher lipophilicity than a charged one) and on the lipophilicity of similar molecular structures, a calculated distribution (D) between organic and aqueous phase (represented by the octanol-water distribution coefficient, log D) is shown for levodopa in FIG. 7. The log D value has its highest value at a pH range of 3 to 8. Hence, there will be an optimal distribution to lipids in this pH range. Similarly, a calculated distribution between organic and aqueous phase (represented by log D) is shown for carbidopa in FIG. 9. The log D value has its highest value in a pH-range of 4 to 6 with a maximum at a pH of approximately 5. At this pH the distribution to lipids will be at its optimum. Consequently, the pH ranges for producing the best lipid distribution for levodopa and carbidopa respectively, are overlapping each other. Taking the two curves together the preferred pH-range should be in the range of pH 5 to 6.

Figure 8:
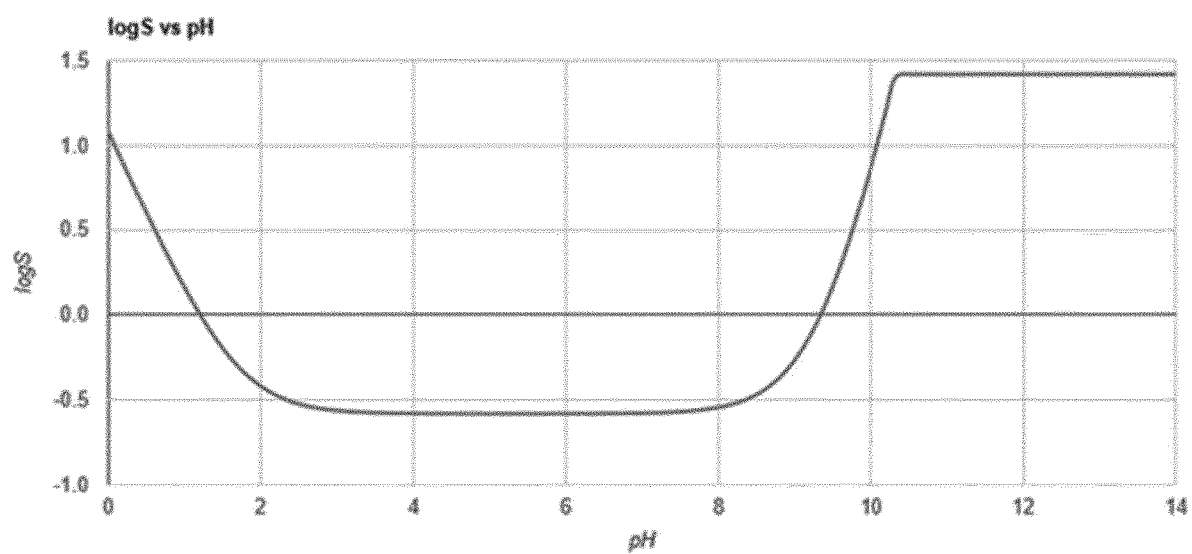
FIG. 8, shows a calculated solubility (represented by log S, the 10-based logarithm of the solubility measured in mol/l) obtained for levodopa at different pH.
Figure 10:
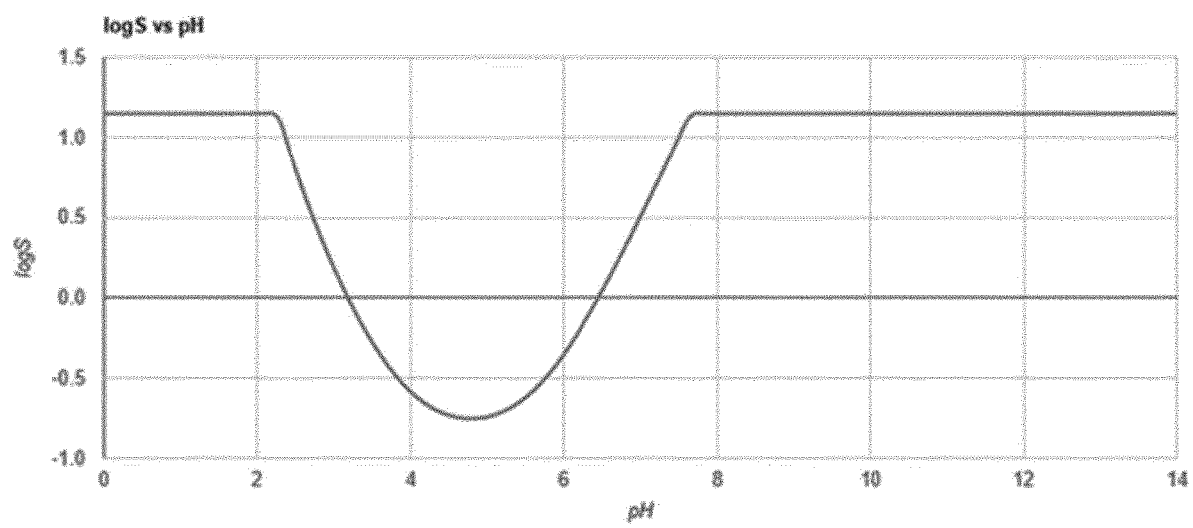
FIG. 10, which shows a calculated solubility (represented by log S, the 10-based logarithm of the solubility measured in mol/l) obtained for carbidopa at different pH.

The solubility of levodopa can be calculated based on the above-demonstrated micro distribution (where an uncharged compound will have lower solubility than a charged one) and the solubility (S) in aqueous phase of similar molecular structures. FIG. 8 shows a calculated solubility curve for levodopa, (represented by log S, the 10-based logarithm of the solubility measured in mol/l). The log S value is at its minimum at a pH-range of 3 to 8. In this pH range, the solubility of levodopa in aqueous phase will be at its lowest. Similarly, a calculated solubility curve (represented by log S) is shown for carbidopa in FIG. 10. The log S value is at a minimum at a pH value in the range of 4 to 6, with a minimum at about pH 5. Hence, at this pH, the solubility of carbidopa in aqueous phase will be at its lowest.

It is generally accepted that the higher the lipophilicity of a compound, the better its passive distribution into biological tissues and cells (Buxton and Benet, 2011). It is therefore likely that the optimal uptake of levodopa and carbidopa to the dermal tissues and capillary vessels will be obtained at a pH value of approx. 5 to 6 for levodopa and 5 for carbidopa respectively. This will in turn increase the rate of absorption and clinical effect of the substances when administered to a patient suffering from a CNS disease.

On the other hand, it is evident that the calculated solubility of levodopa and carbidopa in water is at its lowest at essentially the same pH interval. Thus, it would be desirable to increase the solubility as much as possible in this pH range. This may be obtained by choosing the proper ingredients for buffer systems and by selecting additives that increase the stability and the solubility of the APIs. In order to optimize the overall function, the pH value may be varied slightly around the optimal pH range.

Furthermore, and importantly, the present invention teaches that by using an oversaturated solution (oversaturated with the APIs), which is administered to the human body shortly (such as within minutes) after the APIs have been mixed (and prior to precipitation), the concentration of the APIs may be considerably increased at the chosen pH-range (versus using a standard administration system). This principle is in direct contrast to the prevailing opinion in the field.

The risk of metabolic alkalosis at high pH-values is another reason for keeping a parenteral pharmaceutical solution at a pH below 7. Metabolic alkalosis may lead to hypocalcemia and subsequent headache, lethargy, neuromuscular excitability sometimes with delirium, tetany and seizures. Moreover, clinical studies performed show that high pH-values may cause alkalemia, which lowers the threshold for angina symptoms and arrhythmias (J Lewis, 2017).

Administration of the pharmaceutical solution resulting from mixing the aqueous stock solution and aqueous buffering solution disclosed herein can be by parenteral or enteral administration. Parenteral administration is a route of administration that does not involve drug absorption via the gastrointestinal tract. Parenteral administration routes include but are not limited to subcutaneous, intravenous, intrathecal, intradermal, intra-arterial, intraosseous, intramuscular, intracerebral, and intracerebroventricular. In some embodiments, the parenteral administration is subcutaneous. In some embodiments, the parenteral administration is intravenous. Enteral administration involves administration through the gastrointestinal tract. Enteral administration routes include but are not limited to oral, sublingual, buccal, duodenal, and rectal. In some embodiments, the enteral administration is duodenal.

A solution suitable for parenteral administration must as well fulfil several other conditions. Administering too-dilute or too-concentrated a solution may disrupt the patient's balance of sodium, potassium, magnesium and other electrolytes. Thus, a parenteral pharmaceutical solution should preferably have an osmolality in the range of 150 to 1500 milli-osmoles, preferably 300 to 600 or 500 to 1000 milli-osmoles per kilogram. The aforesaid requirement on the osmolality is fulfilled by the present invention, which contributes to it being suitable as a pharmaceutical product.

The inventors have found that an aqueous pharmaceutical infusion or injection solution with a desired pH (3.0-8.5) for use in the treatment of diseases of the central nervous system (CNS), can be achieved by using a system of two liquids, an aqueous stock solution containing levodopa and optionally an inhibitor, such as carbidopa, and a corresponding aqueous buffering diluting solution, which are mixed shortly prior to treatment.

By using an optimized aqueous stock solution together with an optimized aqueous buffer solution, it was found that the two solutions can be rapidly mixed without precipitation taking place. This is contrary to previous teachings, such as that of WO 2006/006929, where the solution preparation relies on the buffer solution being added to the stock solution slowly in small portions at a time and during constant stirring. As such, the aqueous stock solution and the aqueous buffering solution of the present invention can be easily mixed just before treatment, for instance using a medical bag or container with two compartments, one holding the aqueous stock solution and the other one holding the aqueous buffering solution. Such an infusion or injection solution only needs to be stable for a few hours down to mere minutes. This in turn opens up for the use of levodopa and/or carbidopa concentrations exceeding 10 mg/ml at the desired pH range.

According to one embodiment, an aqueous pharmaceutical solution for use in the treatment of diseases of the central nervous system (CNS) comprising at least 5 mg/ml dissolved levodopa, and having a pH in the range of 3.0 to 8.5, is provided. The solution is provided by mixing (a) an aqueous stock solution comprising levodopa and (b) an aqueous buffering solution, for increasing the pH of said stock solution. The aqueous stock solution has a pH of less than 2.8 at 25° C. The aqueous buffering solution comprises at least one buffer component and has a pH of at least 4.0 at 25° C. The aqueous pharmaceutical solution is administered to a subject suffering from a disease of the central nervous system (CNS) within 24 hours, such as within 16 hours, 12 hours, 6 hours, 4 hours, 2 hours, 1 hour, 30 minutes, 20 minutes, 10 minutes, 5 minutes, or 1 minute, from mixing the aqueous stock solution and the aqueous buffering solution.

The stability of levodopa decreases with increasing concentration. Therefore, more dilute formulations will be physically stable for longer periods of time. In certain embodiments, the pharmaceutical solution comprises at most 10 mg/ml levodopa, and is administered within 24 hours of the aqueous stock solution and the aqueous buffering solution being mixed. These embodiments may be formulated for injection or infusion.

Surprisingly, the optimized properties of the stock- and buffering solution, together with the suitability for rapid mixing, allows for the formation of supersaturated pharmaceutical solutions of levodopa, optionally also containing carbidopa, at a physiologically acceptable pH and osmolality. Thus, in one further embodiment, the aqueous pharmaceutical solution is supersaturated with levodopa.

Supersaturation is a state of a solution that contains more of the dissolved material than could be dissolved by the solvent under normal circumstances at a given temperature. The long-term stability of such a solution is most often relatively short since the supersaturated solution, from a thermodynamic point of view, is not energetically favoured. However, the precipitation of the solute takes time because the molecules need to meet up and form the precipitate without being knocked apart by water. Also, a nucleation event may be required to trigger precipitation. The larger the molecule, the longer time it will take due to the principles of Brownian motion.

In certain embodiments, the concentration of levodopa may be increased to the point of supersaturation. At levodopa concentrations higher than 10 mg/mL, precipitation of levodopa is observed. Due to the lower physical stability of oversaturated solutions, on line mixing can be used to ensure the solution remains stable upon administration to a patient. The use of on line mixing allows for continuous mixing of the aqueous stock solution and the aqueous buffering solution, followed by continuous administration of the resulting aqueous pharmaceutical solution within 2 hours of the stock solutions being mixed. In some embodiments, the aqueous pharmaceutical solution is administered within 1.5 hours, 1 hour, 50 minutes, 40 minutes, 30 minutes, 20 minutes, 10 minutes, 5 minutes or 1 minute, from mixing the aqueous stock solution and the aqueous buffering solution.

According to one embodiment, an aqueous pharmaceutical solution for use in the treatment of diseases of the central nervous system (CNS) comprising at least 5 mg/ml dissolved levodopa and having a pH in the range of 3.0 to 8.5 is provided, wherein said aqueous pharmaceutical infusion or injection solution is supersaturated with levodopa.

In one further embodiment, the aqueous pharmaceutical solution is provided by mixing (a) an aqueous stock solution comprising levodopa and (b) an aqueous buffering solution, for increasing the pH of said stock solution. The aqueous stock solution has a pH of less than 2.8 at 25° C. The aqueous buffering solution comprises at least one buffer component and has a pH of at least 4.0 at 25° C.

In some embodiment, the aqueous stock solution has a pH of less than 2.0, such as less than 1.5, 1.0 or 0.5; preferably the pH of the aqueous stock solution has a pH being in the range of 0.0 to 2.0, such as 0.0 to 1.5, 0.0 to 1.0, or 0.0 to 0.5. Optionally, the aqueous stock solution has a pH in the range of 0.0 to 1.0. The aqueous stock solution may comprise at least one physiologically acceptable acid. In some embodiments, the physiologically acceptable acid is a mineral acid, such as hydrochloric acid, sulfuric acid or nitric acid. Optionally, the mineral acid is hydrochloric acid (HCl); preferably the aqueous stock solution comprising at least 30 mM HCl, such as at least 50 mM HCl, 100 mM HCl, or 150 mM HCl. In some embodiments, the physiologically acceptable acid is acetic acid. In one embodiment, the physiologically acceptable acid is acetic acid, lactic acid, tartaric acid, maleic acid, sodium bicarbonate or sodium phosphate. The aqueous stock solution may comprise more than one physiologically acceptable acid. Optionally, the aqueous stock solution comprises at least 10 mg/ml levodopa, such as at least 15, 20, 25, 30, 35 or 40 mg/ml levodopa.

In some embodiments, the aqueous buffering solution has a pH between 4 and 12 at 25° C. The pH of the aqueous buffering solution may be in the range of 4 to 12, such as 4 to 9, such as 4 to 7.5, such as 4 to 6. The aqueous buffering solution may comprise at least one buffer component having at least one pKa value within the range of 3 to 9. Optionally, at least one buffer component has at least one pKa value in the range of 5 to 7.5. Optionally, at least one buffer component has at least one pKa value in the range of 4 to 6. In some embodiments, the buffer is selected from the group consisting of adipic acid, boric acid, calcium carbonate, calcium lactate, calcium phosphate, diethanolamine, glycine, maleic acid, meglumine, methionine, monosodium glutamate, potassium citrate, sodium acetate, sodium bicarbonate, sodium carbonate, sodium citrate dihydrate, sodium lactate, di-sodium hydrogen phosphate dihydrate, sodium phosphate monobasic, tris(hydroxymethyl) aminomethane or a combination thereof. The buffer component may be citric acid. Optionally, the buffer components are citric acid and phosphate.

The details of the aqueous pharmaceutical solution provided by any of the above mixing methods and comprising at least 5 mg/ml dissolved levodopa are explained more in detail below.

Patients in the late stages of PD may require up to 1,000 mg levodopa per day by the oral route. A levodopa concentration in the range of 0.5 to 1.0 mg/ml results in administration volumes of 1 to 2 litres/per day. Therefore, the stock solution should preferably comprise at least 5 mg/ml levodopa. However, a levodopa concentration of 5 mg/ml is on the low side for an infusion solution intended for parenteral administration—especially if there is no inhibitor included in the solution. An infusion solution intended for continuous subcutaneous infusion should include an inhibitor and contain at least 10 mg/ml levodopa. A series of mixing experiments using the approach of the invention are summarized in tables 8 to 20, highlighting the effect of the use of different formulations containing acids, buffers, stabilizers and other additives. By mixing the specified stock and buffering solutions of the invention, immediately prior to administration of the resulting infusion solution, pharmaceutically acceptable infusion solutions with levodopa concentrations of 10 mg/ml and higher, at the desired pH range, can be obtained. This has never previously been achieved. Neither has it, prior to the invention, been taught in the art.

Thus, according to one embodiment, the aqueous pharmaceutical solution comprises at least 5 mg/ml dissolved levodopa, such as at least 6, 7, 8, 9, 10, 15, or 20 mg/ml dissolved levodopa. In one embodiment, the aqueous pharmaceutical solution comprises at least 5 mg/ml dissolved levodopa, such as at least 6, 7, 8, 9, 10, or 15 mg/ml dissolved levodopa. In one embodiment, the aqueous pharmaceutical solution comprises at least 5 mg/ml dissolved levodopa, such as at least 6, 7, 8, 9, or 10 mg/ml dissolved levodopa. The aqueous pharmaceutical solution may thus comprise 5 to 20 mg/ml dissolved levodopa, such as 5 to 15 mg/ml, or 5 to 10 mg/ml dissolved levodopa. In some embodiments, the aqueous pharmaceutical solution comprises at least 10 mg/ml dissolved levodopa. The aqueous pharmaceutical solution may thus comprise 10 to 20 mg/ml dissolved levodopa, such as 10 to 15 mg/ml, or 15 to 20 mg/ml dissolved levodopa.

As described above, the desired pH of the aqueous pharmaceutical solution is in the range of 3.0 to 8.5. As illustrated by FIG. 7 this interval coincides with higher lipophilicity of levodopa, which is even more pronounced at a pH from 3.5, 4, 4.5, or 5 to 5, 5.5, 6.0, 6.5, or 7.0, resulting in better passive distribution into biological tissues and cells, which in turn will increase the rate of absorption and clinical effect of the substances. In one embodiment, the aqueous pharmaceutical solution has a pH of between 3.5 and 8.0, such as between 4.0 and 7.5, 4.0 and 5.0, or 4.5 and 7.0. In one further embodiment, the aqueous pharmaceutical solution has a pH of between 4.3 and 4.6. In some embodiments, the aqueous pharmaceutical solution has a pH of between 5.0 and 6.0.

In table 22, interim data from a clinical trial are summarized and show that a solution of the invention has high bioavailability for both levodopa and carbidopa, at continuous subcutaneous infusion. The high bioavailability for carbidopa at subcutaneous infusion supports the finding that the lipophilicity of an API is of utmost importance for the uptake in the blood of the API concerned. The pH of the infusion solution of the invention is close to 5 i.e. where the lipophilicity of carbidopa is at its optimum. Consequently, the bioavailability (and the corresponding uptake of carbidopa in the plasma) at subcutaneous infusion is around 100% as opposed to the bioavailability for carbidopa of the intestinal gel Duodopa, which is around 75%. The bioavailability of levodopa being around 100% for both Duodopa and the infusion solution of the invention may be explained by the lipophilicity of levodopa being optimal over a much broader pH-range (3-8) as illustrated in FIG. 7.

By administering the solution shortly after mixing, pharmaceutically acceptable infusion solutions with even higher levodopa and/or carbidopa concentrations may be obtained at the desired pH range.

Figure 14A:
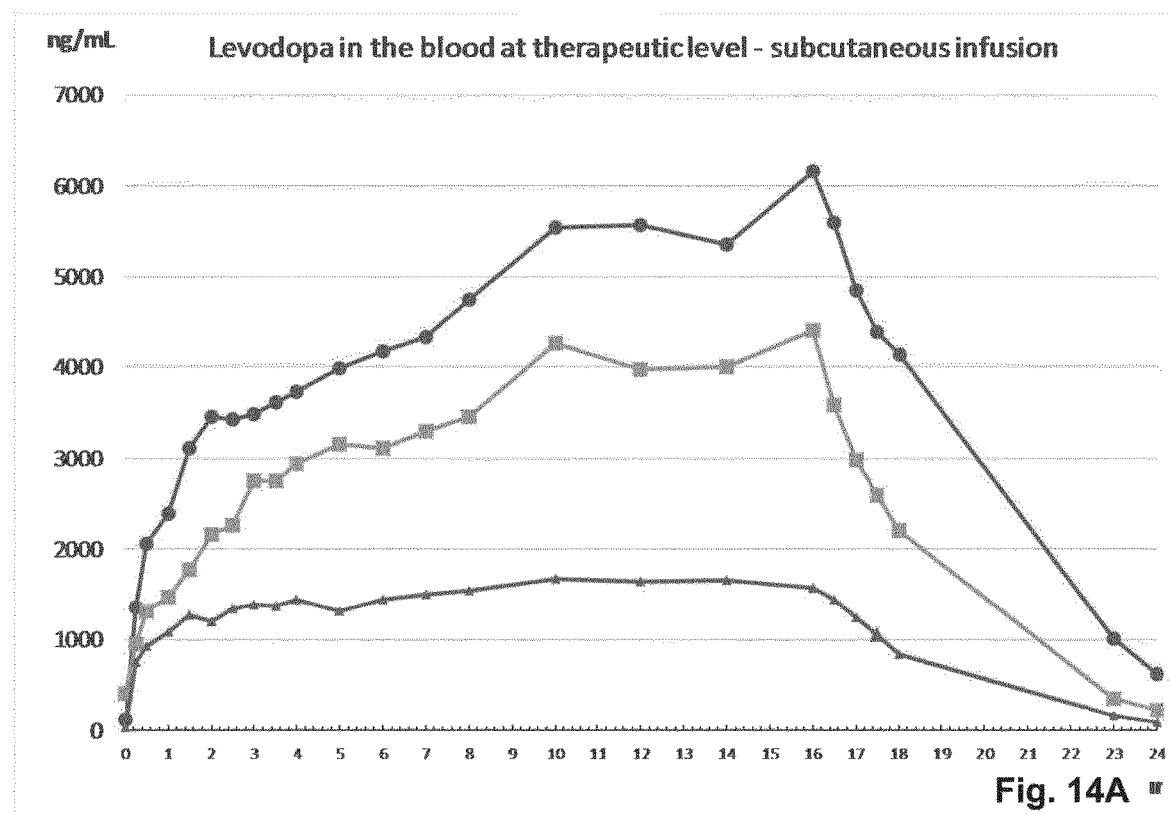
FIG. 14, which shows results from clinical trial interim studies for three patients, where blood levels of Levodopa are monitored in the patients' plasma during (a) subcutaneous and (b) intravenous infusion and plotted against treatment time.

The increased rate of absorption of levodopa allows for the treatment to be personalized for individual patients. Depending on the stage of PD that a patient is in, the amount of levodopa required to achieve a therapeutic effect will differ. The therapeutic effect (for a patient suffering from on-off symptoms related to Parkinson's disease) is reached when the levodopa concentration in the blood reaches the levels required for the patients concerned. The large difference in levodopa levels required by different patients is illustrated by FIGS. 14A and B. One of the patients (patient no 101) suffering from severe PD requires levodopa concentrations in the order of 5,000-6,000 ng/mL in the blood while another patient with moderate or mild PD (patient no 103) only requires 1,600-1,700 ng/mL for having therapeutic effect. The therapeutically effective amount needed for a patient suffering from PD will depend on, for example, the subject's size, health, age, and the stage of Parkinson's disease the patient is in. The rapid absorption of levodopa and carbidopa in the blood allows for the flow rate of the pharmaceutical solution to be adjusted until the desirable effect is achieved for each individual patient. Adjusting the flow rate of the pharmaceutical solution (by adjusting the flow rate of the pump(s), which are providing the stock solution and the buffering solution to the mixing device) allows control of both the response time (the time when the infusion is started in the morning at off stage till the point of time when, at first, a therapeutic effect is reached) and the concentration of the APIs in the blood enabling the on-off symptoms to be minimized.

The fact that the formulations allow for instant mixing of the stock- and the buffering solutions enables an "on line" administration approach of the invention, wherein the specified stock and buffering solutions may be continuously mixed and the resulting infusion solution may be continuously administered. This is especially favourable for continuous subcutaneous infusion, where the infusion solution may be continuously mixed, providing a completely fresh infusion solution, during the course of the slow continuous infusion. Such an approach is not possible using known solutions or formulations in prior art, but the inherent properties of the solutions of the invention allows for rapid online mixing, and due to the following rapid online administration, any degradation of APIs will be well within the limits for pharmaceutical regulations. In table 21, results are summarized for on line mixing experiments using solutions of the invention and an online mixing system.

In one embodiment, the aqueous pharmaceutical solution is administered to a subject suffering from a disease of the central nervous system (CNS) within 2 hours, such as within 90 minutes, 60 minutes 50 minutes, 40 minutes, 30 minutes, 20 minutes, 10 minutes, 5 minutes, or 1 minute, from mixing the aqueous stock solution and the aqueous buffering solution.

In one embodiment, the aqueous buffering solution and aqueous stock solution are continuously mixed and the thereby obtained aqueous pharmaceutical solution is continuously administered to the subject suffering from a disease of the central nervous system (CNS).

In one embodiment, the aqueous pharmaceutical solution is administered to a subject suffering from a disease of the central nervous system (CNS) within 1 hour, such as within 50 minutes, 40 minutes, 30 minutes, 20 minutes, 10 minutes, 5 minutes, or 1 minute, from mixing the aqueous stock solution and the aqueous buffering solution. According to a one embodiment, the aqueous pharmaceutical solution is administered to a subject suffering from a disease of the central nervous system (CNS) within 10 minutes, 8 minutes, 6 minutes, 4 minutes, 2 minutes, or 1 minute, from mixing the aqueous stock solution and the aqueous buffering solution.

In one embodiment, the aqueous pharmaceutical solution is administered before 15 wt %, such as before 10 wt %, of the levodopa in the aqueous pharmaceutical solution has degraded.

In one embodiment, the time from the mixing of the aqueous stock solution and the aqueous buffering solution to the administration of the aqueous pharmaceutical solution to a subject suffering from a disease of the central nervous system (CNS), is shorter than the time from mixing of the aqueous stock solution and the aqueous buffering solution to the time when 15 wt %, such as 10 wt %, of the levodopa in the aqueous pharmaceutical solution is degraded.

Various factors may influence the stability of levodopa and carbidopa in the aqueous pharmaceutical solutions, such as concentration, and the presence of other additives in the solution. In some embodiments, the aqueous pharmaceutical solution is both physically and chemically stable for up to 24 hours. In other embodiments, the aqueous pharmaceutical solution is physically stable for only 2 hours and the degradation of the APIs may violate acceptable limits within 30 minutes. The stability of the solution can be determined using methods well known in the art. For instance, somebody skilled in the art will appreciate that the toxic by-products resulting from API degradation may be detected using High Pressure Liquid Chromatography (HPLC). Depending on the stability of the aqueous pharmaceutical solution, different methods of mixing the aqueous stock solution and the aqueous buffering solution are possible. For example, aqueous pharmaceutical solutions with a higher degree of stability may be mixed up to 24 hours prior to administering said solution to a patient. Such solutions may be provided in two separate compartments of a single bag separated by a perforable barrier. Once the barrier is punctured, such as by squeezing the bag, the two solutions are allowed to mix. Squeezing the bag further will allow for sufficient mixing of the solutions, yielding the aqueous pharmaceutical solution, which will be sufficiently stable to administer to a patient within 24 hours. Alternatively, for aqueous pharmaceutical solutions with a lower degree of stability, an on-line mixing approach may be used, to ensure that the level of API degradation and the concentration of toxic by-products remains within an acceptable limit. The on line mixing will allow for the aqueous stock solution and aqueous buffering solution to be mixed continuously as the resulting aqueous pharmaceutical solution is continuously administered to a patient. This on line mixing approach will allow for the administration of solutions to a patient, which would otherwise be unavailable, due to their limited window of stability.

While both the stock solution and the buffering solution must meet conditions for sufficient stability and solubility, the resulting aqueous pharmaceutical solution must still fulfil the above discussed criteria (controllable risk of precipitation, suitable pH-range, limited degradation of the APIs, limited content of toxic by-products, acceptable osmolality level etc.) to be suitable for parenteral administration. This means, that a stock solution containing levodopa optimized for stability, may not be suitable for being mixed with a buffering solution nor result in a suitable aqueous pharmaceutical infusion or injection solution for use in the treatment of diseases of the central nervous system. This is further illustrated below. Thus, it is necessary to specifically design both the stock solution and the buffering solution in order for the solutions to meet the necessary parameters both prior to, during and after mixing.

It is well known that low pH-values improve the solubility. However, a low pH value of the stock solution would require mixing with a strong alkali buffer solution in order to arrive at a pH value that is preferred for clinical use. As shown, e.g. in table 20, the osmolality of the final solution becomes very high when high concentrations or several additives are used in the stock- and buffering solutions. The normal human reference range of osmolality in the plasma is about 285-295 milli-osmoles per kilogram and too high osmolality will adversely affect local tolerance in the human body at the cellular level. Thus, in one embodiment, the aqueous pharmaceutical solution has an osmolality of 50 to 1400 mOsm/kg, preferably 100 to 1000 or even 200 to 600 mOsm/kg.

During the experiments summarized in tables 1 to 7, the stability of the stock solution was evaluated. It was found that stock solutions of levodopa with a pH value of <3 had excellent stability when refrigerated, with no significant degradation after 4 months. Solutions containing levodopa and carbidopa, having a pH-value above 3, showed carbidopa-degradation over time.

In one embodiment, the aqueous stock solution comprises at least 10 mg/ml levodopa, such as at least 15, 20, 25, 30, 35, or 40 mg/ml of levodopa. In one embodiment, the aqueous stock solution has a pH of less than 2.0, such as less than 1.5, 1.0 or 0.5. The pH of the aqueous stock solution may be in the range of 0.0 to 2.0, such as 0.0 to 1.5, 0.0 to 1.0, or 0.0 to 0.5.

In order to provide a low pH, the aqueous stock solution may comprise a physiologically acceptable acid, preferably a mineral acid such as hydrochloric acid, sulfuric acid, or nitric acid. In one embodiment, the physiologically acceptable acid is HCl. Preferably the aqueous stock solution comprises at least 30 mM HCl, such as at least, 50 mM HCl, 100 mM HCl, or 150 mM HCl. In one embodiment, the physiologically acceptable acid is acetic acid, lactic acid, tartaric acid, maleic acid, sodium bicarbonate or sodium phosphate. The aqueous stock solution may comprise more than one physiologically acceptable acid.

In some embodiments, the aqueous stock solutions disclose herein may comprise at least one stabilizer. The stabilizer may be sodium metabisulfite. Sodium metabisulfite is a preferred stabilizer, as it has been found to have a positive effect on the long-term storage of the stock solution. Sodium metabisulfite (also known as sodium pyrosulfite) is an inorganic compound of chemical formula $Na_2S_2O_5$. Sodium metabisulfite oxidizes in the liver to sulfate which is excreted in the urine, whereby tens of milligrams can be taken as a daily dose without causing adverse effects.

As seen in the experiments summarized in table 5, de-airing of the solutions, e.g. the aqueous stock solution, also had a positive effect on long term stability and the reproducibility and consistency of results for certain of the experiments. In one embodiment, the aqueous stock solution has been de-aired; such as by bubbling of an inert gas, e.g. nitrogen, through the stock solution. According to one embodiment, the buffering solution was de-aired using an inert gas, such as nitrogen, which was allowed to bubble through the solution.

Including a DOPA decarboxylase inhibitor is advantageous in that it prevents the metabolization of levodopa in the plasma in the systemic circulation. Examples of DOPA decarboxylase inhibitors are carbidopa, benserazide, methyldopa, and DFMD (alpha-Difluoromethyl-DOPA). In some embodiments, the DOPA decarboxylase inhibitor is carbidopa. COMT inhibitors are as well, often in combination with other medications, used in the treatment of Parkinson's disease. COMT inhibitors inhibit the action of catechol-O-methyl transferase, an enzyme involved in degrading neurotransmitters. Examples of COMT-inhibitors are entacapone, tolcapone, opicapone and nitecapone. Monoamine oxidase inhibitors (MOAIs) inhibit the activity of the monoamine oxidase enzyme family (therefore affecting dopaminergic neurons) that have been used in treatment of Parkinson's disease. Examples of MOAIs are rasagiline, selegiline and safinamide.

Thus, the aqueous pharmaceutical solution according to an embodiment further comprises at least one enzyme inhibitor. In some embodiments, the stock solution comprises at least one dopa decarboxylase (DDC) inhibitor, or at least one catechol-o-methyltransferase (COMT) inhibitor, or at least one monoamino oxidase (MAO-B) inhibitor, or a combination thereof. The dopa decarboxylase (DDC) inhibitor may be selected from the group consisting of carbidopa, such as carbidopa monohydrate, enserazide, methyldopa, and DFMD (alpha-Difluoromethyl-DOPA). The catechol-o-methyltransferase (COMT) inhibitor may be selected from the group consisting of entacapone, tolcapone, and nitecapone. The monoamino oxidase (MAO-B) inhibitor may be selected from the group consisting of rasagiline, selegiline and safinamide.

The aqueous buffering solution is designed to match the properties of the stock solution for the purpose of arriving at/after mixing an aqueous pharmaceutical solution with desired properties (such as desired pH-value, good buffering capacity, minimal degradation of the APIs) within a specified time frame, minimal content of toxic by-products, and acceptable osmolality level etc. One important property of the buffering solution is to increase the pH of the mixed solution while keeping the stock solution components from precipitating. In one embodiment, the aqueous buffering solution has a pH of at least 4.0. The pH of the aqueous buffering solution may be in the range of 4 to 12, such as 4 to 9, such as 4 to 7.5, such as 4 to 6. In one embodiment, the aqueous buffering solution comprises at least one buffer component having at least one pKa value between 3 and 9, such as between 5 and 7.5.

The pH of buffers in acidic or alkaline regions, may be adjusted by adding a strong acid (such as hydrochloric acid), or a strong base (such as sodium hydroxide), respectively, to the buffering agent. Alternatively, a buffer can be made from a mixture of an acid and its conjugate base. For example, an acetate buffer can be made from a mixture of acetic acid and sodium acetate. Similarly, an alkaline buffer can be made from a mixture of the base and its conjugate acid. The buffer capacity of a buffering agent is at a local maximum when pH=pKa. It falls to 33% of the maximum value at pH=pKa±1 and to 10% at pH=pKa±1.5. As such, the useful buffering range is approximately pKa±1. By combining buffer components with pKa values differing by only two units or less and adjusting the pH, a wide range of buffers can be obtained. The buffering capacity being proportional to the concentration of the buffering agent, results in dilute solutions having less buffering capacity.

There are several pharmaceutically suitable buffer components that can be combined to create suitable buffering solutions. Examples of such suitable buffer components are:

adipic acid—acidity/alkalinity pH=2.7 (saturated solution at 25° C.); pH=3.2 (0.1% w/v aqueous solution at 25° C.), boric acid—acidity/alkalinity pH=3.5-4.1 (5% w/v aqueous solution), calcium carbonate—acidity/alkalinity pH=9.0 (10% w/v aqueous dispersion), calcium lactate—acidity/alkalinity pH=6.0-8.5 for a 10% aqueous solution, calcium phosphate, tribasic—acidity/alkalinity pH=6.8 (20% slurry in water), citric acid monohydrate—acidity/alkalinity pH=2.2 (1% w/v aqueous solution), diethanolamine—acidity/alkalinity pH=11.0 for a 0.1 in aqueous solution, glycine—acidity/alkalinity pH=4 (0.2M solution in water), maleic acid—acidity/alkalinity pH 2 (5% w/v aqueous solution at 25° C.), methionine—acidity/alkalinity pH=5.6-6.1 (1% w/v aqueous solution), monosodium glutamate—acidity/alkalinity pH=7.0 (0.2% w/v aqueous solution), potassium citrate—acidity/alkalinity pH=8.5 (saturated aqueous solution), sodium acetate—acidity/alkalinity pH=7.5-9.0 (5% w/v aqueous solution), sodium bicarbonate—acidity/alkalinity pH=8.3 for a freshly prepared 0.1M aqueous solution at 25° C., sodium borate—acidity/alkalinity pH=9.0-9.6 (4% w/v aqueous solution), sodium carbonate—acidity/alkalinity strongly alkaline; pH=11.4 (1% w/v aqueous solution at 25° C., sodium citrate dihydrate—acidity/alkalinity pH=7.0-9.0 (5% w/v aqueous solution), sodium lactate—acidity/alkalinity pH=7 for an aqueous solution, sodium phosphate, dibasic—acidity/alkalinity pH=9.1 for a 1% w/v aqueous solution of the anhydrous material at 25° C., sodium phosphate, monobasic—acidity/alkalinity pH=4.1-4.5 for a 5% w/v aqueous solution of the monohydrate at 25° C., meglumine—acidity/alkalinity pH=10.5 (1% w/v aqueous solution), and trometamol.

According to another embodiment, there are several pharmaceutically suitable buffer components that can be combined to create suitable buffering solutions. Examples of such suitable buffer components are:

adipic acid—acidity/alkalinity pH=2.7 (saturated solution at 25° C.); pH=3.2 (0.1% w/v aqueous solution at 25° C.), boric acid—acidity/alkalinity pH=3.5-4.1 (5% w/v aqueous solution), citric acid monohydrate—acidity/alkalinity pH=2.2 (1% w/v aqueous solution), diethanolamine—acidity/alkalinity pH=11.0 for a 0.1 in aqueous solution, glycine—acidity/alkalinity pH=4 (0.2M solution in water), maleic acid—acidity/alkalinity pH 2 (5% w/v aqueous solution at 25° C.), methionine—acidity/alkalinity pH=5.6-6.1 (1% w/v aqueous solution), monosodium glutamate—acidity/alkalinity pH=7.0 (0.2% w/v aqueous solution), potassium citrate—acidity/alkalinity pH=8.5 (saturated aqueous solution), sodium acetate—acidity/alkalinity pH=7.5-9.0 (5% w/v aqueous solution), sodium bicarbonate—acidity/alkalinity pH=8.3 for a freshly prepared 0.1M aqueous solution at 25° C., sodium borate—acidity/alkalinity pH=9.0-9.6 (4% w/v aqueous solution), sodium carbonate—acidity/alkalinity strongly alkaline; pH=11.4 (1% w/v aqueous solution at 25° C., sodium citrate dihydrate—acidity/alkalinity pH=7.0-9.0 (5% w/v aqueous solution), sodium lactate—acidity/alkalinity pH=7 for an aqueous solution, sodium phosphate, dibasic—acidity/alkalinity pH=9.1 for a 1% w/v aqueous solution of the anhydrous material at 25° C., sodium phosphate, monobasic—acidity/alkalinity pH=4.1-4.5 for a 5% w/v aqueous solution of the monohydrate at 25° C., meglumine—acidity/alkalinity pH=10.5 (1% w/v aqueous solution), and trometamol.

The buffer component may preferably be citric acid, which has a multipurpose function in that it serves both as a buffer component and a stabilizer. Tests performed by the inventors clearly demonstrate the citric acid's stabilizing effect on the APIs of the invention. U.S. Pat. No. 8,815,950 B2 teaches that the stabilizing effect of citric acid is non-existent, or at least very low, at pH-values exceeding 4. In spite of this, as can be seen in tables 14 to 15, using a two-solution-system together with a citrate/phosphate buffering system surprisingly provide very good stability also for pH values above 4.

It has been reported that solutions containing citrate as buffering agent may be more prone to causing pain after subcutaneous injection than several other solutions containing physiologically acceptable buffers, such as solutions using for instance histidine as buffering agent. Usually the pain sensation is highest just after the subcutaneous administration, such as within a few minutes of administration, with the pain dissipating thereafter. Even so, pain caused by subcutaneous injection is an unpleasant condition, which may limit patient compliance.

In the invention, it was found that by using a low concentration (such as 30 to 70 mM, preferably 40 to 60 mM) citrate/phosphate buffering system, the positive effects of citrate are retained while any pain sensation after subcutaneous injection may be avoided or minimized.

The invention enables components which may adversely affect the stability of levodopa and/or carbidopa, be included in the buffering solution since such components will stay out of contact with levodopa and/or carbidopa until the stock and the buffering solutions are being mixed. This is another advantage of the invention, which opens up for the use a large variety of components that improve stability, reduce the formation of toxic metabolites etc.

Furthermore, adding another buffer component, such as low concentration phosphate, to the aqueous buffering solution already containing the buffer component citric acid (the term citrate may rather be used considering the high pH-value), while maintaining an acceptable osmolality of the final infusion solution, is highly advantageous. It increases the range of the buffering capacity covering the entire pH-range of the invention. Furthermore, and more importantly, it makes it possible to reach a higher pH-value of the buffering solution than if only citrate is included. The maximum pH-value of the buffering solution obtained was 6.2 only using citrate (the pKa-values of citrate being 3.13, 4.76 and 6.40). Also adding phosphate enabled the pH-value of the buffering solution reach 7.6 (the pKa-value of phosphate being 7.20) while still maintaining a good buffering capacity. Starting off with a higher pH-value enables the resulting infusion solution (after being mixed) reach a pH range of 5.1-5.4. The aforementioned is demonstrated by the experiments laid out in the experimental section. Such a pH range is optimal considering the absorption of the APIs in the tissue at subcutaneous infusion (as has previously been put forward in the description). Thus, in one embodiment, the buffer components used are both citric acid and phosphate.

In some embodiments, the aqueous buffering solution further comprises a solubilizer. The solubilizer may be selected from the group consisting of glutathione, cysteine, HP-beta-cyclodextrin, N-methyl pyrrolidone (NMP), dimethylacetamide (DMA), collidone, kolliphor HS 15, PEG 400, propylenglycol, polysorbate 80, glycerine, ethanol, cremophor EL, DMSO, methionine, EDTA, ascorbic acid, aspartic acid, benzalkonium chloride, benzyl benzoate, cetylpyridinium chloride, hydroxypropyl betadex, lecithin, macrogol 15 hydroxystearate, meglumine, phospholipids, poloxamer, polyoxyethylene alkyl ethers, polyoxyethylene castor oil derivative, polyoxyethylene sorbitan fatty acid esters, pyrrolidone, triolein, vitamin E polyethylene glycol succinate or mixtures of two or more of these. In one embodiment, the solubilizer is HP-beta-cyclodextrin. As can be seen in table 5, 6 and 16, HP-beta-cyclodextrin, having a concentration of about 75 mg/ml, improves physical stability.

Both the aqueous stock solution and the aqueous buffering solution may preferably contain stabilizers such as stabilizing agents, antioxidants and preservatives or a combination of those. Thus, in one embodiment, the aqueous buffering solution further comprises at least one stabilizer. In one further embodiment, the stabilizer is selected from a group containing stabilizing agents, antioxidants and preservatives or a combination of those.

The stabilizing agents may be selected from the group consisting of bentonite, calcium alginate, calcium stearate, carbidopa, such as carbidopa monohydrate, carboxymethyl cellulose calcium, ceratonia, cyclodextrins, dextran, diethanolamine, ethylene glycol palmitostearate, fructose, glyceryl monostearate, lecithin, macrogol 15 hydroxystearate, mannitol, monoethanolamine, propylene glycol, sodium acetate, sodium borate, sorbitol, sulfobutylether beta-cyclodextrin, trehalose, zinc acetate and the like.

In one embodiment, the stabilizing agent is a physiologically acceptable sugar. The physiologically acceptable sugar may be glucose. In one embodiment, a glucose concentration is in the range of 5 to 100 mg/ml. Further, the physiologically acceptable sugar may be fructose, dextran, e.g. dextran 70, 60, or 40, or mannitol.

Apart from its stabilizing effect of Levodopa, as shown in table 4, glucose may further be advantageous for its pain reduction effects during subcutaneous injection. Furthermore, there are indication that glucose may act as a mild procoagulant. It seems these effects are present already at a lower glucose concentration, such as from 5 to 100 mg/ml, which is advantageous, since the addition of glucose has been shown to increase carbidopa breakdown. These effects are especially advantageous when glucose is used together with a citrate or citrate/phosphate buffering system, since the addition of glucose may help reduce or alleviate possible pain or bruising after subcutaneous injection of solutions containing citrate. Thus, in one embodiment, the glucose concentration is from 5 to 100 mg/ml. In one embodiment, the pharmaceutical solution does not comprise glucose.

As shown in Table 15, glucose can have a destabilizing effect on carbidopa. Accordingly, in some embodiments, when carbidopa is present, the concentration of glucose is limited. Optionally, when carbidopa is present, the aqueous pharmaceutical solution does not comprise glucose.

The antioxidants may be selected from the group consisting of alpha tocopherol, ascorbic acid, ascorbyl palmitate, butylated hydroxyanisole, citric acid monohydrate, erythorbic acid, malic acid, methionine, monothioglycerol, pentetic acid, Potassium metabisulfite, propionic acid, sodium formaldehyde sulfoxylate, sodium metabisulfite, sodium sulfite, sodium thiosulfate and the like.

The preservatives may be selected from the group consisting of anhydrous, benzalkonium chloride, benzethonium chloride, benzoic acid, boric acid, bronopol, butylene glycol, calcium acetate, calcium lactate pentahydrate, cetrimide, cetylpyridinium chloride, chlorobutanol, chlorocresol, citric acid monohydrate, cresol, dextran, edetic acid, ethyl parahydroxybenzoate, glycerol, imidurea, methyl parahydroxybenzoate, monothioglycerol, phenol, phenoxyethanol, and phenylethyl alcohol.

Carbidopa may be used as a preferred stabilizer of levodopa in the stock solution where it has a double effect in that it also serves as an inhibitor.

Sodium metabisulfite is another preferred stabilizer that may be used in the stock solution where it improves the solubility and decreases the degradation of the APIs and the build of toxic by-products. Sodium metabisulfite (also known as sodium pyrosulfite) is an inorganic compound of chemical formula $Na_2S_2O_5$. Sodium metabisulfite oxidizes in the liver to sulfate which is excreted in the urine, whereby tens of milligrams can be taken as a daily dose without causing adverse effects.

By using on-line mixing the infusion solution may fulfil the demands of a pharmaceutical product as long as the degradation of the APIs are within stipulated limits after less than 90 minutes, such as less than 50, 20, 10 or 1 minutes from the point of time the solutions are being mixed up to the point of time the solution is infused into the patient's tissue. This stable window of supersaturation allows for the use of higher levodopa concentrations, thus reducing the infusion volumes.

In one preferred embodiment, the aqueous pharmaceutical solution is provided by mixing of I) and II), wherein I) is an aqueous stock solution, having of pH of less than 2.8 at 25° C. comprising; a) aqua sterile, b) levodopa, c) at least one enzyme inhibitor, d) at least one physiologically acceptable acid, e) at least one physiologically acceptable stabilizer, wherein the stock solution is bubbled with nitrogen after mixing. II) is an aqueous buffering solution, having a pH of at least 4.0 at 25° C., comprising; f) aqua sterile, g) at least one physiologically acceptable buffer component, h) at least one physiologically acceptable stabilizer and/or solubilizer. The aqueous pharmaceutical solution may be oversaturated and administered to a subject suffering from a disease of the central nervous system (CNS) within 24 hours, such as within 16 hours, 12 hours, 6 hours, 4 hours, 2 hours, 1 hour, 30 minutes, 20 minutes, 10 minutes, 5 minutes or 1 minute, from mixing the aqueous stock solution and the aqueous buffering solution.

An example of such a specific composition comprising 10 mg/ml levodopa and 1.25 mg/ml (1:8) carbidopa, is prepared by mixing I) and II), wherein I) is an aqueous stock solution of 1000 ml containing a) 963 g purified water, b) 43.3 g 5 M HCl, where the solution is purged with nitrogen, c) 20 g micronized levodopa, d) 2.71 g carbidopa monohydrate (equivalent to 2.5 g carbidopa), where the solution is once more purged with nitrogen. II) is an aqueous buffering solution containing e) 968 g purified water, f) 64.7 g tri-sodium citrate dihydratedihydrate, g) 3.56 g di-sodium hydrogen phosphate dihydrate, h) 3.67 g 1M HCl.

In more detail, this composition is prepared using the following components, steps and methods: A 20 mg/ml levodopa and 2.5 mg/ml carbidopa stock solution of 1000 ml was prepared as follows: 963 g water was poured into a Duran bottle equipped with a magnetic stirrer, whereupon, 43.3 g 5 M hydrochloric acid (HCl) was added, whereupon, the solution was purged with nitrogen until the residual oxygen content was <0.1 ppm, whereupon, 20 g micronized levodopa was added, whereupon, 2.71 g carbidopa monohydrate (equivalent to 2.5 g carbidopa) was added. The resulting solution was stirred, using the magnetic stirrer, until all substances were dissolved in the solution. The pH was measured to approximately 1. The solution was again purged with nitrogen until the residual oxygen content was <0.1 ppm. A buffering solution was prepared as follows: 968 g water was poured Into a Duran bottle equipped with a magnetic stirrer, whereupon, 64.7 g tri-sodium citrate dihydrate was added, whereupon, 3.56 g di-sodium hydrogen phosphate dihydrate was added, whereupon, 3.67 g 1M hydrochloric acid HCl was added, whereupon, the solution was stirred, using the magnetic stirrer, until all material was dissolved. The pH was measured and adjusted to 7.6 using 1 M HCl (in the event the solution was too basic) and 1M sodium hydroxide (NaOH) (in the event the solution was too acidic).

In Pedro Chana et.al., a study of carbidopa stability is presented. The study confirmed that carbidopa in solution is an unstable compound and degrades naturally over a short period. No environmental factor studied reduced degradation and maintained stability over 24 h, and a near-50% degradation profile of carbidopa in a levodopa and carbidopa aqueous solution over 24 h was observed. The degradation of the APIs—from the point of time the pharmaceutical product is produced up to the time it is administered to the patient—must stay within given limits. Often the degradation of the concentration of each API must be lower than 10% of its original value, preferably substantially lower. As such, API degradation if far from only being a shelf-life problem, but may in fact represent a regulatory hinder for registration as a pharmaceutical product. In fact, several promising levodopa and carbidopa solutions in the art may in effect not be possible to register as pharmaceutical products.

Carbidopa degrades into toxic by-products such as hydrazine and 3,4-dihydroxyphenylacetone (DHPA). Table 7, presents the chemical degradation of levodopa and carbidopa over time. In other experiments, such as those summarized in table 15, the short term physical stability, the degradation of levodopa and carbidopa and the build-up of DHPA are presented.

In one embodiment, the degradation of levodopa in the aqueous pharmaceutical solution is less than 15% after 1 minute, such as after 5, 10, 15, 20, 30, 40, 50, 60, or 90 minutes after the stock solution and the aqueous buffering solution have been mixed.

In one further embodiment, the aqueous pharmaceutical solution comprises carbidopa, wherein the degradation of carbidopa is less than 15% after 1 minute such as after 5, 10, 20, 30, 40, 50, 60, or 90 minutes from the point of time the stock solution and the aqueous buffering solution are being mixed.

In certain embodiments, the degradation of levodopa in the aqueous pharmaceutical solution is less than 15% up to 24 hours, such as up to 16, 8, 6, 4, 3 or 2 hours from the point of time the stock solution and the aqueous buffering solution have been mixed.

In one further embodiment, the aqueous pharmaceutical solution comprises carbidopa, wherein the degradation of carbidopa is less than 15% up to 24 hours, such as up to 16, 8, 6, 4, 3 or 2 hours from the point of time the stock solution and the aqueous buffering solution are being mixed.

In one embodiment, the aqueous pharmaceutical solution comprises carbidopa, wherein the aqueous pharmaceutical solution is administered before 15 wt %, such as before 10 wt %, of the carbidopa in the aqueous pharmaceutical solution has degraded.

In one embodiment, the aqueous pharmaceutical solution comprises carbidopa and the time from mixing of the aqueous stock solution and the aqueous buffering solution to administering the aqueous pharmaceutical solution to a subject suffering from a disease of the central nervous system (CNS), is shorter than the time from mixing until 15 wt %, such as 10 wt %, of the levodopa or carbidopa in the aqueous pharmaceutical solution has degraded.

In one further embodiment, the level of DHPA (3,4-dihydroxyphenylacetone) is less than 5 mg % of carbidopa (CD), and the level of hydrazine is less than 1 mg % of carbidopa (CD) after 1 minute, such as after 5, 10, 20, 30, 40, 50, or 60 minutes from the point of time the stock solution and the aqueous buffering solution have been mixed.

Levodopa is primarily used for treatment of Parkinson's disease. However, also other dopamine related disorders have been treated using levodopa, such as restless leg syndrome. In one embodiment, the CNS disease is selected from the group consisting of Parkinson's disease, Atypical Parkinsonism, Alzheimer's disease, Restless Legs Syndrome (RLS) and the group of neurological mental illnesses; preferably the CNS disease is Parkinson's disease.

In one further embodiment, the CNS disease is Parkinson's disease in complication phase. The solution may also be beneficial for other disorders, such as other movement disorders (dystonia, progressive supranuclear palsy [PSP], neuroleptic malignant syndrome [NMS], primary psychiatric disorders (schizophrenia, mood disorders, personality disorders), endocrine disorders (diabetes mellitus, essential obesity, hypopituitarism), hepatic disease (alcoholic cirrhosis, steatohepatitis, hepatic encephalopathy), cardiovascular diseases and asthma.

As described above, the unique properties of the aqueous pharmaceutical solution, such as the physiologically acceptable pH range and the high levodopa concentration, makes it suitable for use as a pharmaceutical infusion or injection solution. Although there may be advantages injecting a large amount of solution during a short time span to quickly reach a high therapeutic level of levodopa, the best treatment effect is reached using continuous administration, since this has been shown to prevent several of the side effects of prolonged levodopa use.

Subcutaneous infusion is a suitable administrative route in that it is a well-proven technique and known to be highly effective for medications (such as insulin and morphine) that require administration by low infusion rates. The subcutaneous tissue has few blood vessels, resulting in a slow, sustained rate of absorption. Thus, in one embodiment, the aqueous pharmaceutical solution is a pharmaceutical infusion or injection solution, and in one further embodiment, the solution is for continuous administration. In one further embodiment, the solution is for parenteral administration. In one further embodiment, the parenteral administration is subcutaneous, intravenous, intra-arterial, intraosseous, intramuscular, intracerebral, intracerebroventricular, or intrathecal administration, the administration mode being injection or infusion. The parenteral administration may be subcutaneous administration. Optionally, the parenteral administration is intravenous administration. In one embodiment, the parenteral administration is continuous for up to 24 hours, such as 0.1 to 4 hours, such as 4 to 6 hours, such as 6 to 8 hours, such as 8 to 12 hours, such as 12 to 16 hours and such as 16 to 20 hours. In one embodiment, the solution is intended for injection.

As described above, infusion solutions described in patent JP 54105221 and in patent application WO 2012/066538 A1 all have pH-values in the range of 9 to 10. They are thus not suitable for continuous parenteral administration. Clinical studies conducted on the product described in WO 2012/066538 A1 show that therapeutic levels of levodopa in the plasma (on patients suffering from PD in complication phase)) are not reached until 6 to 8 hours after the treatment started. As opposed to this, pharmacokinetic studies performed on PD-patients in complication phase, using the present invention, suggest that therapeutic levels of levodopa may be reached within less than an hour from the point of time the administration commences. Several factors may contribute to this, but the pH range of the solution of the invention is likely to increase the rate of absorption and the clinical effect of levodopa. In one embodiment of the invention, a therapeutic level is reached, when treating on-off symptoms on patients suffering from Parkinson's disease in complication phase, within less than 3 hours, such as within 2 hours, 1 hour, 50 minutes, 40 minutes, 30 minutes, 20 minutes or 10 minutes from the point of time the administration commences.

Figure 12A:
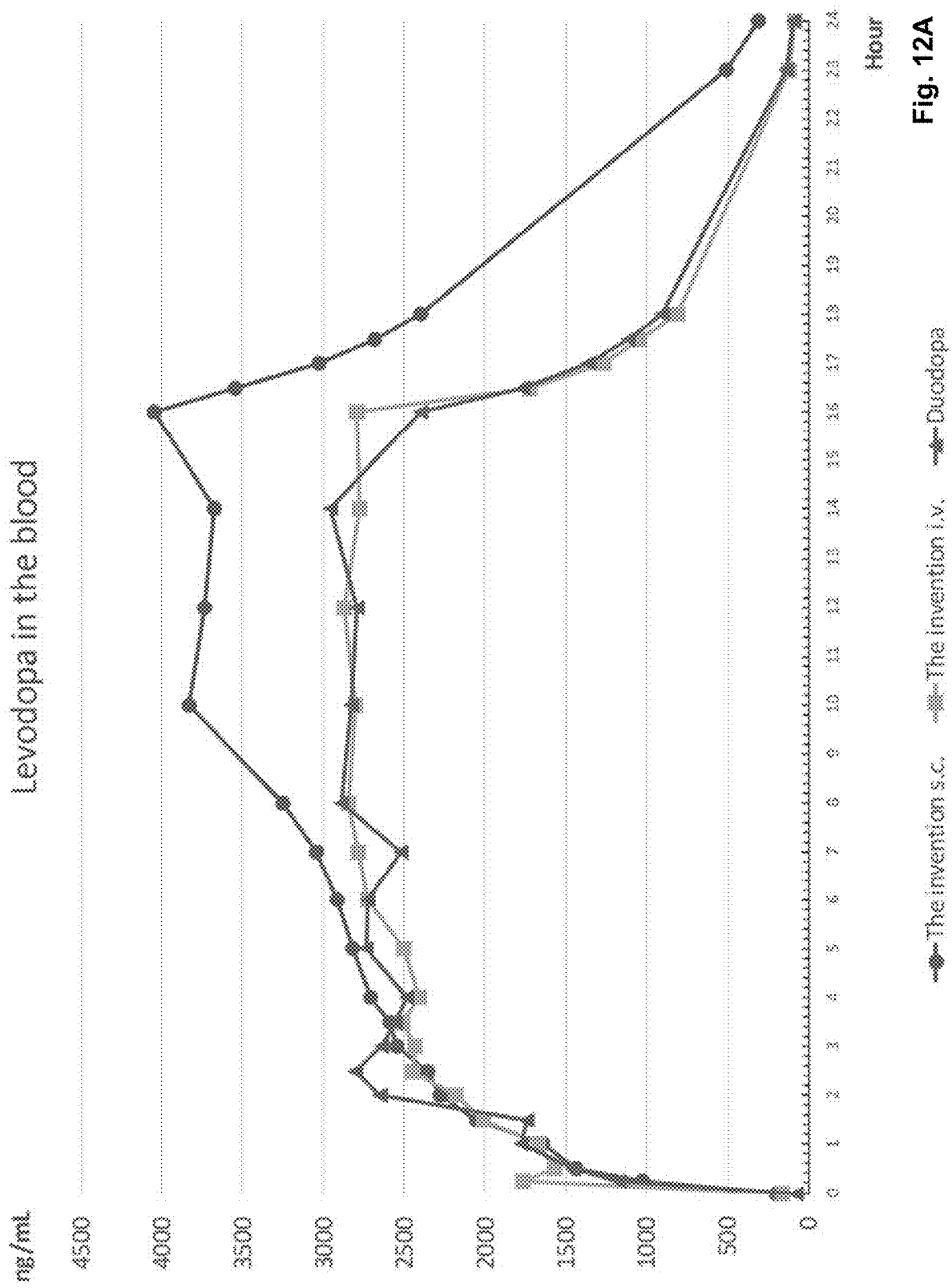
FIG. 12, which shows summarized results from clinical trial interim studies, where blood levels of (a) Levodopa and (b) Carbidopa are monitored in the patients' blood during administration and plotted against treatment time.
Figure 12B:
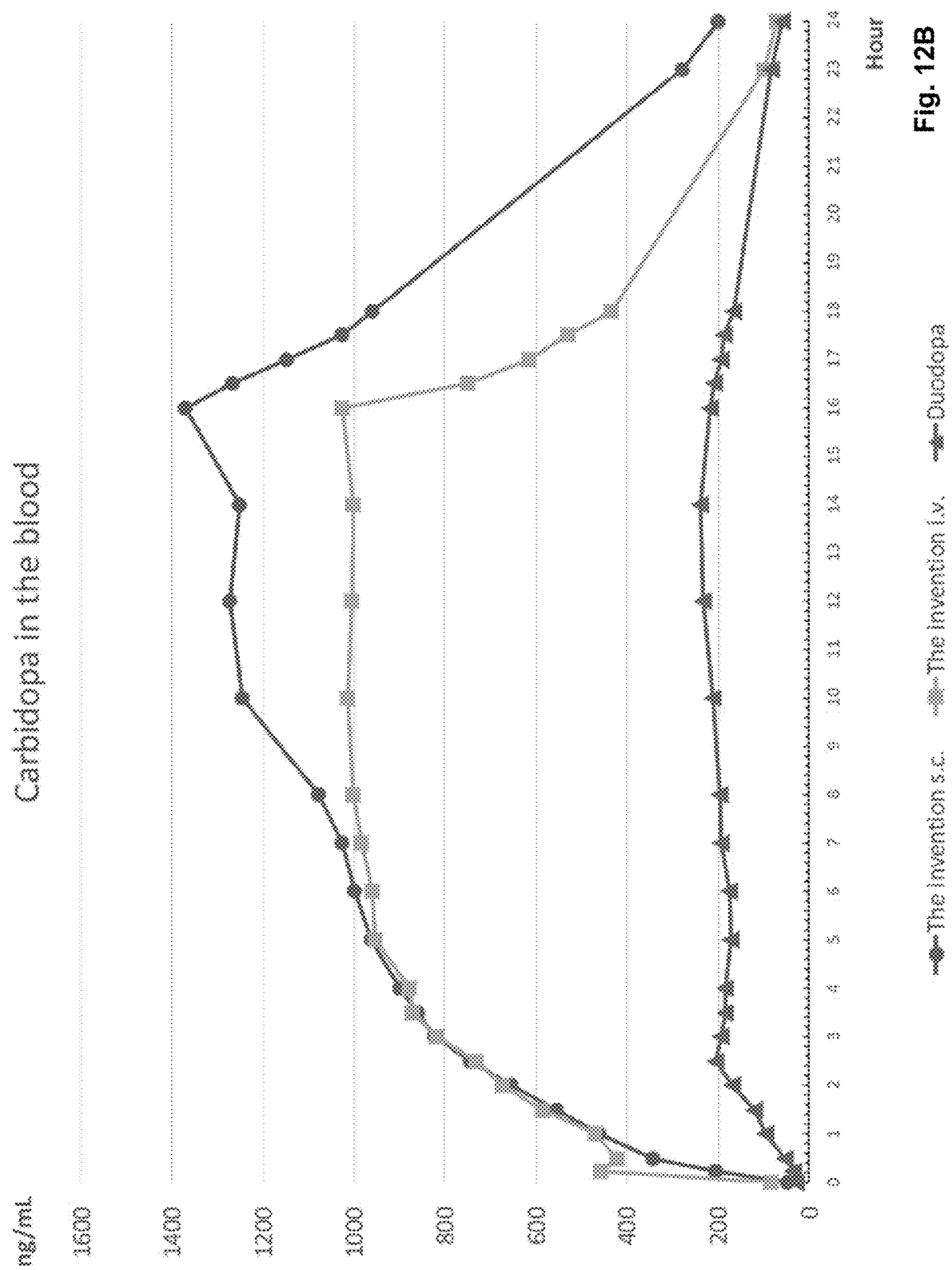
Figure 13:
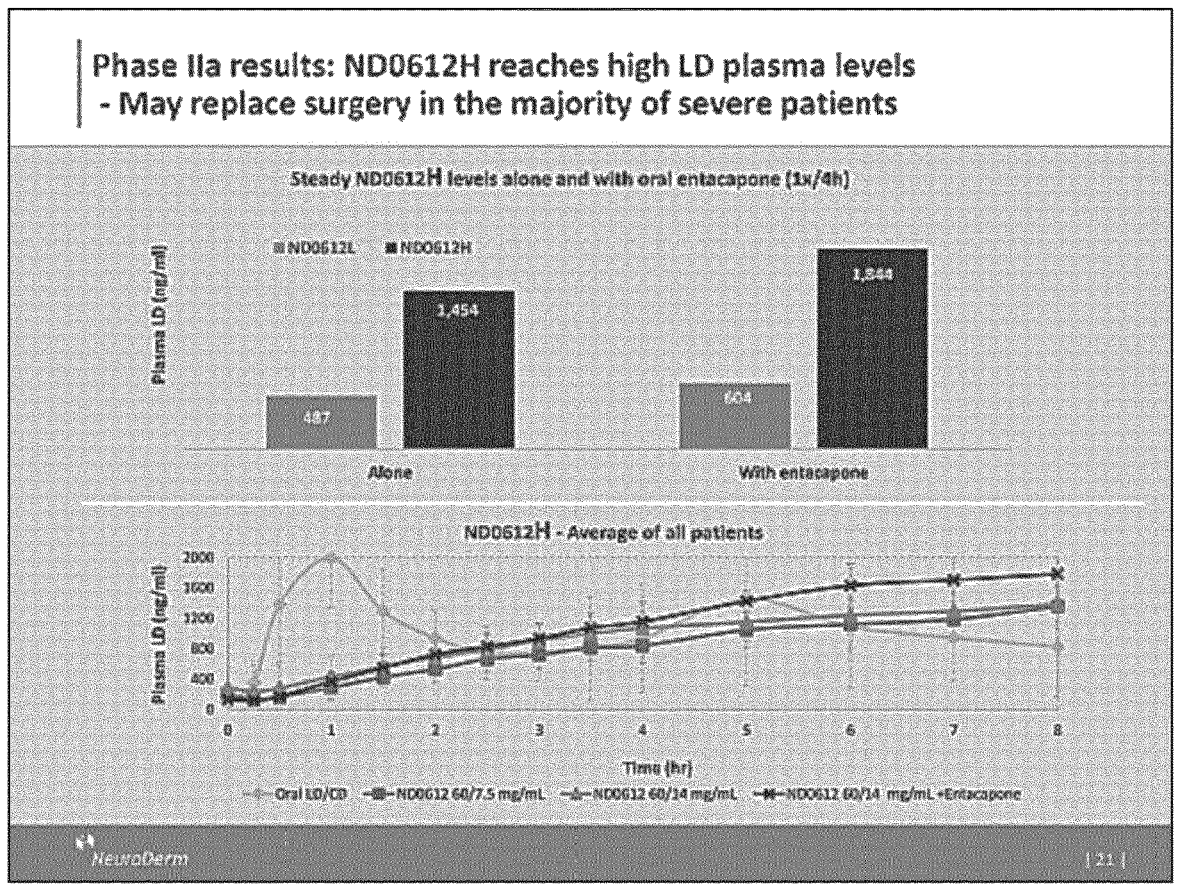
FIG. 13, which shows results from a clinical trial where a levodopa-carbidopa solution intended for continuous subcutaneous infusion is used and where the pH of the infusion solution is above 9. Blood levels of levodopa is monitored in the patients' blood during administration and plotted against treatment time.

Furthermore, the rapid response to the invention enables the levodopa plasma concentrations to be adjusted (by changing the infusion rate) to meet the short-term variations in levodopa need of different PD patients. In one further embodiment of the invention, the plasma level of levodopa may be adjusted, by adjusting the infusions rate, within a time period short enough to minimize on-off symptoms of individual patients for which the levodopa need varies. In FIGS. 12 and 13, the average blood and plasma levels of levodopa and carbidopa three patients are shown. As can be seen, the solution of the invention is able to rapidly reach and maintain the desired therapeutic level.

Other routes of administration are also possible, such as using the solution of the invention for administration to the duodenum. However, as pointed out earlier, administration via the duodenum typically requires a probe through the abdominal wall. In one embodiment, the aqueous pharmaceutical solution is intended for enteral administration, preferably duodenal administration.

The fact that the formulations of the invention allow for instant mixing of the stock- and the buffering solutions enables an "on line" administration system be used. In table 21, results are summarized for on line mixing experiments using solutions of the invention and an on line mixing system. The degradation of the APIs and the levels of DHPA are well within stipulated limits even long after the stock- and the buffering-solutions have been mixed.

In a further embodiment, a kit for providing the aqueous pharmaceutical solution for use in the treatment of diseases of the central nervous system (CNS) is provided. As already outlined, the aqueous pharmaceutical solution comprises at least 5 mg/ml dissolved levodopa, and has a pH in the range of 3.0 to 8.5. In some embodiments, the kit comprises:

(a) An aqueous stock solution comprising levodopa, said aqueous stock solution having a pH of less than 2.8 at 25° C.;

(b) An aqueous buffering solution, for increasing the pH of said aqueous stock solution, comprising a buffer component and having a pH of at least 4.0 at 25° C.

In some embodiments, the kit comprises:

(a) An aqueous stock solution comprising levodopa, said stock solution having a pH of greater than or equal to 8.0 at 25° C.; and (b) An aqueous buffering solution, for decreasing the pH of said stock solution, comprising a buffer component and having a pH of no more than 6.0 at 25° C.

The aqueous stock solution of the kit may be any of the aqueous stock solutions disclosed herein. The aqueous buffering solution may be any of the aqueous buffering solutions disclosed herein.

In some embodiments, any of the above kits further comprises:

(c) Mixing means 1 for mixing said solutions a) and b); and (d) output means 2 for transporting said mixed solution of step c).

The output means may be a connector, such as a coupling or adapter. For administration, the output means may comprise or be connected to an injection or infusion means 20, such as a syringe needle. The needle may be made of plastic, to minimize chemical reactions between the needle material and the mixed aqueous pharmaceutical solution and/or increase the comfort of the patient during administration of the mixed aqueous pharmaceutical solution.

The aqueous pharmaceutical solution may be a pharmaceutical infusion or injection solution. The injection or infusion means are thus selected for the mode of administration. The aqueous pharmaceutical solution may be for continuous administration. It may be for parenteral administration. In one further embodiment, the aqueous pharmaceutical parenteral administration is subcutaneous, intravenous, intra-arterial, intraosseous, intra-muscular, intracerebral, intracerebroventricular, or intrathecal administration, the administration mode being injection or infusion. In some embodiments, the parenteral administration is subcutaneous administration. The parenteral administration may as well be intravenous administration.

In one embodiment, the kit is for use in the treatment of diseases of the central nervous system (CNS).

Figure 11A:
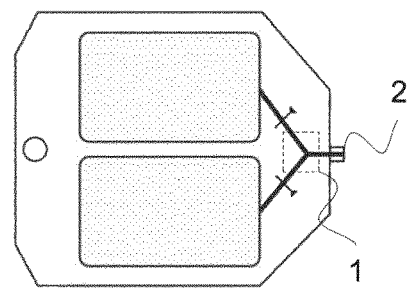
FIG. 11, which shows a schematic illustration of a kit, wherein the kit is gravity fed (11A), comprises one pump (11B) or two pumps (11C) and in 11D examples of suitable mixing means are shown.

The compartments for the stock and buffering solutions may be pressed as two parts in one bag (as seen in FIG. 11A), or being separate. By hanging the bag, the solution may be gravity fed through the mixing means 1 to the output means 2. Using hermetically sealed compartments, sterility, ease of use, improved control and lower total costs may be obtained. A flow regulator, such as a roller clamp, may also be used to control the flow rate.

Figure 14B:
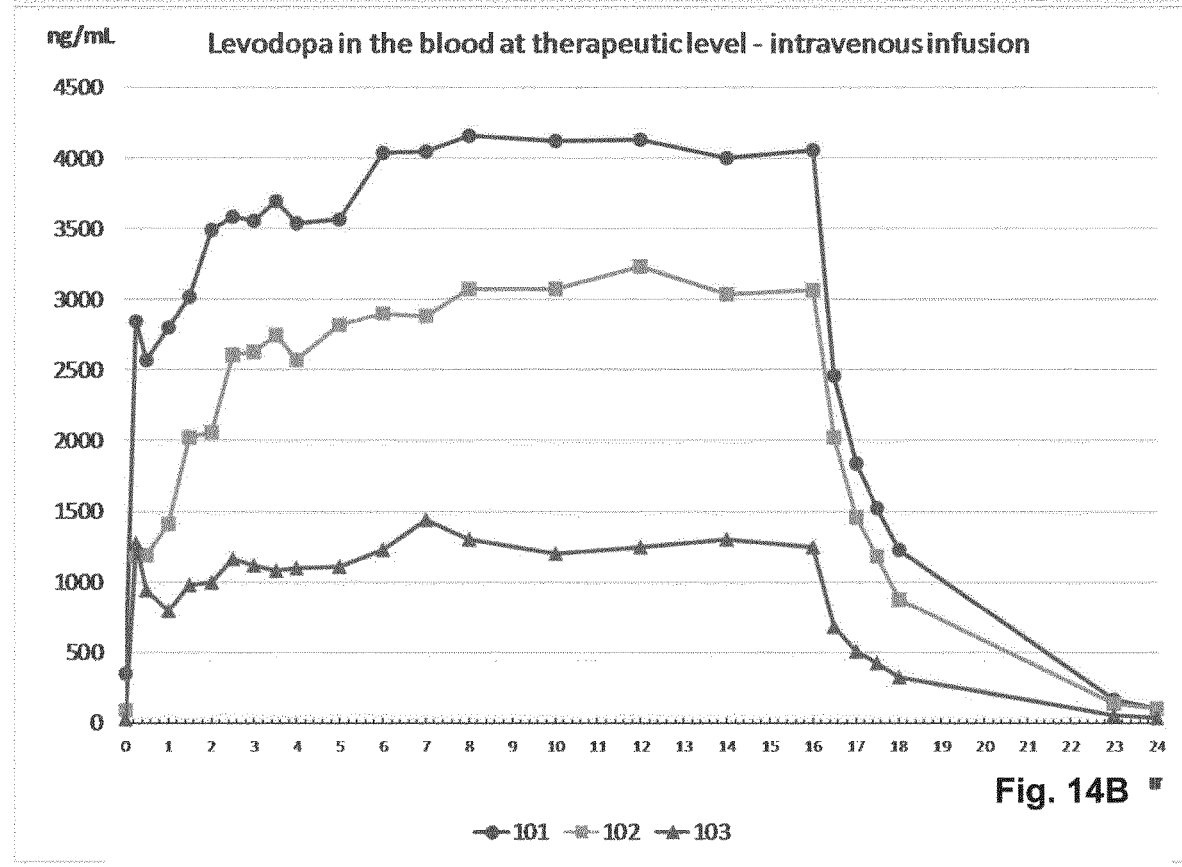
Figure 15:
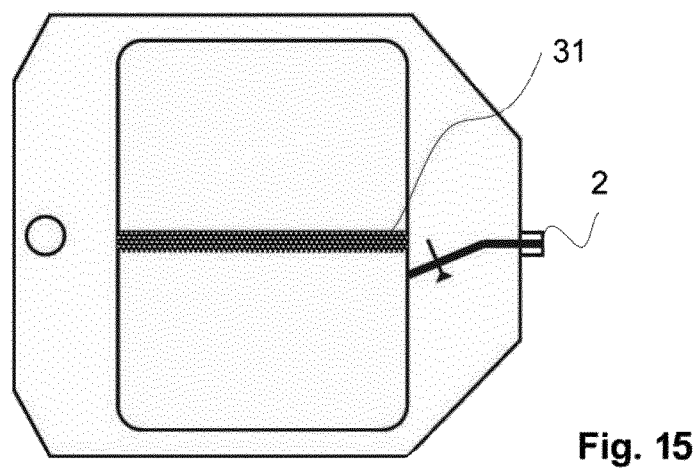
FIG. 15, which shows a schematic illustration of a bag with compartments for the stock and buffering solutions pressed as two parts in one bag separated by a perforable barrier.

According to an alternative simplified version of the embodiment, the aqueous stock and aqueous buffering solutions may be pressed as two parts in one bag with a removable or temporary barrier between the two parts. For instance, as can be seen in FIG. 14, the two parts may be separated by a perforable barrier 31, which can be removed by pressing the two parts together, resulting in a bag comprising only one part containing the two solutions intermixed, and an output means 2. If so, the mixing is facilitated by pushing the bag, which moves the solutions around in the bag, allowing the stock and buffering solutions to mix. Such an embodiment is possible due to the fact that the stock and buffering solutions allow for a simple mixing procedure. Administration may then be facilitated by a single pump (or possibly gravity fed) to the patient within the time limit for the solution. The resulting solution could also be injected directly as a bolus injection. This simplified embodiment may however not be optimal for metastable, such as supersaturated solutions. Further, the time form mixing to administration is prolonged. Still, such a simplified embodiment may be acceptable in some clinical settings.

Figure 11B:
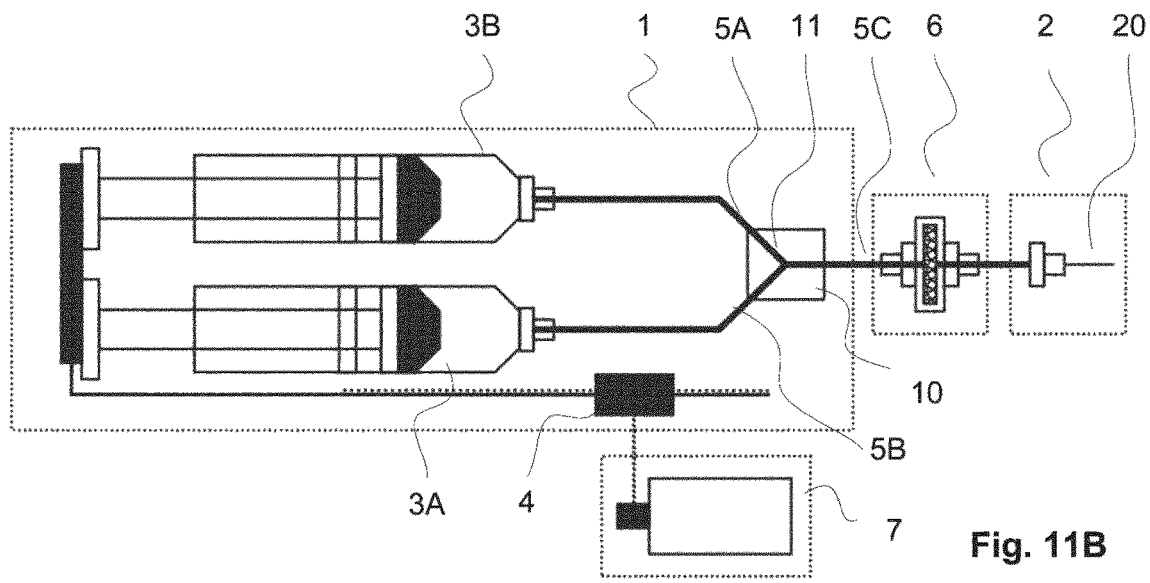
Figure 11C:
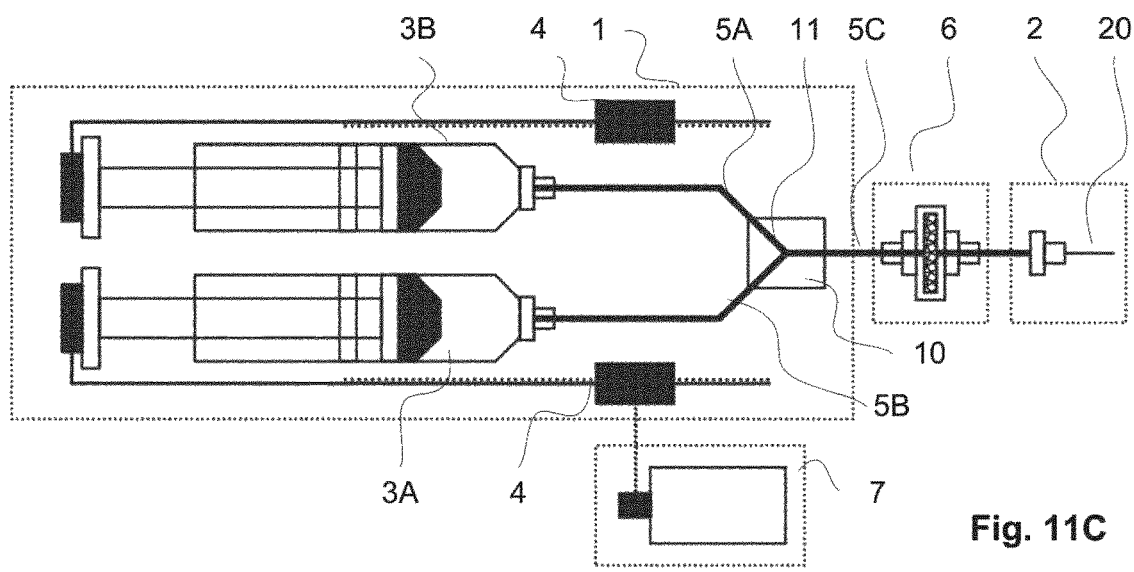
Figure 11D:
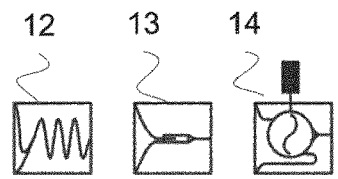

Using a pump allows for precise control over the flow rate and total amount delivered. According to one embodiment, a pump 4 is used for transporting the solutions to and through mixing means to the output means. A schematic illustration of such a system is shown in FIG. 11B. In such a kit, the mixing means comprises two compartments 3A, 3B, a pump 4, and a mixing chamber 10, wherein a first compartment 3A contains the aqueous stock solution and a second compartment 3B contains the aqueous buffering solution. A pump 4 is arranged to transport the solutions from the compartments 3A, 3B to the mixing chamber 10. The mixing chamber 10 is arranged to provide for mixing of the received aqueous stock solution and the received aqueous buffering solution, and wherein the pump 4 further is arranged for transporting the mixed aqueous pharmaceutical solutions from the mixing chamber to the output means 2.

The mixing means 1 may comprise two pumps 4, the first pump 4 being connected to the first compartment 3A and the second pump 4 being connected to the second compartment 3B. This allows for precise control of the flow rate and the total amount delivered by each pump, enabling the use of different mixing ratios of the stock solution and the buffering solution. Since a buffering system is used, the pH of the mixed solution will change very slowly from the buffer equilibrium point, as long as the buffer has buffering capacity. In one embodiment, the stock solution to buffering solution ratio is from 10:1 to 1:10, such as from 5:1 to 1:5, such as from 2:1 to 1:2, such as 1:1.

Any pump suitable for controlled infusion may be used. It includes any suitable system for moving fluids, such as systems using vacuum or osmotic power. In one embodiment, the pump 4 is a syringe pump, a volumetric pump, a peristaltic pump, or an ambulatory pump.

In one embodiment, the kit further comprises tubing 5A, 5B, 5C. The solution compartments 3A, 3B may by connected to the mixing chamber 10 by a first 5A and second 5B tubing, and the mixing chamber may be connected to the output means 2 by a third tubing 5C. Experiments performed verified that non-transparent tubing and/or compartments may limit the degradation of levodopa and/or carbidopa. This suggests that degradation reactions may be photo-induced to some extent. The containers 3A, 3B and/or tubing 5A, 5B, 5C may be non-transparent or UV-absorbing.

In certain designs, such as when the whole mixing means 1 is located on a card or chip, the mixing chamber 10 may be connected directly, without using tubing, to the compartments 3A, 3B containing the aqueous stock solution and the aqueous buffering solution. Similarly, the mixing means 1 may be connected directly, without using tubing, to the output means 2. This may also be the case if the mixing means are integrated in a bag, such as shown in FIG. 11A.

Several different kinds of mixing chambers 10 exist or may be developed, including Y-connectors 11 combining two solutions to one at a junction, to channels with a shape which actively mixes the solutions. Thus, in one embodiment, the mixing chamber 10 is a 2-way Y-connector 11. In one further embodiment, the 2-way Y-connector 11 is a "Y'-Connector set 2 way". An example of such a connector that can be used in an on-line system is the 2-way Y-connector 11 by Becton, Dickinson and Company, or a similar device.

In some embodiment, the mixing of the stock solution and the buffering solution may—under specific conditions—be made in a mixing means constituted by an y-coupling with a mixing chamber to which the stock solution and the buffering solution are led via two plastic tubes fed by two pumps (or preferably one pump provided with two containers and two pistons operated by one electric motor) containing the stock solution and the buffering solution respectively, from which the mixed resulting infusion solution is led to the infusion site via a plastic tube. The mixed resulting solution may be unstable, which may be a result of the mixed solution being oversaturated, at levodopa concentration being close to or above 10 mg/ml and the APIs precipitate. Special measures may be introduced comprising optimization of formulations, methods and devices.

Specific embodiments may thus include:
1. The stock solution containing the APIs being bubbled with nitrogen during production.
2. The flow rate of the infusion solution being limited (typically 1.4-10.0 mL/h) where too low a flow rate may result in immediate precipitation.
3. The plastic tubes being protected from UV-light.
4. The y-coupling being provided with a mixing chamber, where the size of the mixing chamber needs to be optimized given the composition of the stock solution and the buffering solution and the flow rate.
5. The total length of the plastic tubes being optimized considering the following parameters:
    The length of the plastic tube (1)—from the output of the mixing means to the infusion needle—expressed in mm should preferably not exceed:
    $l = (L \times 200 \times t) / (D^2 \times \pi \times 3 \times c \times h)$, where,
    L=The maximum amount of levodopa required during a day by a group of patients, expressed in mg
    t=The maximum time, which may be allowed from mixing till infusion in view of the permitted degradation of the APIs, expressed in seconds
    D=The diameter of the plastic tubes, expressed in mm
    c=The concentration of levodopa expressed in mg/mL
    h=The daily time of treatment for the patient group concerned Mixing can also be actively promoted by moving the fluids through certain channel shapes, such as spiral formed channels through which the mixed aqueous pharmaceutical solution is led whereby the mixing is enhanced due to the centrifugal forces applied on the solution when transported through the channel. In one embodiment, the mixing chamber 10 is constituted by/contains a spiral formed channel 12 for mixing the two solutions. Other shapes may be a venturi mixer 13, i.e. a channel using a constricted section to cause a venturi effect to facilitate mixing. Mixing may also utilize an active mixing tool. In one embodiment, the mixing chamber 10 contains a motorized mixing tool 14 such as a piston, a screw, a propeller or a similar device. Mixing means are graphically summarized in FIGS. 11A-D.

To facilitate easy use of the kit, the stock- and buffering solutions require suitable storage containers. Typically, medical solutions for infusion are stored in a closed system to prevent the contained solution from contact with the atmosphere. Preferably, the solution container also must be able to endure autoclave sterilization for the contained solution. In one embodiment of the invention, the containers are syringes, bags, bottles or cassettes.

A solution suitable for parenteral administration must not contain contaminants, such as particles from crystallization or precipitation. Therefore, it is advantageous to filter the infusion solution prior to the administration. There are several different filter types known in the art, such as microbiological filter or particle filters that may be used. In one embodiment, the kit further comprises a filter 6, such as a microbiological filter or a particle filter, for filtering the solution before parenteral administration. The filter 6 is arranged downstream the mixing chamber 1.

To facilitate increased mobility for a patient using a kit, it is advantageous to provide a kit of a convenient size. Either the kit can have solution compartments 3A, 3B of a volume that allows a full day continuous use. Alternatively, solution compartments 3A, 3B could be relatively small and replaced throughout the day. Thus, in one embodiment, the volume of the containers is sufficient to enable a subject suffering from a disease of the central nervous system (CNS) be treated continuously for at least 4 hours, such as 4 to 6 hours, such as 6 to 10 hours, such as 10 to 16 hours, such as 16 to 24 hours. In one embodiment, the compartments 3A, 3B can be replaced or refilled, preferably replaced. In one further embodiment, the compartments 3A, 3B can be refilled or replaced even during continuous administration. In one embodiment, the volume of the containers is 10 to 1000 ml per container, such as 50 to 500 ml per container, such as 100 to 250 ml per container.

Using replaceable compartments 3A, 3B, the treatment could be continuous for as long as the compartments 3A, 3B are replaced when emptied. In one embodiment, the compartments 3A, 3B can be replaced by new compartments 3A, 3B twice, 3 times, 4 times, 5 times or 6 times during a 24 hours period, enabling a subject to be treated continuously for 24 hours. In one embodiment, the required time period for replacing compartments 3A, 3B is less than 10 minutes such as 8 minutes, 6 minutes, 3 minutes or 1 minute.

To allow for flexibility, a kit may comprise a controlling means 7. This may simply be an on/off control for pumps 4, but it may also facilitate control of the infusion speed, and may control of the composition of the mixed solution through varying the stock to buffering solution ratio. Thus, in one embodiment, the kit further comprises control means 7, to control the flow speed of the pump(s) 4. Thus, one can control the infusion speed, the infusion duration and/or, in the case of when two pumps 4 are used, to change the stock solution to buffer solution ratio. In one further embodiment, the kit further contains a battery, to power active components, such as pump(s) 4, mixing chamber 10 and/or controlling means 7. The control means 7 can also include safety features to avoid hazards such as uncontrolled flow (causing an overdose), uncontrolled lack of flow (causing an under dose), reverse flow (can siphon blood from a patient), and air in the line (can cause an air embolism). Furthermore, the pump 4 and/or control means 7 preferably has no single point of failure, that is no single cause of failure should cause the pump to silently fail to operate correctly without triggering an (audible) error indication. The control means 7 may also store an internal electronic log of the therapy events.

To enable easy use of the kit at any location, the kit may also comprise other components that are helpful during use. In one embodiment, the kit further comprises a pair of surgical gloves, cleaning wipes, a disinfectant. In one further embodiment, the kit comprises a manual.

According to the invention, a set for providing an aqueous pharmaceutical solution, is also provided. In some embodiments, the set comprises: An aqueous stock solution, having of pH of less than 2.8 at 25° C. The stock solution comprises aqua sterile, levodopa, at least one enzyme inhibitor, at least one physiologically acceptable acid, and at least one a stabilizer. The stock solution is preferably bubbled with nitrogen after the being prepared. The set further comprises an aqueous buffering solution, having a pH of at least 4.0 at 25° C. The aqueous buffering solution comprises: aqua sterile, at least one buffer component, and at least one stabilizer and/or solubilizer.

In further embodiments, the set may comprise any of the previously described stock solutions and buffering solutionsor features of these solutions. According to an embodiment the invention relates to a method of continuously preparing an aqueous pharmaceutical solution for use in the treatment of diseases of the central nervous system (CNS), the aqueous pharmaceutical solution being suitable for continuous parenteral or enteral administration. The method comprises: continuously mixing a flow of a stock solution comprising levodopa, said stock solution having a pH of less than 2.8 at 25° C. and a flow of an aqueous buffering solution, said buffering solution having a pH of at least 4.0 at 25° C., thereby continuously obtaining from said mixing a continuous flow of an aqueous pharmaceutical solution. The aqueous pharmaceutical solution comprises at least 5 mg/ml dissolved levodopa, such as at least 6, 7, 8, 9, 10, 15, or 20 mg/ml dissolved levodopa; preferably the concentration of levodopa being in the range of 5 to 20 mg/ml dissolved levodopa, such as in the range 5 to 15 mg/ml or 5 to 10 mg/ml dissolved levodopa.

The fact that the formulations are prepared continuously enables an "on line" administration approach in the invention, wherein the specified stock and buffering solutions may be continuously mixed and the resulting infusion solution may be continuously administered. This is especially favourable for continuous subcutaneous infusion, where the infusion solution may be continuously mixed, providing a completely fresh infusion solution, during the course of the slow continuous infusion. Due to the continuous preparation followed by rapid online administration, any degradation of APIs will be well within the limits for pharmaceutical regulations.

In further embodiments, the method of continuously preparing an aqueous pharmaceutical solution for use in the treatment of diseases of the central nervous system (CNS) may comprise any of the previously described aqueous pharmaceutical solutions, stock solutions and buffering solutions, or any features of these solutions. Preferred aspects of the various solutions have been discussed herein above.

According to an embodiment, the invention relates to a method of treating diseases of the central nervous system (CNS). In some embodiments, the method comprises; continuously mixing a flow of a stock solution comprising levodopa, said stock solution having a pH of less than 2.8 at 25° C., and a flow of an aqueous buffering solution, said buffering solution having a pH of at least 4.0 at 25° C.; continuously obtaining from said mixing a continuous flow of an aqueous pharmaceutical solution comprising at least 5 mg/ml dissolved levodopa, such as at least 6, 7, 8, 9, 10, 15, or 20 mg/ml dissolved levodopa; preferably the concentration of levodopa being in the range of 5 to 20 mg/ml dissolved levodopa, such as in the range 5 to 15 mg/ml or 5 to 10 mg/ml dissolved levodopa; and continuously administering to a subject suffering from a disease of the central nervous system (CNS) the obtained aqueous pharmaceutical solution.

Further features, aspects and embodiments of the method of treating diseases of the central nervous system (CNS) have already been described herein in relation to other embodiments, e.g. the use of the aqueous pharmaceutical solution in treating diseases of the central nervous system (CNS), and such features, aspects and embodiments are equally applicable in relation to the method treating diseases of the central nervous system (CNS).

Evidently, compounds and pharmaceutical compositions disclosed herein may be used for the manufacture of a medicament for use in such treatment and prevention as disclosed herein. One such embodiment relates to the use of an aqueous pharmaceutical solution according to the invention for the manufacture of medicament for use in treating diseases of the central nervous system (CNS). The medicament is to be administered to the patient in accordance with previous embodiments.

Similarly, compounds and compositions disclosed herein may obviously also be used in method for treating or preventing such diseases and disorders as have been disclosed herein. Such a method includes the step of administering an effective amount of the compound, or the pharmaceutical composition, to a subject in need for such treatment.

Some further numbered embodiments of the invention relate to:

1. An aqueous pharmaceutical solution for use in the treatment of diseases of the central nervous system (CNS), the aqueous pharmaceutical solution comprising,
at least 5 mg/ml dissolved levodopa, and having a pH in the range of 3.0 to 8.5, wherein said solution is provided by mixing;
   a) the aqueous stock solution comprising levodopa, and said stock solution having a pH of less than 2.8 at 25° C.; and
   b) an aqueous buffering solution, for increasing the pH of said stock solution, comprising at least one buffer component, said buffering solution having a pH of at least 4.0 at 25° C.,
wherein the aqueous pharmaceutical solution is administered to a subject suffering from a disease of the central nervous system (CNS) within 24 hours, such as within 16 hours, 12 hours, 6 hours, 4 hours, 2 hours, 1 hour, 30 minutes, 20 minutes, 10 minutes, 5 minutes or 1 minute, from mixing the aqueous stock solution and the aqueous buffering solution.

2. The aqueous pharmaceutical solution for use according embodiment 1, wherein the aqueous pharmaceutical solution is a pharmaceutical infusion or injection solution.

3. The aqueous pharmaceutical solution for use according to embodiments 1 or 2, wherein the aqueous pharmaceutical solution is enterally or parenterally, such as parenterally, administered.

4. The aqueous pharmaceutical solution for use according to 3, wherein the aqueous pharmaceutical solution is parenterally administered.

5. The aqueous pharmaceutical solution for use according to embodiment 4, wherein the parenteral administration is subcutaneous, percutaneous, intravenous, intra-arterial, intraosseous, intra-muscular, intracerebral, intracerebroventricular, or intrathecal, the administration mode being injection or infusion.

6. The aqueous pharmaceutical solution for use according to embodiment 3, wherein the enteral administration is duodenal administration.

7. The aqueous pharmaceutical solution for use according to any of embodiments 1 to 6, wherein the administration is continuous for up to 12 hours, such as 24 hours.

8. The aqueous pharmaceutical solution for use according to any of embodiments 1 to 7, wherein the aqueous pharmaceutical solution is administered before 15 wt %, such as before 10 wt %, of the levodopa in the aqueous pharmaceutical solution has degraded.

9. The aqueous pharmaceutical solution for use according to any one of the embodiments 1 to 8, wherein the aqueous pharmaceutical solution is administered to a subject suffering from a disease of the central nervous system (CNS) within 1 hour, such as within 50 minutes, 40 minutes, 30 minutes, 20 minutes, 10 minutes, 5 minutes, or 1 minute, from mixing the aqueous stock solution and the aqueous buffering solution.

10. The aqueous pharmaceutical solution for use according to any of embodiments 1 to 9, wherein the aqueous buffering solution and aqueous stock solution are continuously mixed and the thereby obtained aqueous pharmaceutical solution is continuously administered to the subject suffering from a disease of the central nervous system (CNS).

11. The aqueous pharmaceutical solution for use according to any of embodiments 1 to 10, wherein the aqueous pharmaceutical solution is supersaturated with levodopa.

12. The aqueous pharmaceutical solution for use in the treatment of diseases of the central nervous system (CNS), the aqueous pharmaceutical solution comprising;
at least 5 mg/ml dissolved levodopa, and having a pH in the range of 3.0 to 8.5,
wherein said aqueous pharmaceutical solution is supersaturated with levodopa.

13. The aqueous pharmaceutical solution, for use according to embodiment 12, wherein the aqueous pharmaceutical solution is provided by mixing;
   a) an aqueous stock solution comprising levodopa, said stock solution having a pH of less than 2.8 at 25° C.; and
   b) an aqueous buffering solution, for increasing the pH of said stock solution, comprising at least one buffer component, said buffering solution having a pH of at least 4.0 at 25° C.

14. The aqueous pharmaceutical solution, for use according to any one of the embodiments 1 to 13, wherein the aqueous pharmaceutical solution comprises at least 5 mg/ml dissolved levodopa, such as at least 6, 7, 8, 9, 10, 15, or 20 mg/ml dissolved levodopa; preferably the concentration of levodopa being in the range of 5 to 20 mg/ml dissolved levodopa, such as in the range 5 to 15 mg/ml or 5 to 10 mg/ml dissolved levodopa.

15. The aqueous pharmaceutical solution for use according to any one of the embodiments 1 to 14, wherein the aqueous pharmaceutical solution has a pH of 3.5 to 8.0, such as 4.0 to 7.5, 4.5 to 7.0, or 5.0 to 5.5.

16. The aqueous pharmaceutical solution for use according to any one of the embodiments 1 to 10 or 12 to 15, wherein the aqueous stock solution comprises at least 10 mg/ml levodopa, such as at least 15, 20, 25, 30, 35 or 40 mg/ml levodopa.

17. The aqueous pharmaceutical solution for use according to any one of the embodiments 1 to 10 or 12 to 16, wherein the aqueous stock solution has a pH of less than 2.0, such as less than 1.5, 1.0 or 0.5; preferably the pH of the aqueous stock solution has a pH being in the range of 0.0 to 2.0, such as 0.0 to 1.5, 0.0 to 1.0, or 0.0 to 0.5.

18. The aqueous pharmaceutical solution for use according to any one of the embodiments 1 to 10 or 12 to 17, wherein the aqueous stock solution comprises at least one physiologically acceptable acid.

19. The aqueous pharmaceutical solution for use according to embodiment 18, wherein the physiologically acceptable acid is a mineral acid, such as hydrochloric acid, sulfuric acid or nitric acid.

20. The aqueous pharmaceutical solution for use according to embodiment 19, wherein the mineral acid is hydrochloric acid (HCl); preferably the aqueous stock solution comprising at least 30 mM HCl, such as at least 50 mM HCl, 100 mM HCl, or 150 mM HCl.

21. The aqueous pharmaceutical solution for use according to embodiment 20, wherein the physiologically acceptable acid is acetic acid.

22. The aqueous pharmaceutical solution for use according to any one of embodiments 1 to 10 or 12 to 21, wherein the aqueous stock solution further comprises at least one stabilizer.

23. The aqueous pharmaceutical solution for use according to any one of embodiments 1 to 10 or 12 to 22, wherein said aqueous stock solution has been de-aired; such as by bubbling of an inert gas, e.g. nitrogen, through the aqueous stock solution, before being mixed with the aqueous buffering solution.

24. The aqueous pharmaceutical solution for use according to any one of the embodiments 1 to 23, further comprising at least one enzyme inhibitor.

25. The aqueous pharmaceutical solution for use according to embodiment 24, wherein the enzyme inhibitor is selected from the group consisting of dopa decarboxylase (DDC) inhibitors, catechol-o-methyltransferase (COMT) inhibitors and monoamino oxidase (MAO-B) inhibitors.

26. The aqueous pharmaceutical solution for use according to embodiment 25, wherein said enzyme inhibitor is:
   a. a dopa decarboxylase (DDC) inhibitor selected from the group consisting of carbidopa, such as carbidopa monohydrate, benserazide, methyldopa, and DFMD (alpha-difluoromethyl-DOPA);
   b. a catechol-o-methyltransferase (COMT) inhibitor selected from the group consisting of entacapone, tolcapone, and nitecapone;
   c. a monoamino oxidase (MAO-B) inhibitor selected from the group consisting of Rasagiline, Selegiline and Safinamide; or
   d. a combination thereof.

27. The aqueous pharmaceutical solution for use according to any one of embodiments 1 to 10 or 12 to 26, wherein the aqueous buffering solution has a pH of at least 4.0; preferably the pH of the aqueous buffering solution being between 4.0 and 12, such as between 4.0 and 9, 4.0 and 7.5, or 4.0 and 6.

28. The aqueous pharmaceutical solution for use according to any one of embodiments 1 to 10 or 12 to 27, wherein the aqueous buffering solution comprises at least one buffer component having at least one pKa value in the range of 3 to 9, such as in the range of 5 to 7.5.

29. The aqueous pharmaceutical solution for use according to embodiment 28, wherein the buffer component is citric acid.

30. The aqueous pharmaceutical solution for use according to embodiment 28, wherein the buffer components are citric acid and phosphate.

31. The aqueous pharmaceutical solution for use according to embodiment 28, wherein the buffer component is trometamol (tris(hydroxymethyl) aminomethane).

32. The aqueous pharmaceutical solution for use according to embodiment 28, wherein the buffer component is adipic acid, boric acid, calcium carbonate, calcium lactate, calcium phosphate, diethanolamine, glycine, maleic acid, meglumine, methionine, monosodium glutamate, potassium citrate, sodium acetate, sodium bicarbonate, sodium, sodium carbonate, sodium citrate dihydrate, sodium lactate, sodium phosphate dibasic, sodium phosphate monobasic or mixtures of two or more of these.

33. The aqueous pharmaceutical solution for use according to any one of embodiments 1 to 10 or 11 to 32, wherein the aqueous buffering solution further comprises at least one solubilizer.

34. The aqueous buffering solution for use according to embodiment 33, wherein the solubilizer is selected from the group consisting of: glutathione, cysteine, HP-beta-cyclodextrin, N-methyl pyrrolidinone (NMP), dimethylacetamide (DMA), collidone, kolliphor HS 15, PEG 400, propylenglycol, polysorbate 80, glycerine, ethanol, cremophor EL, DMSO, methionine, EDTA, ascorbic acid, aspartic acid, benzalkonium chloride, benzyl benzoate, cetylpyridinium chloride, hydroxypropyl betadex, lecithin, macrogol 15 hydroxystearate, meglumine, phospholipids, poloxamer, polyoxyethylene alkyl ethers, polyoxyethylene castor oil derivative, polyoxyethylene sorbitan fatty acid esters, pyrrolidone, triolein, vitamin E polyethylene glycol succinate or mixtures of two or more of these.

35. The aqueous pharmaceutical solution for use according to embodiment 34, wherein the solubilizer is HP-beta-cyclodextrin, preferably HP-beta-cyclodextrin being present in a concentration of about 75 mg/ml.

36. The aqueous pharmaceutical solution for use according to any one of embodiments 1 to 11 or 13 to 35, wherein the aqueous buffering solution further comprises at least one stabilizer.

37. The aqueous pharmaceutical solution for use according to embodiment 36, wherein the stabilizer is selected from the group consisting of stabilizing agents, antioxidants and preservatives or a combination of those.

38. The aqueous pharmaceutical solution for use according to embodiment 37, wherein the stabilizing agent is a physiologically acceptable sugar.

39. The aqueous pharmaceutical solution for use according to embodiment 38, wherein the physiologically acceptable sugar is glucose.

40. The aqueous pharmaceutical solution for use according to embodiment 39, wherein the glucose concentration is in the range of 5 to 100 mg/ml.

41. The aqueous pharmaceutical solution for use according to embodiment 37, wherein the aqueous pharmaceutical solution does not comprise glucose.

42. The aqueous pharmaceutical solution for use according to embodiment 37, wherein the stabilizing agent is bentonite, calcium alginate, calcium stearate, carboxymethyl cellulose calcium, ceratonia, cyclodextrins, dextran, diethanolamine, ethylene glycol palmitostearate, fructose, glyceryl monostearate, lecithin, macrogol 15 hydroxystearate, mannitol, monoethanolamine, propylene glycol, sodium acetate, sodium borate, sorbitol, sulfobutylether beta-cyclodextrin, trehalose, or zinc acetate.

43. The aqueous pharmaceutical solution for use according to embodiment 37, wherein the antioxidant is selected from the group consisting of alpha tocopherol, ascorbic acid, ascorbyl palmitate, butylated hydroxyanisole, citric acid monohydrate, erythorbic acid, malic acid, methionine, monothioglycerol, pentetic acid, potassium metabisulfite, propionic acid, sodium formaldehyde sulfoxylate, sodium metabisulfite, sodium sulfite, sodium thiosulfate.

44. The aqueous pharmaceutical solution for use according to embodiment 37, wherein the preservative is selected from the group consisting of benzalkonium chloride, benzethonium chloride, benzoic acid, boric acid, bronopol, butylene glycol, calcium acetate, calcium lactate pentahydrate, cetrimide, cetylpyridinium chloride, chlorobutanol, chlorocresol, citric acid monohydrate, cresol, edetic acid, ethyl parahydroxybenzoate, glycerol, imidurea, methyl parahydroxybenzoate, monothioglycerol, phenol, phenoxyethanol, and phenylethyl alcohol.

45. The aqueous pharmaceutical solution for use according to anyone of embodiments 36 to 44, wherein the solution is provided by mixing:
I) An aqueous stock solution, having of pH of less than 2.8 at 25° C. comprising;
  a) aqua sterile,
  b) levodopa,
  c) at least one enzyme inhibitor,
  d) at least one physiologically acceptable acid, and
  e) at least one a stabilizer,
wherein the stock solution is being bubbled with nitrogen after the being prepared, and
II) An aqueous buffering solution, having a pH of at least 4.0 at 25° C., comprising;
  f) aqua sterile,
  g) at least one buffer component, and
  h) at least one stabilizer and/or solubilizer,
  wherein the aqueous pharmaceutical solution optionally is oversaturated, and is administered to a subject suffering from a disease of the central nervous system (CNS) within 24 hours, such as within 16 hours, 12 hours, 6 hours, 4 hours, 2 hours, 1 hour, 30 minutes, 20 minutes, 10 minutes, 5 minutes, or 1 minute, from mixing the aqueous stock solution and the aqueous buffering solution.

46. The aqueous pharmaceutical solution for use according to any one of embodiments 36 to 54, comprising 10 mg/ml levodopa and 1.25 mg/ml (1:8) carbidopa, which is prepared by mixing:
I) An aqueous stock solution of 1000 ml comprising:
  a) 963 g water,
  b) 43.3 g 5 M HCl,
  wherein the solution is purged with nitrogen,
  c) 20 g micronized levodopa, and
  d) 2.71 g carbidopa monohydrate (equivalent to 2.5 g carbidopa), wherein the solution is once more purged with nitrogen,
II) An aqueous buffering solution comprising:
  e) 968 g water,
  f) 64.7 g tri-sodium citrate dihydrate,
  g) 3.56 g di-sodium hydrogen phosphate dihydrate, and
  h) 3.67 g 1M HCl.

47. The aqueous pharmaceutical solution for use according to embodiment 46, wherein the 2.5 g carbidopa is added as 2.71 g carbidopa monohydrate.

48. The aqueous pharmaceutical solution for use according to any one of embodiments 1 to 10 or 12 to 47, wherein at least 85 wt. % of the levodopa in pharmaceutical composition remains un-degraded for at least 1 minute, such as for at least 5, 10, 15, 20, 30, 40, 50, 60, 70, 80, 90, 100, 110, or 120 minutes, after the stock solution and the aqueous buffering solution have been mixed.

49. The aqueous pharmaceutical solution for use according to any one of embodiments 1 to 10 or 12 to 47, wherein the aqueous pharmaceutical solution comprises carbidopa, and wherein at least 85 wt.-% of the carbidopa remains un-degraded for at least 1 minute, such as for at least 5, 10, 20, 30, 40, 50, 60, 70, 80, 90, 100, 110, or 120 minutes, after the stock solution and the aqueous buffering solution have been mixed.

50. The aqueous pharmaceutical solution for use according to any one of embodiments 1 to 10 or 12 to 49, wherein the aqueous pharmaceutical solution comprises carbidopa, and wherein the level of DHPA (3,4-dihydroxyphenylacetone) is less than 5 mg % of carbidopa (CD), and the level of hydrazine is less than 1 mg % of carbidopa (CD) for at least 1 minute, such as for at least 5, 10, 20, 30, 40, 50, or 60 minutes, after the stock solution and the aqueous buffering solution have been mixed.

51. The aqueous pharmaceutical solution for use according to any of embodiments embodiment 1 to 10 or 12 to 48, wherein the aqueous pharmaceutical solution comprises carbidopa, and wherein the aqueous pharmaceutical solution is administered before 15 wt %, such as before 10 wt %, of the carbidopa in the aqueous pharmaceutical solution has degraded.

52. The aqueous pharmaceutical solution for use according to any one of embodiments 1-51, wherein the aqueous pharmaceutical solution has an osmolality of 50 to 1400 mOsm/kg, preferably 100 to 1000 mOsm/kg, or 200 to 600 mOsm/kg.

53. The aqueous pharmaceutical solution for use according to any one of embodiments 1-52, wherein the CNS disease is selected from the group consisting of Parkinson's disease, Atypical Parkinsonism, Alzheimer's disease, Restless Legs Syndrome (RLS) and the group of neurological mental illnesses; preferably the CNS disease is Parkinson's disease.

54. The aqueous pharmaceutical solution for use according to embodiment 53, wherein the CNS disease is Parkinson's disease in complication phase.

55. The aqueous pharmaceutical solution for use according to any one of embodiments 3 to 7, wherein the plasma level of levodopa reaches a therapeutic level within less than 3 hours, such as within 2 hours, 1 hour, 50 minutes, 40 minutes, 30 minutes, 20 minutes or 10 minutes from the point of time the administration commences.

56. The aqueous pharmaceutical solution for use according to any one of the embodiments 3 to 7 and 55, where the plasma level of levodopa may be adjusted, by adjusting the infusions rate, within a time period short enough to minimize on-off symptoms related to Parkinson's disease.

57. The aqueous pharmaceutical solution for use according to any one of the embodiments 1 to 56, wherein the solution enterally administered, preferably by duodenal administration.

58. The aqueous pharmaceutical solution for use according to any one of the embodiments 1 to 54, wherein the solution is formulated for injection.

59. A kit for providing an aqueous pharmaceutical solution, for use in the treatment of diseases of the central nervous system (CNS), according to any one of the preceding embodiments, the aqueous pharmaceutical solution comprising at least 5 mg/ml dissolved levodopa, and having a pH in the range of 3.0 to 8.5, said kit comprising;
 a) an aqueous stock solution comprising levodopa according to any one of the preceding embodiments, said aqueous stock solution having a pH of less than 2.8 at 25° C.
 b) an aqueous buffering solution according to any one of the preceding embodiments, for increasing the pH of said aqueous stock solution, comprising a buffer and having a pH of at least 4.0 at 25° C.;
 c) mixing means (1) for mixing said solutions a) and b); and
 d) an output means (2) for said mixed solution of step c).

60. The kit according to embodiment 59, wherein the output means (2) comprises or is connected to an injection or infusion means (20).

61. The kit according to embodiment 60, wherein the injection or infusion means (20) is a needle.

62. The kit according to embodiment 61, wherein the needle is made of plastic.

63. The kit according to any one of the embodiments 59 to 62, wherein the mixing means (1) comprises two compartments (3A, 3B), a pump (4), and a mixing chamber (10), wherein a first compartment (3A) contains means for receiving a container comprising the aqueous stock solution and a second compartment (3B) contains means for receiving a container comprising the aqueous buffering solution, the pump (4) being arranged to transport the aqueous stock solution and the aqueous buffering solution from the compartments (3A, 3B) to the mixing chamber (10), the mixing chamber (10) being arranged to provide for mixing of the received aqueous stock solution and the received aqueous buffering solution, and wherein the pump (4) further is arranged for transporting the mixed aqueous pharmaceutical solutions from the mixing chamber to the output means (2).

64. The kit according to embodiment 63, wherein the mixing means (1) comprises two pumps (4), the first pump (4) being connected to the first compartment (3A) and the second pump (4) being connected to the second compartment (3B).

65. The kit according to embodiment 63 or 64, wherein the pump (4) is a syringe pump, a volumetric pump, a peristaltic pump, or an ambulatory pump.

66. The kit according to any one of embodiments 63 to 65, wherein the first compartment (3A) is connected to the mixing chamber (10) by a first (5A) tubing, and the second compartment (3B) is connected to the mixing chamber (10) by a second (5B) tubing, and wherein the mixing chamber is connected to the output means (2) by a third tubing (5C).

67. The kit according to embodiment 66, wherein the tubing (5A, 5B, 5C), and/or the compartments (3A, 3B) are non-transparent or UV-absorbent.

68. The kit according to any one of embodiments 63 to 65, wherein the mixing chamber (10) is connected directly, without using tubing, to the compartments (3A, 3B) containing the aqueous stock solution and the aqueous buffering solution, respectively.

69. The kit according to any one of embodiments 63 to 68, wherein the mixing chamber (10) is 2-way Y-connector (11), preferably a Y'-Connector set 2 way; or
 wherein the mixing chamber (10) comprises a spiral formed channel (12) for mixing the two solutions; or
 wherein the mixing chamber (10) comprises a venturi mixer (13); or
 wherein the mixing chamber (10) contains a motorized mixing tool (14), such as a piston, a screw, a propeller or a similar device.

70. The kit according to any one of the embodiments 63 to 69, wherein the containers received by compartments (3A, 3B) are syringes, bags, bottles, or cassettes.

71. The kit according to any one of embodiments 63 to 70, wherein the kit further comprises a filter (6), such as a microbiological filter or a particle filter, arranged downstream the mixing chamber (10) for filtering the aqueous pharmaceutical solution before injection or infusion thereof.

72. The kit according to any one of embodiments 63 to 71, wherein the kit further comprises controlling means (7) to control the pump(s) (4), allowing for control of the flow rate of the pump(s) (4).

73. The kit according to any one of embodiments 63 to 72, wherein the kit further comprises a battery, to power active components, such as pump(s) (4), mixing chamber (10) and/or controlling means (7).

74. The kit according to any of embodiments 63 to 73, wherein the volume of the compartments (3A, 3B) is sufficient for enabling a subject suffering from a disease of the central nervous system (CNS) to be treated continuously for at least 4 hours, such as 4 to 6 hours, such as 6 to 10 hours, such as 10 to 16 hours, such as 16 to 24 hours; preferably the volume of each of the compartments (3A, 3B) is 10 to 1000 ml, such as 50 to 500 ml, such as 100 to 250 ml.

75. The kit according to any one of embodiments 63 to 74, wherein the containers received by compartments (3A, 3B) can be replaced or refilled.

76. The kit according to any one of embodiments 63 to 75, wherein the containers received by compartments (3A, 3B) can be replaced twice, 3 times, 4 times, 5 times or 6 times during a 24 hours period, enabling a subject to be treated continuously for 24 hours.

77. The kit according to embodiment 76, where the containers are provided with a quick-coupling enabling the time period for replacing containers be less than 10 minutes such as 8 minutes, 6 minutes, 3 minutes and 1 minute.

78. The kit according to any one of the embodiments 59 to 77, wherein the kit further comprises a pair of surgical gloves, cleaning wipes, and a disinfectant.

79. A set for providing an aqueous pharmaceutical solution, comprising:
 I) An aqueous stock solution, having of pH of less than 2.8 at 25° C. comprising;
  a) aqua sterile,
  b) levodopa,
  c) at least one enzyme inhibitor,
  d) at least one physiologically acceptable acid, and
  e) at least one a stabilizer,
 and
 II) An aqueous buffering solution, having a pH of at least 4.0 at 25° C., comprising;
  f) aqua sterile,
  g) at least one buffer component, and
  h) at least one stabilizer and/or solubilizer.

80. A set according to embodiment 79, wherein the aqueous stock solution comprises at least 10 mg/ml levodopa, such as at least 15, 20, 25, 30, 35 or 40 mg/ml levodopa.

81. A set according to embodiment 79 or 80, wherein the aqueous stock solution has a pH of less than 2.0, such as less than 1.5, 1.0 or 0.5; preferably the pH of the aqueous stock solution has a pH being in the range of 0.0 to 2.0, such as 0.0 to 1.5, 0.0 to 1.0, or 0.0 to 0.5.

82. A set according to any of embodiments 79 to 81, wherein the physiologically acceptable acid is a mineral acid, such as hydrochloric acid, sulfuric acid or nitric acid.

83. A set according to embodiments 82, wherein the mineral acid is hydrochloric acid (HCl); preferably the aqueous stock solution comprising at least 30 mM HCl, such as at least 50 mM HCl, 100 mM HCl, or 150 mM HCl.

84. A set according to any of embodiments 79 to 83, wherein the physiologically acceptable acid is acetic acid.

85. A set according to any of embodiments 79 to 84, wherein the enzyme inhibitor is selected from the group consisting of dopa decarboxylase (DDC) inhibitors, catechol-o-methyltransferase (COMT) inhibitors and monoamino oxidase (MAO-B) inhibitors.

86. A set according to embodiment 85, wherein said enzyme inhibitor is:
a dopa decarboxylase (DDC) inhibitor selected from the group consisting of carbidopa, such as carbidopa monohydrate, benserazide, methyldopa, and DFMD (alpha-difluoromethyl-DOPA);
a catechol-o-methyltransferase (COMT) inhibitor selected from the group consisting of entacapone, tolcapone, and nitecapone;
a monoamino oxidase (MAO-B) inhibitor selected from the group consisting of Rasagiline, Selegiline and Safinamide; or
a combination thereof.

87. A set according to any of embodiments 79 to 86, wherein the aqueous buffering solution has a pH of at least 4.0; preferably the pH of the aqueous buffering solution being between 4.0 and 12, such as between 4.0 and 9, 4.0 and 7.5, or 4.0 and 6.

88. A set according to any of embodiments 79 to 87, wherein the at least one buffer component has at least one pKa value in the range of 3 to 9, such as in the range of 5 to 7.5.

89. A set according to any of embodiments 79 to 88, wherein the buffer component is citric acid.

90. A set according to any of embodiments 79 to 88, wherein the buffer components are citric acid and phosphate.

91. A set according to any of embodiments 79 to 88, wherein the buffer component is trometamol (tris(hydroxymethyl) aminomethane).

92. A set according to any of embodiments 79 to 88, wherein the buffer component is adipic acid, boric acid, calcium carbonate, calcium lactate, calcium phosphate, diethanolamine, glycine, maleic acid, meglumine, methionine, monosodium glutamate, potassium citrate, sodium acetate, sodium bicarbonate, sodium, sodium carbonate, sodium citrate dihydrate, sodium lactate, sodium phosphate dibasic, sodium phosphate monobasic and the like or mixtures of two or more of these.

93. A set according to any of embodiments 79 to 92, wherein the solubilizer is selected from the group consisting of: glutathione, cysteine, HP-beta-cyclodextrin, N-methyl pyrrolidinone (NMP), dimethylacetamide (DMA), collidone, kolliphor HS 15, PEG 400, propylenglycol, polysorbate 80, glycerine, ethanol, cremophor EL, DMSO, methionine, EDTA, ascorbic acid, aspartic acid, benzalkonium chloride, benzyl benzoate, cetylpyridinium chloride, hydroxypropyl betadex, lecithin, macrogol 15 hydroxystearate, meglumine, phospholipids, poloxamer, polyoxyethylene alkyl ethers, polyoxyethylene castor oil derivative, polyoxyethylene sorbitan fatty acid esters, pyrrolidone, triolein, vitamin E polyethylene glycol succinate or mixtures of two or more of these.

94. A set according to any of embodiments 79 to 92, wherein the solubilizer is HP-beta-cyclodextrin, preferably HP-beta-cyclodextrin being present in a concentration of 60 to 90 mg/ml, such as about 75 mg/ml.

95. A set according to any of embodiments 79 to 94, wherein the stabilizer is selected from the group consisting of stabilizing agents, antioxidants and preservatives or a combination of those.

96. A set according to any of embodiments 79 to 94, wherein the stabilizing agent is a physiologically acceptable sugar.

97. A set according to embodiment 96, wherein the physiologically acceptable sugar is glucose.

98. A set according to embodiment any of embodiments 79 to 96, wherein the pharmaceutical solution does not comprise glucose.

99. A set according to any of embodiments 79 to 94, wherein the stabilizing agent is bentonite, calcium alginate, calcium stearate, carboxymethyl cellulose calcium, ceratonia, cyclodextrins, dextran, diethanolamine, ethylene glycol palmitostearate, fructose, glyceryl monostearate, lecithin, macrogol 15 hydroxystearate, mannitol, monoethanolamine, propylene glycol, sodium acetate, sodium borate, sorbitol, sulfobutylether beta-cyclodextrin, trehalose, or zinc acetate.

100. A set according to embodiment 95, wherein the antioxidant is selected from the group consisting of alpha tocopherol, ascorbic acid, ascorbyl palmitate, butylated hydroxyanisole, citric acid monohydrate, erythorbic acid, malic acid, methionine, monothioglycerol, pentetic acid, potassium metabisulfite, propionic acid, sodium formaldehyde sulfoxylate, sodium metabisulfite, sodium sulfite, sodium thiosulfate.

101. A set according to embodiment 95, wherein the preservative is selected from the group consisting of benzalkonium chloride, benzethonium chloride, benzoic acid, boric acid, bronopol, butylene glycol, calcium acetate, calcium lactate pentahydrate, cetrimide, cetylpyridinium chloride, chlorobutanol, chlorocresol, citric acid monohydrate, cresol, edetic acid, ethyl parahydroxybenzoate, glycerol, imidurea, methyl parahydroxybenzoate, monothioglycerol, phenol, phenoxyethanol, and phenylethyl alcohol.

102. A set for mixing an aqueous pharmaceutical solution comprising 10 mg/ml levodopa and 1.25 mg/ml (1:8) carbidopa according to anyone of embodiments 37 to 45, comprising:
I) An aqueous stock solution of 1000 ml comprising:
a) 963 g water,
b) 43.3 g 5 M HCl,
wherein the solution is purged with nitrogen,
c) 20 g micronized levodopa, and
d) 2.71 g carbidopa monohydrate (equivalent to 2.5 g carbidopa),
wherein the solution is once more purged with nitrogen,
II) An aqueous buffering solution comprising:
e) 968 g water,
f) 64.7 g tri-sodium citrate dihydrate,
g) 3.56 g di-sodium hydrogen phosphate dihydrate, and
h) 3.67 g 1M HCl.

103. A method of continuously preparing an aqueous pharmaceutical solution for use in the treatment of diseases of the central nervous system (CNS), the aqueous pharmaceutical solution being suitable for continuous parenteral or enteral administration, wherein the method comprises:

continuously mixing a flow of a stock solution comprising levodopa, said stock solution having a pH of less than 2.8 at 25° C. and a flow of an aqueous buffering solution, said buffering solution having a pH of at least 4.0 at 25° C.; and continuously obtaining from said mixing a continuous flow of an aqueous pharmaceutical solution comprising at least 5 mg/ml dissolved levodopa, such as at least 6, 7, 8, 9, 10, 15, or 20 mg/ml dissolved levodopa; preferably the concentration of levodopa being in the range of 5 to 20 mg/ml dissolved levodopa, such as in the range 5 to 15 mg/ml or 5 to 10 mg/ml dissolved levodopa.

104. The method according to embodiment 103, wherein the aqueous pharmaceutical solution has a pH of 3.5 to 8.0, such as 4.0 to 7.5, 4.5 to 7.0 or 5.0 to 5.5.

105. The method according to embodiment 103 or 104, wherein the aqueous stock solution comprises at least 10 mg/ml levodopa, such as at least 15, 20, 25, 30, 35 or 40 mg/ml levodopa.

106. The method according to any of embodiments 103 to 105, wherein the aqueous stock solution has a pH of less than 2.0, such as less than 1.5, 1.0 or 0.5; preferably the pH of the aqueous stock solution has a pH being in the range of 0.0 to 2.0, such as 0.0 to 1.5, 0.0 to 1.0, or 0.0 to 0.5.

107. The method according to any of embodiments 103 to 106, wherein the aqueous stock solution comprises at least one physiologically acceptable acid.

108. The method according to embodiment 107, wherein the physiologically acceptable acid is a mineral acid, such as hydrochloric acid, sulfuric acid or nitric acid.

109. The method according to embodiment 108, wherein the mineral acid is hydrochloric acid (HCl); preferably the aqueous stock solution comprising at least 30 mM HCl, such as at least 50 mM HCl, 100 mM HCl, or 150 mM HCl.

110. The method according to embodiment 107, wherein the physiologically acceptable acid is acetic acid.

111. The method according to any of embodiments 103 to 110, wherein the aqueous stock solution further comprises at least one stabilizer.

112. The method according to any of embodiments 103 to 111, wherein the method further comprises the step of de-airing the stock solution; such as by bubbling of an inert gas, e.g. nitrogen, through the stock solution, before being mixed with the aqueous buffering solution.

113. The method according to any of embodiments 103 to 112, wherein the aqueous pharmaceutical solution further comprises at least one enzyme inhibitor.

114. The method according to embodiment 113, wherein the enzyme inhibitor is selected from the group consisting of dopa decarboxylase (DDC) inhibitors, catechol-o-methyltransferase (COMT) inhibitors and monoamino oxidase (MAO-B) inhibitors.

115. The method according to embodiment 113 or 114, wherein said enzyme inhibitor is:

a dopa decarboxylase (DDC) inhibitor selected from the group consisting of carbidopa, such as carbidopa monohydrate, benserazide, methyldopa, and DFMD (alpha-difluoromethyl-DOPA);

a catechol-o-methyltransferase (COMT) inhibitor selected from the group consisting of entacapone, tolcapone, and nitecapone;

a monoamino oxidase (MAO-B) inhibitor selected from the group consisting of Rasagiline, Selegiline and Safinamide; or a combination thereof.

116. The method according to any of embodiments 103 to 115, wherein the aqueous buffering solution has a pH of at least 4.0; preferably the pH of the aqueous buffering solution being between 4.0 and 12, such as between 4.0 and 9, 4.0 and 7.5, or 4.0 and 6.

117. The method according to any of embodiments 103 to 116, wherein the aqueous buffering solution comprises at least one buffer component having at least one pKa value in the range of 3 to 9, such as in the range of 5 to 7.5.

118. The method according to embodiment 117, wherein the buffer component is citric acid.

119. The method according to embodiment 117, wherein the buffer components are citric acid and phosphate.

120. The method according to embodiment 117, wherein the buffer component is trometamol (tris(hydroxymethyl)aminomethane).

121. The method according to embodiment 117, wherein the buffer component is adipic acid, boric acid, calcium carbonate, calcium lactate, calcium phosphate, diethanolamine, glycine, maleic acid, meglumine, methionine, monosodium glutamate, potassium citrate, sodium acetate, sodium bicarbonate, sodium, sodium carbonate, sodium citrate dihydrate, sodium lactate, sodium phosphate dibasic, sodium phosphate monobasic and the like or mixtures of two or more of these.

122. The method according to any of embodiments 103 to 121, wherein the aqueous buffering solution further comprises at least one solubilizer.

123. The method according to embodiment 122, wherein the solubilizer is selected from the group consisting of: glutathione, cysteine, HP-beta-cyclodextrin, N-methyl pyrrolidinone (NMP), dimethylacetamide (DMA), collidone, kolliphor HS 15, PEG 400, propylenglycol, polysorbate 80, glycerine, ethanol, cremophor EL, DMSO, methionine, EDTA, ascorbic acid, aspartic acid, benzalkonium chloride, benzyl benzoate, cetylpyridinium chloride, hydroxypropyl betadex, lecithin, macrogol 15 hydroxystearate, meglumine, phospholipids, poloxamer, polyoxyethylene alkyl ethers, polyoxyethylene castor oil derivative, polyoxyethylene sorbitan fatty acid esters, pyrrolidone, triolein, vitamin E polyethylene glycol succinate or mixtures of two or more of these.

124. The method according to embodiment 122, wherein the solubilizer is HP-beta-cyclodextrin, preferably HP-beta-cyclodextrin being present in a concentration of about 75 mg/ml.

125. The method according to any of embodiments 103 to 124, wherein the aqueous buffering solution further comprises at least one stabilizer.

126. The method according to embodiment 125, wherein the stabilizer is selected from the group consisting of stabilizing agents, antioxidants and preservatives or a combination of those.

127. The method according to any of embodiments embodiment 125, wherein stabilizer is a stabilizing agent, the stabilizing agent being a physiologically acceptable sugar.

128. The method according to embodiment 127, wherein the physiologically acceptable sugar is glucose.

129. The method according to embodiment 128, wherein the glucose concentration is in the range of 5 to 100 mg/ml.

130. The method according to any of embodiments 103 to 127, wherein the pharmaceutical solution does not comprise glucose.

131. The method according to embodiment 126, wherein the stabilizing agent is bentonite, calcium alginate, calcium stearate, carboxymethyl cellulose calcium, ceratonia, cyclodextrins, dextran, diethanolamine, ethylene glycol palmitostearate, fructose, glyceryl monostearate, lecithin, macrogol 15 hydroxystearate, mannitol, monoethanolamine, propylene glycol, sodium acetate, sodium borate, sorbitol, sulfobutylether beta-cyclodextrin, trehalose, or zinc acetate.

132. The method according to embodiment 126, wherein the antioxidant is selected from the group consisting of alpha tocopherol, ascorbic acid, ascorbyl palmitate, butylated hydroxyanisole, citric acid monohydrate, erythorbic acid, malic acid, methionine, monothioglycerol, pentetic acid, potassium metabisulfite, propionic acid, sodium formaldehyde sulfoxylate, sodium metabisulfite, sodium sulfite, sodium thiosulfate.

133. The method according to embodiment 126, wherein the preservative is selected from the group consisting of benzalkonium chloride, benzethonium chloride, benzoic acid, boric acid, bronopol, butylene glycol, calcium acetate, calcium lactate pentahydrate, cetrimide, cetylpyridinium chloride, chlorobutanol, chlorocresol, citric acid monohydrate, cresol, edetic acid, ethyl parahydroxybenzoate, glycerol, imidurea, methyl parahydroxybenzoate, monothioglycerol, phenol, phenoxyethanol, and phenylethyl alcohol.

134. The method according to any of embodiments 103 to 133, wherein the aqueous pharmaceutical solution is supersaturated with levodopa.

135. A method of treating diseases of the central nervous system (CNS) comprising:
continuously mixing a flow of a stock solution comprising levodopa, said stock solution having a pH of less than 2.8 at 25° C. and a flow of an aqueous buffering solution, said buffering solution having a pH of at least 4.0 at 25° C.;
continuously obtaining from said mixing a continuous flow of an aqueous pharmaceutical solution comprising at least 5 mg/ml dissolved levodopa, such as at least 6, 7, 8, 9, 10, 15, or 20 mg/ml dissolved levodopa; preferably the concentration of levodopa being in the range of 5 to 20 mg/ml dissolved levodopa, such as in the range 5 to 15 mg/ml or 5 to 10 mg/ml dissolved levodopa; and
continuously administering to a subject suffering from a disease of the central nervous system (CNS) the obtained aqueous pharmaceutical solution.

136. The method of treating diseases of the central nervous system (CNS) according to embodiment 135, wherein the solution is a pharmaceutical infusion or injection solution.

137. The method of treating diseases of the central nervous system (CNS) according to any of embodiments 135 to 136, wherein the solution is parenterally administered.

138. The method of treating diseases of the central nervous system (CNS) according to embodiment 137, wherein the parenteral administration is subcutaneous, percutaneous, intravenous, intra-arterial, intraosseous, intramuscular, intracerebral, intracerebroventricular, or intrathecal, the administration mode being injection or infusion.

139. The method of treating diseases of the central nervous system (CNS) according to any of embodiments 135 to 138, wherein the CNS disease is selected from the group consisting of Parkinson's disease, Atypical Parkinsonism, Alzheimer's disease, Restless Legs Syndrome (RLS) and the group of neurological mental illnesses; preferably the CNS disease is Parkinson's disease.

140. The method of treating diseases of the central nervous system (CNS) according to any of embodiments 135 to 139, wherein the aqueous pharmaceutical solution is administered within 10 minutes, 5 minutes or 1 minute, from mixing the aqueous stock solution and the aqueous buffering solution.

141. The method of treating diseases of the central nervous system (CNS) according to any of embodiments 135 to 140, wherein the aqueous pharmaceutical solution has a pH of 3.5 to 8.0, such as 4.0 to 7.5, 4.5 to 7.0, or 5.0 to 5.5.

142. The method of treating diseases of the central nervous system (CNS) according to any of embodiments 135 to 141, wherein the aqueous stock solution comprises at least 10 mg/ml levodopa, such as at least 15, 20, 25, 30, 35 or 40 mg/ml levodopa.

143. The method of treating diseases of the central nervous system (CNS) according to any of embodiments 135 to 142, wherein the aqueous stock solution has a pH of less than 2.0, such as less than 1.5, 1.0 or 0.5; preferably the pH of the aqueous stock solution has a pH being in the range of 0.0 to 2.0, such as 0.0 to 1.5, 0.0 to 1.0, or 0.0 to 0.5.

144. The method of treating diseases of the central nervous system (CNS) according to any of embodiments 135 to 143, wherein the aqueous stock solution comprises at least one physiologically acceptable acid.

145. The method of treating diseases of the central nervous system (CNS) according to embodiment 144, wherein the physiologically acceptable acid is a mineral acid, such as hydrochloric acid, sulfuric acid or nitric acid.

146. The method of treating diseases of the central nervous system (CNS) according to embodiment 145, wherein the mineral acid is hydrochloric acid (HCl); preferably the aqueous stock solution comprising at least 30 mM HCl, such as at least 50 mM HCl, 100 mM HCl, or 150 mM HCl.

147. The method of treating diseases of the central nervous system (CNS) according to embodiment 144, wherein the physiologically acceptable acid is acetic acid.

148. The method of treating diseases of the central nervous system (CNS) according to any of embodiments 135 to 147, wherein the aqueous stock solution further comprises at least one stabilizer.

149. The method of treating diseases of the central nervous system (CNS) according to any of embodiments 135 to 148, wherein the method further comprises the step of de-airing the stock solution; such as by bubbling of an inert gas, e.g. nitrogen, through the stock solution, before being mixed with the aqueous buffering solution.

150. The method of treating diseases of the central nervous system (CNS) according to any of embodiments 135 to 149, wherein the aqueous pharmaceutical solution further comprises at least one enzyme inhibitor.

151. The method of treating diseases of the central nervous system (CNS) according to embodiment 150, wherein the enzyme inhibitor is selected from the group consisting of dopa decarboxylase (DDC) inhibitors, catechol-o-methyltransferase (COMT) inhibitors and monoamino oxidase (MAO-B) inhibitors.

152. The method of treating diseases of the central nervous system (CNS) according to any of embodiments 150 to 151, wherein said enzyme inhibitor is:

a dopa decarboxylase (DDC) inhibitor selected from the group consisting of carbidopa, such as carbidopa monohydrate, benserazide, methyldopa, and DFMD (alpha-difluoromethyl-DOPA);

a catechol-o-methyltransferase (COMT) inhibitor selected from the group consisting of entacapone, tolcapone, and nitecapone;

a monoamino oxidase (MAO-B) inhibitor selected from the group consisting of Rasagiline, Selegiline and Safinamide; or a combination thereof.

153. The method of treating diseases of the central nervous system (CNS) according to any of embodiments 135 to 152, wherein the aqueous buffering solution has a pH of at least 4.0; preferably the pH of the aqueous buffering solution being between 4.0 and 12, such as between 4.0 and 9, 4.0 and 7.5, or 4.0 and 6.

154. The method of treating diseases of the central nervous system (CNS) according to any of embodiments 135 to 153, wherein the aqueous buffering solution comprises at least one buffer component having at least one pKa value in the range of 3 to 9, such as in the range of 5 to 7.5.

155. The method of treating diseases of the central nervous system (CNS) according to embodiment 154, wherein the buffer component is citric acid.

156. The method of treating diseases of the central nervous system (CNS) according to embodiment 154, wherein the buffer components are citric acid and phosphate.

157. The method of treating diseases of the central nervous system (CNS) according to embodiments 154, wherein the buffer component is trometamol (tris(hydroxymethyl) aminomethane).

158. The method of treating diseases of the central nervous system (CNS) according to embodiment 154, wherein the buffer component is adipic acid, boric acid, calcium carbonate, calcium lactate, calcium phosphate, diethanolamine, glycine, maleic acid, meglumine, methionine, monosodium glutamate, potassium citrate, sodium acetate, sodium bicarbonate, sodium, sodium carbonate, sodium citrate dihydrate, sodium lactate, sodium phosphate dibasic, sodium phosphate monobasic and the like or mixtures of two or more of these.

159. The method of treating diseases of the central nervous system (CNS) according to any of embodiments 135 to 158, wherein the aqueous buffering solution further comprises at least one solubilizer.

160. The method of treating diseases of the central nervous system (CNS) according to embodiment 159, wherein the solubilizer is selected from the group consisting of: glutathione, cysteine, HP-beta-cyclodextrin, N-methyl pyrrolidinone (NMP), dimethylacetamide (DMA), collidone, kolliphor HS 15, PEG 400, propylenglycol, polysorbate 80, glycerine, ethanol, cremophor EL, DMSO, methionine, EDTA, ascorbic acid, aspartic acid, benzalkonium chloride, benzyl benzoate, cetylpyridinium chloride, hydroxypropyl betadex, lecithin, macrogol 15 hydroxystearate, meglumine, phospholipids, poloxamer, polyoxyethylene alkyl ethers, polyoxyethylene castor oil derivative, polyoxyethylene sorbitan fatty acid esters, pyrrolidone, triolein, vitamin E polyethylene glycol succinate or mixtures of two or more of these.

161. The method of treating diseases of the central nervous system (CNS) according to embodiment 159, wherein the solubilizer is HP-beta-cyclodextrin, preferably HP-beta-cyclodextrin being present in a concentration of 60 to 90 mg/ml, such as about 75 mg/ml.

162. The method of treating diseases of the central nervous system (CNS) according to any of embodiments 135 to 161, wherein the aqueous buffering solution further comprises at least one stabilizer.

163. The method of treating diseases of the central nervous system (CNS) according to embodiment 162, wherein the stabilizer is selected from the group consisting of stabilizing agents, antioxidants and preservatives or a combination of those.

164. The method of treating diseases of the central nervous system (CNS) according to embodiment 163, wherein stabilizer is a stabilizing agent, the stabilizing agent being a physiologically acceptable sugar.

165. The method of treating diseases of the central nervous system (CNS) according to embodiment 164, wherein the physiologically acceptable sugar is glucose.

166. The method of treating diseases of the central nervous system (CNS) according to embodiment 165, wherein the glucose concentration is in the range of 5 to 100 mg/ml.

167. The method of treating diseases of the central nervous system (CNS) according to any of embodiments 135 to 163, wherein the pharmaceutical solution does not comprise glucose.

168. The method of treating diseases of the central nervous system (CNS) according to embodiment 163, wherein the stabilizing agent is bentonite, calcium alginate, calcium stearate, carboxymethyl cellulose calcium, ceratonia, cyclodextrins, dextran, diethanolamine, ethylene glycol palmitostearate, fructose, glyceryl monostearate, lecithin, macrogol 15 hydroxystearate, mannitol, monoethanolamine, propylene glycol, sodium acetate, sodium borate, sorbitol, sulfobutylether beta-cyclodextrin, trehalose, or zinc acetate.

169. The method of treating diseases of the central nervous system (CNS) according to embodiment 163, wherein the antioxidant is selected from the group consisting of alpha tocopherol, ascorbic acid, ascorbyl palmitate, butylated hydroxyanisole, citric acid monohydrate, erythorbic acid, malic acid, methionine, monothioglycerol, pentetic acid, potassium metabisulfite, propionic acid, sodium formaldehyde sulfoxylate, sodium metabisulfite, sodium sulfite, sodium thiosulfate.

170. The method of treating diseases of the central nervous system (CNS) according to embodiment 163, wherein the preservative is selected from the group consisting of benzalkonium chloride, benzethonium chloride, benzoic acid, boric acid, bronopol, butylene glycol, calcium acetate, calcium lactate pentahydrate, cetrimide, cetylpyridinium chloride, chlorobutanol, chlorocresol, citric acid monohydrate, cresol, edetic acid, ethyl parahydroxybenzoate, glycerol, imidurea, methyl parahydroxybenzoate, monothioglycerol, phenol, phenoxyethanol, and phenylethyl alcohol.

171. The method of treating diseases of the central nervous system (CNS) according to any of embodiments 135 to 170, wherein the aqueous pharmaceutical solution is supersaturated with levodopa.

To further describe the invention, reference will be given to the following experimental examples. These examples are included merely for purposes of illustration of certain aspects and embodiments of the present invention and are not intended to limit the invention in any way.

Experimental Section

To provide a perspective to the range of components that may be part of the solution of the invention, and to their effect, the results of a number of experiments are summarized below.

A preferred aqueous pharmaceutical solution containing 10 mg/ml levodopa and 1.25 mg/ml (1:8) carbidopa was prepared using the following components, steps and methods.

A 20 mg/ml levodopa and 2.5 mg/ml carbidopa stock solution of 1000 ml was prepared as follows:

963 g water was poured into a Duran bottle equipped with a magnetic stirrer, whereupon, 43.3 g 5 M hydrochloric acid (HCl) was added, whereupon, the solution was purged with nitrogen until the residual oxygen content was <0.1 ppm, whereupon, 20 g micronized levodopa was added, whereupon, 2.71 g carbidopa monohydrate (equivalent to 2.5 g carbidopa) was added.

The resulting solution was stirred, using the magnetic stirrer, until all substances were dissolved in the solution.

The pH was measured to approximately 1.

The solution was again purged with nitrogen until the residual oxygen content was <0.1 ppm.

A buffering solution was prepared as follows:

968 g water was poured Into a Duran bottle equipped with a magnetic stirrer whereupon 64.7 g tri-sodium citrate dihydrate was added, whereupon, 3.56 g di-sodium hydrogen phosphate dihydrate was added, whereupon, 3.67 g 1M hydrochloric acid HCl was added, whereupon, the solution was stirred, using the magnetic stirrer, until all material was dissolved.

The pH was measured and adjusted to 7.6 using 1 M HCl (in the event the solution was too basic) and 1M sodium hydroxide (NaOH) (in the event the solution was too acidic).

The stock solution was transferred into the syringe of a B Braun syringe pump (SPACE Infusion Pump System) and the buffering solution was transferred into the syringe of another syringe pump of the same make. The outlets of the syringes of the syringe pumps were connected to UV-protected lines (B Braun Original Perfusor Lines with light protection) provided with B Braun Safeflow valves and a back check valve and each led to an Y-coupling (BD Carefusion Y'-connector set, 2 way; Becton, Dickinson and Company) in which the stock solution and the buffering solutions were mixed, without the use any active mixing means, whereupon the mixed solution was led, from the single outlet of the Y-coupling, through a UV-protected line (B Braun) to a 0.2 µm particle filter (B Braun Sterifix) and finally to a steel needle intended for intravenous infusion (B Braun Venofix Safety).

Measurements, showing the degradation of the concentration of levodopa and carbidopa as well as the content of DHPA, were made on the mixed solution after coming out from the steel needle. The following results were registered after 22 hours of operation (the hydrazine levels have been calculated based on the DHPA levels assuming that each degraded carbidopa molecule was split into one molecule of DHPA and one molecule of hydrazine): There was no decomposition of levodopa, the decomposition of carbidopa was 2.4% and the content of DHPA was 1.3 net mg % corresponding to a hydrazine level of 0.25 mg % (mg % with reference to carbidopa).

To provide a perspective to the range of components that may be part of the solution of the invention, and to their effect, the results of a number of experiments are summarized below Example 1

A stock solution (pH<1) of levodopa and carbidopa was prepared containing:

50 mg/ml levodopa
5 mg/ml carbidopa monohydrate
5 mg/ml sodium metabisulphite
0.303 M HCl
Aqua sterile The mixing of the stock solution and the buffering solution containing the buffer component trometamol and glucose (approx. proportion acidic stock to basic solution of trometamol and glucose was 1:1) was tested in 3 similar set-ups of samples as shown in the following table. All batches were prepared by adding Addex-THAM (or a trometamol solution produced in-house; pH approx. 9) and glucose produced by B Braun (or glucose solution produced in house). In 001C glucose was first stirred into the solution, then trometamol. In 001 D and E both solutions were mixed prior to being stirred into the solution.

TABLE 1

Physical stability of levodopa and carbidopa after mixing the stock and the buffering solution.

| | Samples | | |
|---|---|---|---|
| | 001 C | 001 D | 001 E |
| Levodopa (mg/ml) | 10 | 10 | 10 |
| Carbidopa (mg/ml) | 1 | 1 | 1 |
| Sodium metabisulphite (mg/ml) | 1 | 1 | 1 |
| Trometamol (mg/ml) | 8.0 | 8.0 | 8.8 |
| Glucose (mg/ml) | 39 | 39 | 38.9 |
| pH | 3.2 | 3.1 | 3.5 |
| Physically stable at room temperature | <3 days | <3 days | <3 days |
| Physically stable in refrigerator | <3 days | <3 days | <3 days |

The physical stability was less than 3 days in all tests—both at room temperature and refrigerated. No difference was observed in the way glucose and trometamol was stirred into the solution.

Furthermore, it was tested whether a decrease of the concentrations of levodopa, and carbidopa respectively, would improve the physical stability.

TABLE 2

Physical stability of two concentrations of levodopa and carbidopa in ratio 10/1 at pH 3.6-3.7

| | Samples | | | | | |
|---|---|---|---|---|---|---|
| | 002 A | 002 B | 002 C | 002 D | 002 E | 002 F |
| Levodopa (mg/ml) | 10 | 5 | 10 | 5 | 10 | 5 |
| Carbidopa (mg/ml) | 1 | 0.5 | 1 | 0.5 | 1 | 0.5 |
| Sodium metabisulphite (mg/ml) | 1 | 0.5 | 1 | 0.5 | 1 | 0.5 |
| Trometamol (ca mg/ml) | 8.0 | 4.0 | 8.0 | 4.0 | 8.0 | 4.0 |
| Glucose (ca mg/ml) | 39 | 44.5 | 39 | 44.5 | 39 | 44.5 |
| Physically stable at room temperature | <4 days | 6 months | <4 days | 6 months | <4 days | 6 months |
| Physically stable in refrigerator | 4 days | NA | <4 days | <6 months | <4 days | 6 months |

The results show that the formulation containing 5 mg/ml levodopa and 0.5 mg/ml carbidopa seems to be soluble and physically stable up to 6 months in room temperature, whereas 10 mg/ml levodopa together with 1 mg/ml carbidopa was unstable. The physical stability appears to be better at room temperature than refrigerated Three different types of solubility enhancers were tested in the formulation: Kolliphor HS 15 (non-ionic surfactant), polyethylene glycol 400 (co-solvent) and HP-β-cyclodextrin (complex forming agent). The pH was 2.9-3.0.

TABLE 3

Physical stability enhancement by Kolliphor HS 15, polyethylene glycol 400 and HP-β-cyclodextrin at pH 2.9 to 3.0

|  | Samples | | |
| --- | --- | --- | --- |
|  | 004A | 004B | 004C |
| Levodopa (mg/ml) | 10 | 10 | 10 |
| Carbidopa (mg/ml) | 1 | 1 | 1 |
| Sodium metabisulphite (mg/ml) | 1 | 1 | 1 |
| Kolliphor HS 15 (mg/ml) | 200 | — | — |
| Polyethylene glycol 400 (mg/ml) | — | 200 | — |
| HP-β-cyclodextrin (mg/ml) | — | — | 200 |
| Trometamol (ca mg/ml) | 8.0 | 8.0 | 8.0 |
| Glucose (ca mg/ml) | 29 | 29 | 29 |
| Physically stable at room temp. | <3 days | <3 days | <3 days |
| Physically stable in refrigerator | <3 days | <3 days | <3 days |

Hence, improved physical stability of 10 mg/ml levodopa and 1 mg/ml carbidopa could not be achieved with any of the 3 solubility enhancers, at the concentrations tested.

It was tested to lower the trometamol concentration and vary the glucose concentration.

TABLE 4

Physical stability of LD and CD with varying trometamol and glucose concentrations.

|  | Samples | | | | | |
| --- | --- | --- | --- | --- | --- | --- |
|  | 005B1 | 005B2 | 005B3 | 005E | 005H | 005J |
| Levodopa (mg/ml) | 10 | 10 | 10 | 10 | 10 | 10 |
| Carbidopa (mg/ml) | 1 | 1 | 1 | 1 | 1 | 1 |
| Sodium metabis. (mg/ml) | 1 | 1 | 1 | 1 | 1 | 1 |
| HCl (mM; from stock) | 61 | 61 | 61 | 61 | 61 | 61 |
| Trometamol (ca mg/ml) | 8.8 | 8.0 | 7.2 | 7.2 | 7.2 | 7.2 |
| Glucose (ca mg/ml) | 0 | 0 | 0 | 39 | 78 | 19.5 |
| pH | 6.6 | 4.2 | 3.1 | 3.1 | 3.2 | 3.1 |
| Physically stable at room temp. | <2 days | <2 days | <2 days | <2 days | 2 weeks | 5 days |
| Physically stable in refrigerator | NA | NA | NA | NA | <1 day | <1 day |

Results show that an increase in glucose concentration possibly prolongs the time before precipitation is observed. The physical stability is decreased by refrigeration. Altering the pH from 3.1 to 6.6 did not improve physical stability at room temperature.

Two lower concentrations of polyethylene glycol 400 were tested as well as a lower concentration of HP-β-cyclodextrin than previously as an alternative.

TABLE 5

Physical stability of LD and CD with polyethylene glycol 400 or HP-β-cyclodextrin

|  | Samples | | |
| --- | --- | --- | --- |
|  | 006 A | 007 A | 007 B |
| Levodopa (mg/ml) | 10 | 10 | 10 |
| Carbidopa (mg/ml) | 1 | 1 | 1 |
| Sodium metabisulphite (mg/ml) | 1 | 1 | 1 |
| Polyethylene glycol 400 (mg/ml) | — | 100 | 50 |
| HP-β-cyclodextrin (mg/ml) | 75 | — | — |
| Trometamol (ca mg/ml) | 7.2 | 7.2 | 7.2 |
| Glucose (ca mg/ml) | 34 | 34 | 34 |
| pH | 3.2 | 3.3 | 3.2 |
| Physically stable at room temp. | 4 months | <5 days | <2 days |
| Physically stable in refrigerator | <5 days | <2 days | <2 days |

The results show that by increasing the polyethylene glycol 400 concentration from 50 to 100 mg/ml the physical stability increases at room temperature. 100 mg/ml of polyethylene glycol 400 may be an optimal concentration in this case, because, as previously shown, the physical stability decreases when the concentration is further increased. By lowering the HP-β-cyclodextrin concentration to 75 mg/ml, improved physical stability was achieved, especially at room temperature. However, it is likely that the chemical degradation of the APIs had occurred later.

As seen in table 5, 10 mg/ml levodopa and 1 mg/ml carbidopa could be physically stabilized at room temperature, by including 75 mg/ml HP-β-cyclodextrin in the formulation. However, sample 006A had a pH of 3.2 and it was decided to study if solubilization also could be achieved at higher pH. The samples in the following table were prepared and bubbled with nitrogen prior to storage.

TABLE 6

Physical stability of LD and CD with 75 mg/ml HP-β-cyclodextrin at varying pH

|  | Samples: 009 | | | | | | | | | |
| --- | --- | --- | --- | --- | --- | --- | --- | --- | --- | --- |
|  | A | B | C | D | E | F | G | H | J | K |
| Levodopa (mg/ml) | 10 | 10 | 10 | 10 | 10 | 10 | 10 | 10 | 10 | 10 |
| Carbidopa (mg/ml) | 1 | 1 | 1 | 1 | 1 | 1 | 1 | 1 | 1 | 1 |
| Sodium metabis. (mg/ml) | 1 | 1 | 1 | 1 | 1 | 1 | 1 | 1 | 1 | 1 |
| HP-β-cyclod. (mg/ml) | 75 | 75 | 75 | 75 | 75 | 75 | 75 | 75 | 75 | 75 |
| Trometamol (ca mg/ml) | 7.6 | 8.0 | 7.8 | 8.2 | 7.6 | 8.0 | 7.8 | 8.1 | 0* | 7.5 |
| Glucose (ca mg/ml) | 39 | 39 | 39 | 39 | 78 | 78 | 78 | 78 | 39 | 39 |
| pH | 3.5 | 4.7 | 3.8 | 6.2 | 3.6 | 4.6 | 3.9 | 5.1 | 3.5 | 3.5 |

TABLE 6-continued

Physical stability of LD and CD with 75 mg/ml HP-β-cyclodextrin at varying pH

| | Samples: 009 | | | | | | | | | |
|---|---|---|---|---|---|---|---|---|---|---|
| | A | B | C | D | E | F | G | H | J | K |
| Physically stable at room temp. | <3 days | <3 days | <3 days | <3 days | <3 days | <3 days | <3 days | <3 days | <3 days | <3 days |
| Physically stable in refrigerator | <3 days | <3 days | <3 days | <3 days | <3 days | <3 days | <3 days | <3 days | <3 days | <3 days |

*Sample 009J was pH-adjusted by addition of 2M NaOH instead of trometamol solution As can be seen in table 6, 75 mg/ml HP-β-cyclodextrin cannot physically stabilize 10 mg/ml levodopa and 1 mg/ml carbidopa at pH 3.5 or at a few units higher. Replacement of trometamol to NaOH did not improve stability. It is possible that nitrogen bubbling lowered the physical stability, since HP-β-cyclodextrin was an efficient stabilizer at pH 3.2 according to table 6.

Long-Term Chemical Stability of Levodopa and Carbidopa

In addition to the physical stability of the pharmaceutical solutions, the chemical stability was also determined. The decomposition of levodopa and carbidopa was determined by measuring levodopa and carbidopa concentrations, or degradation products. DHPA (3,4-dihydroxyphenylacetone) is a degradation product of carbidopa is formed in molar proportion with hydrazine, and the concentrations of DHPA were analyzed using High Pressure Liquid Chromatography (HPLC) in the present experiments.

Some samples were stored up to 4 months both at room temperature and in refrigerator for chemical analysis of levodopa and carbidopa concentrations. The following results were obtained:

TABLE 7

Chemical stability of LD and CD in various mixed samples and stock solution

| Sample, pH (storage) | Duration of storage | Starting conc. of levodopa (mg/ml) | Analysis result levodopa (mg/ml) | Starting conc. of carbidopa monohydrate (mg/ml) | Analysis result carbidopa monohydrate (mg/ml) | % decomposition, LD | % decomposition, CD |
|---|---|---|---|---|---|---|---|
| 002B, pH 3.7 (RT) | 5 days | 5.0 | 5.0 | 0.50 | 0.41 | 0.0% | 18.0% |
| 002B, pH 3.7 (fridge) | 5 days | 5.0 | 5.0 | 0.50 | 0.42 | 0.0% | 16.0% |
| 006A, pH 3.2 (RT) | 4 months | 10.0 | 10.3 | 1.0 | 0.48 | 0.0% | 52.0% |
| 001 stock solution, pH <1 (fridge) | 5 days | 50.0 | 50.4 | 5.0 | 4.98 | 0.0% | 0.4% |
| 004 stock solution, pH <1 (fridge) | 4 months | 50.0 | 50.5 | 5.0 | 5.01 | 0.0% | 0.0% |

The results show, that levodopa was stable up to 4 months after mixing at room temperature at a pH of 3.2. Carbidopa, however, had poor chemical stability, and was decomposed to 18% after 5 days at room temperature. Keeping the mixture refrigerated did not significantly slow down the decomposition. After 4 months, 52% of the carbidopa was decomposed.

The stock solution of levodopa and carbidopa with pH<1 had excellent stability in the refrigerator, with no significant decomposition at 4 months. The content of DHPA in the stock solution after 4 months was below the detection limit, thus verifying the excellent stability of carbidopa in the solution.

Two-Chamber Mixing Experiments and Short-Term Stability

In the following experiments, the concept of the invention of using one stock solution and one buffering solution is used. The solutions were produced by mixing (turning mixed solution upside-down about 15 times by hand) equal volumes of the two solutions.

Below, the solutions were a) an acidic solution of levodopa and carbidopa (pH<1) and b) a basic solution (pH approx. 9) of HP-β-cyclodextrin, glucose and trometamol, which gave a final solution of:

TABLE 8

Importance of additives and pH - trometamol as buffer component

| Substance | Conc. | Sort | Varied between conc. |
|---|---|---|---|
| Levodopa | 5 | mg/ml | 5-15 |
| Carbidopa | 1.25 | mg/ml | 1.25-3.75 |

TABLE 8-continued

Importance of additives and pH - trometamol as buffer component

| Substance | Conc. | Sort | Varied between conc. |
|---|---|---|---|
| HP-β-cyclodextrin | 75 | mg/ml | — |
| Glucose | 34 | mg/ml | — |
| Trometamol | To given pH | | — |

Variations in pH was obtained by taking different amounts of trometamol.

TABLE 9

Experiment showing protection of some substances on breakdown of LD and CD, and pH dependence

| Sample* | Additive | pH | % breakdown at 24 h | |
|---|---|---|---|---|
| | | | Levodopa | Carbidopa |
| 1286-012 A | 1.0 mg/ml EDTA | 3 | 1.4 | 16.3 |
| 1286-012 B | 10 mg/ml sodium metabisulphite | 3.1 | 0.2 | 17.1 |
| 1286-012 C | 1 mg/ml L-ascorbic acid | 3 | 1.3 | 15.9 |
| 1286-012 E | 10 mg/ml DL-cysteine | 3.1 | 1.9 | 13.4 |
| 1286-012 F | 10 mg/ml DL-methionine | 3.1 | 0.4 | 13.5 |
| 1286-012 G | 10 mg/ml L-glutathione | 3.1 | 0.8 | 12.9 |
| 1286-012 I | 10 mg/ml DL-cysteine | 3.9 | 0.8 | 12.2 |

TABLE 9-continued

Experiment showing protection of some substances on breakdown of LD and CD, and pH dependence

| Sample* | Additive | pH | % breakdown at 24 h | |
|---|---|---|---|---|
| | | | Levodopa | Carbidopa |
| 1286-012 J | 10 mg/ml DL-methionine | 3.9 | 0.0 | 10.9 |
| 1286-012 K | 10 mg/ml L-glutathione | 3.9 | 0.2 | 10.8 |

*LD and CD, 5 and 1.25 mg/ml, respectively. No light and room temperature. Levodopa and carbidopa concentrations varied as compared to table 8, however rest of components and mixing procedure were the same.

As seen in table 9, at a pH of about 3 to 3.1, the amino acids better protected carbidopa from breakdown than some common stabilizers/antioxidants. At pH 3.9 the protective action on breakdown of carbidopa from amino acids was better than at pH 3.1.

TABLE 10

Experiment showing protection of some substances on breakdown of LD and CD, and pH dependence

| Sample* | Concentration (mg/ml) | | Ratio | pH | % breakdown at 24 h | | % breakdown at 48 h | | Physical stability |
|---|---|---|---|---|---|---|---|---|---|
| | Levodopa | Carbidopa | LD/CD | | Levodopa | Carbidopa | Levodopa | Carbidopa | |
| 1286-013 A | 5 | 0.5 | 10 | 3.01 | 3.1 | 24.4 | 4.3 | 24.4 | No precipitation before 40 h |
| 1286-013 B | 5 | 1.25 | 4 | 3.06 | 1.4 | 15.6 | 0.0 | 17.8 | No precipitation before 40 h |
| 1286-013 C | 10 | 1 | 10 | 3.02 | ND | ND | ND | ND | Evident precipitation at 15 and 40 h |
| 1286-013 D | 10 | 2.5 | 4 | 3.03 | ND | ND | ND | ND | Slight precipitation at 15 h; evident at 40 h |

*No light, and room temperature

As can be read from table 10, at a pH of about 3, a lower LD/CD ratio to some degree seems to protect CD from breakdown, and from precipitation.

TABLE 11

Experiment showing breakdown of LD and CD, and pH dependence

| Sample | pH | % breakdown at 15 min | | % breakdown at 2 h | |
|---|---|---|---|---|---|
| | | Levodopa | Carbidopa | Levodopa | Carbidopa |
| 1286-014-A | 3.3 | 1.7 | 3.4 | 2.1 | 8.3 |
| 1286-014-B | 3.1 | 0.0 | 0.0 | 2.3 | 8.2 |
| 1286-014-C | 3.8 | 0.8 | 2.6 | 2.1 | 9.0 |
| 1286-014-D | 4.7 | 1.9 | 3.7 | 1.6 | 10.0 |
| 1286-014-E | 5.6 | 1.9 | 4.4 | 0.0 | 9.3 |

* LD/CD concentration 10/2.5 mg/ml. No light and room temperature.

In table 11, it is shown that there is a rapid degradation of carbidopa to 8-10% at 2 h, but only 0-3% of levodopa. There is only slight pH dependence in the breakdown of carbidopa, giving a slightly higher breakdown at higher pH.

TABLE 12

Experiment showing breakdown of LD and CD, and pH dependence

| Sample* | pH | Levodopa/ carbidopa conc. (mg/ml) | Levodopa - % breakdown at time | | | Carbidopa - % breakdown at time (min) | | | pH adjustment with |
|---|---|---|---|---|---|---|---|---|---|
| | | | 5 min | 20 min | 35 min | 5 min | 20 min | 35 min | |
| 1286-15 F | 4.9 | 10/2.5 | 0 | 0 | 0 | 0 | 0 | 2.0 | NaOH and sodium acetate |
| 1286-15 E | 5.6 | 10/2.5 | 0 | 0 | 0 | 1.2 | 2.8 | 4.8 | NaOH and sodium acetate |
| 1286-15 D | 7 | 10/2.5 | 0 | 0 | 0 | 0 | 3.2 | 3.2 | NaOH and sodium acetate |
| 1286-15 C2 | 5.5 | 15/3.75 | 0 | ND | ND | 1.1 | ND | ND | Trometamol |
| 1286-15 C1 | 7.2 | 15/3.75 | 3.6 | ND | ND | 5.9 | ND | ND | Trometamol |

*LD/CD concentration 15/3.75 and 10/2.5 mg/ml. No light and room temperature.

Results in table 12 show that breakdown of LD and CD is slightly higher at pH 5.6-7.2 than at 4.9.

TABLE 13

Experiment showing physical stability of LD and CD, and pH dependence

| Sample* | pH | Levodopa/ carbidopa conc. (mg/ml) | Physically stable at time | | | | | | pH adjustment with |
|---|---|---|---|---|---|---|---|---|---|
| | | | 5 min | 20 min | 35 min | 1 h | 2 h | 4 h | |
| 1286-15 F | 4.9 | 10/2.5 | Yes | Yes | Yes | Yes | Yes | No | NaOH and sodium acetate |
| 1286-15 E | 5.6 | 10/2.5 | Yes | Yes | Yes | Yes | No | No | NaOH and sodium acetate |
| 1286-15 D | 7 | 10/2.5 | Yes | Yes | Yes | No | No | No | NaOH and sodium acetate |
| 1286-15 C2 | 5.5 | 15/3.75 | Yes | No | No | No | No | No | Trometamol |
| 1286-15 C1 | 7.2 | 15/3.75 | Yes | No | No | No | No | No | Trometamol |

*LD/CD concentration 15/3.75 and 10/2.5 mg/ml. No light and room temperature.

Table 13 illustrates how the physical stability is lower when pH is increased from 4.9 to 7. The combination with 15 mg/ml levodopa has much lower physical stability than the 10 mg/ml combination.

Importance of Additives and pH—Citrate/Phosphate as Buffer Component

It was tested to use citrate/phosphate as buffer component instead of trometamol. Furthermore, HP-β-cyclodextrin and glucose were excluded from the composition but tested occasionally as additives. The principle for producing the mixture was the same as given above for table 8. Concentrations of DHPA, a breakdown product of carbidopa, are given as mg % of carbidopa. The following was the composition after mixing:

TABLE 14

| Substance | Conc. | Sort | Varied between conc. |
|---|---|---|---|
| Levodopa | 5 | mg/ml | 5-15 |
| Carbidopa | 1.25 | mg/ml | 1.25-3.75 |
| Sodium metabisulphite | 2.5 | mg/ml | — |
| Citrate | 110 | mM | — |
| Phosphate | 10 | mM | — |

Variations in pH were obtained by using different amounts citrate and phosphate.

TABLE 15

Experiment showing protection of some substances on breakdown of LD and CD, and stability

| Sample* | Additive | pH | % breakdown at 1 h | | DHPA, 1 h (mg %) | Physical stability at 4 h |
|---|---|---|---|---|---|---|
| | | | Levodopa | Carbidopa | | |
| 1286-019-P1 | None | 5.19 | 0.6% | 2.0% | 0.41 | Stable |

TABLE 15-continued

Experiment showing protection of some substances on breakdown of LD and CD, and stability

| Sample* | Additive | pH | % breakdown at 1 h Levodopa | % breakdown at 1 h Carbidopa | DHPA, 1 h (mg %) | Physical stability at 4 h |
|---|---|---|---|---|---|---|
| 1286-019-P2 | 150 mg/ml HP-β-cyclodextrin | 5.22 | 2.7% | 3.6% | 0.17 | Stable |
| 1286-019-P3 | 50 mg/ml glucose | 5.21 | 3.7% | 10.4% | 0.60 | Stable |
| 1286-019-P4 | 0.5 mg/ml EDTA + 2 mg/ml methionine | 5.19 | 1.2% | 2.4% | 0.46 | Stable |
| 1286-019-P5 | 0.5 mg/ml EDTA + 10 mg/ml methionine | 5.19 | 1.0% | 2.4% | 0.47 | Stable |

*LD/CD concentration 10/2.5 mg/ml. Citric acid buffer (110 mM citrate and 10 mM phosphate in final mixture). No light and room temperature.

The results summarized in tables 14 and 15 showed that addition of glucose increased carbidopa breakdown considerably, and increased levels of DHPA. HP-β-cyclodextrin gave the lowest DHPA value, but carbidopa breakdown was not much influenced. All solutions had at least 4 h of physical stability.

TABLE 16

Experiment showing protection of HP-β-cyclodextrin on breakdown of LD and CD, and physical stability

| Sample* | Additive | pH | % breakdown at 2 h Levodopa | % breakdown at 2 h Carbidopa | % breakdown at 4 h Levodopa | % breakdown at 4 h Carbidopa | % breakdown at 20 h Levodopa | % breakdown at 20 h Carbidopa | Physically stable at 20 h |
|---|---|---|---|---|---|---|---|---|---|
| 1286-019-P1 | None | 5.18 | 0.1% | 0.8% | 0.0% | 1.3% | 0.0% | 5.5% | Yes |
| 1286-019-P2 | 150 mg/ml HP-β-cyclodextrin | 5.17 | 0.1% | 0.8% | 0.0% | 0.0% | 0.0% | 2.5% | No |
| 1286-019-P7 | 75 mg/ml HP-β-cyclodextrin | 5.17 | 0.8% | 1.7% | 0.6% | 1.7% | 0.0% | 3.3% | Yes |

*LD/CD concentration 10/2.5 mg/ml. Citric acid buffer (110 mM citrate and 10 mM phosphate). No light, and room temperature.

Results summarized in table 16 show that HP-β-cyclodextrin protects carbidopa from breakdown in a concentration-dependent manner, however, the physical stability of the product is adversely affected at the highest concentration.

Levodopa showed no breakdown up to 20 h in the citrate buffer with no other additives.

Solubility Enhancers

Different tests were conducted to obtain an enhancement of the solubility of levodopa in an environment of a pH of approx. 5 and based on the citrate-phosphate buffer previously tested.

TABLE 17

Experiment showing solubility enhancement of levodopa at pH 5 depending on additives in citrate buffer

| Sample | Additive | Solubility enhancement |
|---|---|---|
| 1286-023 - 1 | 20% Kolliphor HS 15 | 0% |
| 1286-023 - 2 | 10% PEG 400 | 9% |
| 1286-023 - 3 | 5% HP-β-cyclodextrin (50 mg/ml) | 3% |
| 1286-023 - 4 | 20% Propylenglycol | 0% |
| 1286-023 - 5B | 5% Polysorbate 80 | 0% |
| 1286-023 - 6 | 2% Glycerine | 1% |
| 1286-023 - 7 | 6% Ethanol | 0% |
| 1286-023 - 8 | 10% Cremophor EL | 0% |
| 1286-023 - 9 | 5% DMSO | 9% |
| 1286-023 - 10B | 0.5% DL-methionine | 1% |
| 1286-023 - 11 | 2% L-glutathione | 7% |
| 1286-023 - 12 | 2% DL-cysteine | 5% |
| 1286-023 - 13 | 20% NMP (1-methyl-2-pyrrolidinone) | 67% |
| 1286-023 - 14 | 15% DMA (N,N-dimethylacetamide) | 40% |
| 1286-023 - 15 | Control (no additive) | — |

* Carbidopa concentration 2.5 mg/ml and excess of levodopa. Also including 2.5 mg/ml sodium metabisulphite, 100 mM citrate and 10 mM phosphate.

In table 17 it is shown that that NMP and DMA gave a significant enhancement of the solubility of levodopa. Since DMA had good solubility enhancement and a lower toxicity than NMP it was tested if DMA could be combined with other ingredients to optimize the solubility of levodopa.

TABLE 18

Experiment showing solubility enhancement of levodopa at pH 5 depending on additives and combinations, in citrate buffer

| Sample | Additive | Solubility enhancement |
|---|---|---|
| 1286-024 - 1 | None | 0% |
| 1286-024 - 2 | 4% Kollidon | 11% |
| 1286-024 - 3 | 10% Kollidon | 25% |
| 1286-024 - 4 | 10% Kollidon | 27% |
| 1286-024 - 5 | 10% Kollidon | 34% |
| 1286-024 - 6 | 8% DMA | 28% |
| 1286-024 - 7 | 8% DMA + 4% Kollidon | 34% |
| 1286-024 - 8 | 4% glutathione | 15% |
| 1286-024 - 9 | 4% glutathione + 4% Kollidon | 24% |
| 1286-024 - 10 | 4% glutathione + 8% DMA | 42% |
| 1286-024 - 11 | 4% cysteine | 5% |
| 1286-024 - 12 | 4% cysteine + 4% Kollidon | 20% |
| 1286-024 - 13 | 4% cysteine + 8% DMA | 35% |

* Carbidopa concentration 2.5 mg/ml and excess of levodopa. Also including 2.5 mg/ml sodium metabisulphite, 100 mM citrate and 10 mM phosphate.

Results summarized in table 18 show that combinations of glutathione and DMA, and cysteine and DMA, had the best solubility enhancement, followed by DMA and kollidon, and kollidon alone. Other combinations render useful solubility enhancers.

TABLE 19

Experiment showing protection of 15% DMA on physical stability

| Sample | | Levodopa (mg/ml) | pH | Temperature | Citrate buffer conc. (mM) | Physically stable at | | | |
|---|---|---|---|---|---|---|---|---|---|
| | | | | | | 7 h | 22 h | 30 h | 48 h |
| 1286-025 | A1 | 10 | 5.0 | Refrigerator | 100 | Yes | No | No | No |
| 1286-025 | B1 | 10 | 5.2 | Refrigerator | 100 | Yes | No | No | No |
| 1286-025 | C1 | 8 | 5.0 | Refrigerator | 80 | Yes | No | No | No |
| 1286-025 | D1 | 8 | 5.2 | Refrigerator | 80 | Yes | Intermediate | Intermediate | No |
| 1286-025 | A2 | 10 | 5.0 | Room | 100 | Yes | No | No | No |
| 1286-025 | B2 | 10 | 5.2 | Room | 100 | Yes | No | No | No |
| 1286-025 | C2 | 8 | 5.0 | Room | 80 | Yes | No | No | No |
| 1286-025 | D2 | 8 | 5.2 | Room | 80 | Yes | Intermediate | Intermediate | No |

*LD concentration 10 mg/ml or 8 mg/ml. Citric acid buffer 100 mM or 80 mM. No light, and refrigerator or room temperature.

Results summarized in table 19 showed that 15% DMA could give a stable 10 mg/ml LD solution for 7 h, both in refrigerator and at room temperature. When the LD concentration was lowered to 8 mg/ml and pH increased from 5.0 to 5.2 an increase in physical stability was achieved.

TABLE 20

Experiment showing osmolarity of 4% glutathione and 15% DMA, and effect on physical stability

| Sample | | pH | Levodopa (mg/ml) | Carbidopa (mg/ml) | Glutathione (%) | DMA (%) | Osmolarity (mOsm/kg) | Physical stability |
|---|---|---|---|---|---|---|---|---|
| 1286-26 | 1 | 5.3 | 10 | 2.5 | 0 | 0 | 402 | <3 h |
| 1286-26 | 2 | 4.8 | 10 | 2.5 | 4 | 8 | 1736 | <3 h |
| 1286-26 | 3 | 5.2 | 12.5 | 3.125 | 0 | 0 | 501 | <3 h |
| 1286-26 | 4 | 4.9 | 12.5 | 3.125 | 4 | 8 | 1853 | <3 h |
| 1286-26 | 5 | 4.9 | 15 | 3.75 | 4 | 8 | 2037 | <3 h |

*Citric acid buffer 100 mM. No light and room temperature.

Results summarized in table 20 show that 4% glutathione combined with 8% DMA gives a high osmolality that is further increased when levodopa and carbidopa concentrations are increased.

The solutions were physically stable for less than 3 h. Hence, although that glutathione and DMA will give solubility enhancements of levodopa and carbidopa, and possibly protection in physical stability, the increase in osmolality will most likely give adverse effects on local tolerability.

Dual Infusion Pump Experiments with On-Line Mixing

Two precision infusion pumps for human clinical use, each having a 50 ml syringe for either the stock solution or the buffer solution, had short infusion lining to a mixing connector (a Y-connector). After the Y-connector there was a single UV-protected infusion line ending in a fine pore filter, which in turn was connected to an infusion needle. The exit line after the needle was sampled. Both pumps were driven with the same speed and were started at the same time point, and both were at the start of the experiment primed quickly with 5 ml of solution at a high speed; these 5 ml were discarded. Conditions (speed of pumps, nitrogen treatment of buffer, filter pore diameter) were varied to test the operation of the system. The variable speed was given as the speed of the stock solution pump, hence the exit speed at the syringe was always twice this value. When sampling was not performed, the needle was at the outlet kept in a citrate buffer of pH 5 of approx. 200 ml. At the speed of 4 ml/h the syringes were filled again, when close to empty, after a stop of 1-5 minutes. The outlet buffer was replaced at this time. At lower speeds, no syringe change was necessary.

The composition of the stock solution was 20 mg/ml of levodopa, carbidopa in a concentration ratio LD/CD of either 4/1 or 8/1, in 200 mM HCl with a pH of approximately 1, with metabisulphite as preservatives and nitrogen to replace air. The composition of the buffering solution was 200 mM citrate and 20 mM phosphate, with a pH of approx. 7.6. The resulting pH at the needle outlet was approx. 5.2. The buffer solution was tested both with and without bubbling with nitrogen. The decomposition of levodopa and carbidopa was determined by measuring levodopa and carbidopa concentrations, or degradation products. DHPA (3,4-dihydroxyphenylacetone) is a degradation product of carbidopa is formed in molar proportion with hydrazine, and the concentrations of DHPA were analyzed using High Pressure Liquid Chromatography (HPLC) in the present experiments.

TABLE 22

Preliminary patient trials showing Levodopa bioavailability of on-line mixing for extended time in comparison to intestinal administration

| Bioavailability (Levodopa) | Patients (n) | Average % | Min % | Max % |
|---|---|---|---|---|
| SC | 3 | 101.9 | 98.0 | 106.7 |
| LCIG* | 3 | 77.7 | 69.5 | 86.8 |

*Intestinal administration of Duodopa.

Preliminary patient trials were used to demonstrate the bioavailability of levodopa and carbidopa using continues subcutaneous infusion (table 22). The trial results are from 3 randomly selected patients of a larger study, and for each patient subcutaneous, intravenous injection and intestinal administration was compared.

TABLE 21

Experiments showing that on-line mixing could be performed for extended time, under various conditions, with low breakdown of LD and CD

| Sample ** | Ratio LD/CD | API pump rate (ml/h) | Duration of test (h) | Nitrogen protection of buffer | Filter pore diameter | Mean % decomposition of API during test* | | Net mg % DHPA |
|---|---|---|---|---|---|---|---|---|
| | | | | | | Levodopa | Carbidopa | |
| 1286-055A | 4/1 | 4 | 16 | Yes | 1.2 µM | 0.0 | 0.6 | 0.7 |
| 1286-060A | 4/1 | 4 | 16 | Yes | 1.2 µM | 0.1 | 2.4 | 0.4 |
| 1286-061A | 8/1 | 4 | 16 | Yes | 1.2 µM | 1.3 | 0.8 | 0.0 |
| 1286-066A | 8/1 | 4 | 22 | No | 0.2 µM | 0 | 4.1 | 0.6 |
| 1286-066B | 8/1 | 2.5 | 22 | No | 0.2 µM | 0 | 0.7 | 0.5 |
| 1286-066C | 8/1 | 2.5 | 22 | Yes | 0.2 µM | 0 | 3.1 | 0.7 |
| 1286-068A | 8/1 | 4 | 22 | Yes | 1.2 µM | 0.8 | 1.6 | 0.6 |
| 1286-069A | 4/1 | 4 | 22 | No | 1.2 µM | 0 | 0 | 0.5 |
| 1286-071A | 8/1 | 2 | 22 | No | 1.2 µM | 1.1 | 3.4 | 0.9 |
| 1286-071C | 8/1 | 2 | 22 | No | 0.2 µM | 0 | 2.4 | 1.3 |
| 1286-072B | 8/1 | 1.4 | 32 | No | 1.2 µM | 0 | 1.2 | 1.6 |
| 1286-072C | 8/1 | 1.4 | 32 | No | 0.2 µM | 0 | 0 | 1.5 |

*Due to variations in the analytical method, values could sometimes be <0%; these values are given as 0 and with no decimal places
** Levodopa concentration in nitrogen protected stock solution: 20 mg/ml. Length of UV-protected lining: 150 cm. Syringe volume: 50 ml. Net mg % DHPA given with reference to carbidopa.

The results summarized in table 21 showed that both the concentration ratio of 4/1 and 8/1 of LD/CD gave acceptably low values for the decomposition of levodopa and carbidopa when the API rate of the pumps were 4 ml/h and using a 1.2 µM filter. There were also low levels of DHPA, a major breakdown product of carbidopa. The pumps could be run for typical treatment time of Parkinson's disease (or other levodopa-dependent diseases) of 16 h, or even more, covering a daily continuous treatment. In theory, nitrogen purging of buffer solution should further prevent levodopa and carbidopa breakdown, and limit DHPA forming, however, results show that this was not necessary to obtain pharmaceutically reasonable values of breakdown. Pump rates could be as low as 1.4 ml/h without any major effect on performance. Both tested filter pore diameters showed similar results, meaning that the system could be used for both I.V. (Intravenous; requiring the high capacity of removing bacteria) and S.C. (subcutaneous; requiring capacity of removing very small particles) administration.

In conclusion, the results show that therapeutic administration of levodopa and carbidopa in ratio 4/1 or 8/1 within a wide dosage range is possible with this system for up to a day or even more, being suitable for both S.C. and I.V. administration, and with pharmaceutically acceptable breakdown of APIs.

When using the preferred aqueous pharmaceutical solution (containing 10 mg/ml levodopa and 1.25 mg/ml (1:8) carbidopa) according to the invention, bioavailability of levodopa was equal to that of intravenous therapy using subcutaneous administration. Furthermore, when intestinal administration using the gel Duodopa (containing 20 mg/ml levodopa and 5 mg/ml carbidopa monohydrate) was compared in a similar manner to intravenous therapy, the bioavailability of levodopa was 77.7%, as summarized in table 22.

Detailed results are shown in FIGS. 12 and 13. FIG. 12 shows mean blood levels of (a) levodopa and (b) carbidopa monitored in the patients' blood during administration, plotted against treatment time. FIG. 13, shows mean plasma levels of (a) levodopa and (b) carbidopa monitored in the patients' plasma during administration, plotted against treatment time.

The study was a prospective, randomized, 3-period crossover, open-label multicentre trial comparing intravenous and subcutaneous infusion of the preferred aqueous pharmaceutical solution with intestinal Duodopa (LCIG) performed according to the principles of Good Clinical Practice (GCP). The trial included patients with Parkinson's disease who are on Duodopa treatment because of severe on-off manifestation when on oral levodopa. During one treatment visit, patients receive Duodopa at optimal dosage for 16 hours, during another treatment visit, the patients received an i.v. infusion of the preferred aqueous pharmaceutical solution at a concentration estimated to yield corresponding serum levels of levodopa for the same duration, and at a third treatment visit the patients received the corresponding amount of levodopa but in the form of s.c. infusion. Blood samples were drawn according to a set schedule during the treatment visits for up to 24 h.

The i.v. infusion of the preferred aqueous pharmaceutical solution was given through an indwelling catheter placed in the arm. An i.v. of the preferred aqueous pharmaceutical solution was delivered in 75% of the subject's individual pre-study dosing of Duodopa, administered as a morning rapid i.v. constant rate administration followed by continuous i.v. infusion up to 16 h. A suitable infusion needle was placed laterally on the abdomen for the s.c. infusion of the preferred aqueous pharmaceutical solution. The s.c. administration of the preferred aqueous pharmaceutical solution was delivered in the same dosage as the subject's individual pre-study dosing of Duodopa, also administered as a morning rapid s.c. constant rate administration followed by continuous s.c. infusion up to 16 h. Duodopa was supplied in cassettes containing a gel with 20 mg/mL levodopa and 5 mg/mL carbidopa monohydrate, and was administered directly to the proximal small intestine via a PEG-J tube connected to a portable infusion pump. Individually optimized dosing of Duodopa was administered as a morning rapid constant rate administration followed by continuous infusion up to 16 h.

Levodopa and carbidopa in patient's plasma was analysed by ultra-performance liquid chromatography-tandem mass spectrometry (UPLC-MS/MS) according to the principles of Good Laboratory Practice (GLP).

Another advantage to the instant disclosure, which was demonstrated in the preliminary patient trials, is the ability to personalize treatment for an individual patient. Specifically, FIGS. 14A and 14B detail the Levodopa levels in three separate patient's blood and plasma throughout the course of continuous subcutaneous and intravenous infusion. The three patients are at different stages of severity of PD, and thus, require different levels of Levodopa to reach a therapeutic effect. Due to the rapid bioavailability of Levodopa in the instant disclosure, the rate of infusion of the aqueous pharmaceutical solution can be adjusted during the course of the treatment to ensure that the patient is receiving a sufficient amount of Levodopa to benefit from the therapeutic effects. By avoiding excess levodopa administration, the on-off symptoms of treatment can be minimized or even avoided.

Furthermore, the preliminary patient trials also demonstrated enhanced bioavailability of carbidopa in comparison to the levels achieved during the intestinal administration of Duodopa (FIG. 13B). The increased absorption of carbidopa may allow for lower carbidopa concentrations to be incorporated in the aqueous pharmaceutical solution, thus, decreasing the amount of hydrazine, a harmful by-product, that is formed once the aqueous stock solution and aqueous buffering solution are mixed.

Although the present invention has been described above with reference to (a) specific embodiment(s), it is not intended to be limited to the specific form set forth herein. Rather, the invention is limited only by the accompanying claims and, other embodiments than the specific above are equally possible within the scope of these appended claims, e.g. different . . . than those described above.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc. do not preclude a plurality. Reference signs in the claims are provided merely as a clarifying example and shall not be construed as limiting the scope of the claims in any way.

REFERENCES

Buxton, L O. and Benet, L Z. "Pharmacokinetics: The dynamics of drug absorption, distribution, metabolism, and elimination." In Goodman and Gilman: The pharmacological basis of therapeutics. 2011, p. 17-39. The McGraw-Hill Companies, Inc. ISBN 978-0-07-162442-8

Pedro Chana et.al., "Gabapentin and Motor Fluctuations in Parkinson's Disease", Movement Disorders Vol. 12, No. 4, 1997, pp. 608-623.

Lambers H, Piessens S, Bloem A, Pronk H, Finkel P. "Natural skin surface pH is on average below 5, which is beneficial for its resident flora." Int J Cosmet Sci. 2006 October; 28(5):359-70.

Lewis, James L. III, "Metabolic Alkalosis." Attending Physician, Princeton Baptist Medical Center; Brookwood Medical Center, published at merckmanuals.com as of May 8, 2017 (http://www.merckmanuals.com/professional/endocrine-and-metabolic-disorders/acid-base-regulation-and-disorders/metabolic-alkalosis).

Shoulson et al., "On-off response. Clinical and biochemical correlations during oral and intravenous levodopa administration in parkinsonian patients." Neurology 1975; 25: 1144.

The invention claimed is:

1. A method of treating Parkinson's disease, comprising:
    continuously mixing a flow of a stock solution comprising levodopa, said stock solution having a pH of less than 2.8 at 25° C., and a flow of an aqueous buffering solution, said buffering solution having a pH of at least 4.0 at 25° C.;
    continuously obtaining from said mixing a continuous flow of an aqueous pharmaceutical solution comprising at least 5 mg/ml dissolved levodopa and having a pH in the range of 3.0 to 8.5; and
    continuously administering to a subject suffering from Parkinson's disease the obtained aqueous pharmaceutical solution within 2 hours of mixing the aqueous stock solution and the aqueous buffering solution.

2. The method of claim 1, wherein the aqueous pharmaceutical solution further comprises at least one enzyme inhibitor selected from the group consisting of dopa decarboxylase (DDC) inhibitors, catechol-o-methyltransferase (COMT) inhibitors and monoamino oxidase (MAO-B) inhibitors.

3. The method of claim 2, wherein the at least one enzyme inhibitor is:
    a dopa decarboxylase (DDC) inhibitor selected from the group consisting of carbidopa, benserazide, methyldopa, and alpha-difluoromethyl-DOPA (DFMD);
    a catechol-o-methyltransferase (COMT) inhibitor selected from the group consisting of entacapone, tolcapone, and nitecapone;

a monoamino oxidase (MAO-B) inhibitor selected from the group consisting of Rasagiline, Selegiline and Safinamide; or a combination of two or more thereof.

4. The method of claim 1, wherein the solution is a pharmaceutical infusion or injection solution.

5. The method of claim 1, wherein the solution is parenterally administered.

6. The method of claim 5, wherein the parenteral administration is subcutaneous, percutaneous, intravenous, intra-arterial, intraosseous, intra-muscular, intracerebral, intracerebroventricular, or intrathecal, the administration mode being injection or infusion.

7. The method of claim 1, wherein the aqueous pharmaceutical solution is administered within 10 minutes of mixing the aqueous stock solution and the aqueous buffering solution.

8. The method of claim 1, wherein the aqueous pharmaceutical solution has a pH of 3.5 to 8.0.

9. The method of claim 1, wherein the aqueous stock solution comprises at least 10 mg/ml levodopa.

10. The method of claim 1, wherein the aqueous stock solution has a pH of less than 2.0.

11. The method of claim 1, wherein the aqueous stock solution comprises at least one physiologically acceptable acid.

12. The method of claim 11, wherein the physiologically acceptable acid comprises a mineral acid.

13. The method of claim 12, wherein the mineral acid comprises hydrochloric acid (HCl) and the aqueous stock solution comprises at least 30 mM HCl.

14. The method of claim 11, wherein the physiologically acceptable acid comprises acetic acid.

15. The method of claim 1, wherein the aqueous stock solution further comprises at least one stabilizer.

16. The method of claim 1, wherein the method further comprises a step of de-airing the stock solution before being mixed with the aqueous buffering solution.

17. The method of claim 1, wherein the aqueous buffering solution has a pH of 4.0 to 12.

18. The method of claim 1, wherein the aqueous buffering solution comprises at least one buffer component having at least one pKa value in the range of 3 to 9.

19. The method of claim 18, wherein the buffer component comprises citric acid, or citric acid and phosphate, or trometamol (tris(hydroxymethyl) aminomethane).

20. The method of claim 18, wherein the buffer component comprises adipic acid, boric acid, calcium carbonate, calcium lactate, calcium phosphate, diethanolamine, glycine, maleic acid, meglumine, methionine, monosodium glutamate, potassium citrate, sodium acetate, sodium bicarbonate, sodium, sodium carbonate, sodium citrate dihydrate, sodium lactate, sodium phosphate dibasic, sodium phosphate monobasic, or a mixture of two or more thereof.

21. The method of claim 1, wherein the aqueous buffering solution further comprises at least one solubilizer.

22. The method of claim 21, wherein the solubilizer comprises glutathione, cysteine, HP-beta-cyclodextrin, N-methyl pyrrolidinone (NMP), dimethylacetamide (DMA), collidone, kolliphor HS 15, PEG 400, propylenglycol, polysorbate 80, glycerine, ethanol, cremophor EL, DMSO, methionine, EDTA, ascorbic acid, aspartic acid, benzalkonium chloride, benzyl benzoate, cetylpyridinium chloride, hydroxypropyl betadex, lecithin, macrogol 15 hydroxystearate, meglumine, phospholipids, poloxamer, polyoxyethylene alkyl ethers, polyoxyethylene castor oil derivative, polyoxyethylene sorbitan fatty acid esters, pyrrolidone, triolein, vitamin E polyethylene glycol succinate, or a mixture of two or more thereof.

23. The method of claim 1, wherein the aqueous buffering solution further comprises at least one stabilizer selected from the group consisting of stabilizing agents, antioxidants, preservatives, and a combination of two or more thereof.

24. The method of claim 1, wherein the pharmaceutical solution does not comprise glucose.

25. The method of claim 23, wherein the stabilizing agent comprises bentonite, calcium alginate, calcium stearate, carboxymethyl cellulose calcium, ceratonia, cyclodextrins, dextran, diethanolamine, ethylene glycol palmitostearate, fructose, glyceryl monostearate, lecithin, macrogol 15 hydroxystearate, mannitol, monoethanolamine, propylene glycol, sodium acetate, sodium borate, sorbitol, sulfobutylether beta-cyclodextrin, trehalose, or zinc acetate.

26. The method of claim 23, wherein the antioxidant is selected from the group consisting of alpha tocopherol, ascorbic acid, ascorbyl palmitate, butylated hydroxyanisole, citric acid monohydrate, erythorbic acid, malic acid, methionine, monothioglycerol, pentetic acid, potassium metabisulfite, propionic acid, sodium formaldehyde sulfoxylate, sodium metabisulfite, sodium sulfite, and sodium thiosulfate.

27. The method of claim 23, wherein the preservative is selected from the group consisting of benzalkonium chloride, benzethonium chloride, benzoic acid, boric acid, bronopol, butylene glycol, calcium acetate, calcium lactate pentahydrate, cetrimide, cetylpyridinium chloride, chlorobutanol, chlorocresol, citric acid monohydrate, cresol, edetic acid, ethyl parahydroxybenzoate, glycerol, imidurea, methyl parahydroxybenzoate, monothioglycerol, phenol, phenoxyethanol, and phenylethyl alcohol.

28. The method claim 1, wherein the aqueous pharmaceutical solution is supersaturated with levodopa.

29. An aqueous pharmaceutical solution, comprising
at least 5 mg/ml dissolved levodopa and having a pH in the range of 3.0 to 8.5, wherein said solution is formed by combining and continually mixing:
a) an aqueous stock solution comprising levodopa and having a pH of less than 2.8 at 25° C., and
b) an aqueous buffering solution for increasing the pH of said stock solution, comprising at least one buffer component, said buffering solution having a pH of at least 4.0 at 25° C.,
wherein the mixture is free of precipitated levodopa and/or wherein less than 15 wt % of levodopa has degraded over a period of 2 hours after the stock solution and the buffering solution are combined.

30. A kit for providing an aqueous pharmaceutical solution, comprising at least 5 mg/ml dissolved levodopa and having a pH in the range of 3.0 to 8.5, said kit comprising:
a) an aqueous stock solution comprising levodopa and having a pH of less than 2.8 at 25° C.,
b) an aqueous buffering solution for increasing the pH of said aqueous stock solution, comprising a buffer and having a pH of at least 4.0 at 25° C.;
c) mixing means for mixing said solutions a) and b); and
d) an output means for delivering a mixed solution from the mixing means of step c).

31. A kit for providing an aqueous pharmaceutical solution, comprising:
I) an aqueous stock solution having of pH of less than 2.8 at 25° C. and comprising;
a) aqua sterile,
b) levodopa,
c) at least one enzyme inhibitor, d) at least one physiologically acceptable acid, and
e) at least one a stabilizer, and II) an aqueous buffering solution having a pH of at least 4.0 at 25° C. and comprising;
f) aqua sterile,
g) at least one buffer component, and
h) at least one stabilizer and/or solubilizer.

32. A method of continuously preparing an aqueous pharmaceutical solution, the aqueous pharmaceutical solution being pharmaceutically acceptable for continuous parenteral or enteral administration, wherein the method comprises:
continuously mixing a flow of a stock solution comprising levodopa, said stock solution having a pH of less than 2.8 at 25° C., and a flow of an aqueous buffering solution, said buffering solution having a pH of at least 4.0 at 25° C., and
continuously obtaining from said mixing a continuous flow of an aqueous pharmaceutical solution comprising at least 5 mg/ml dissolved levodopa and having a pH in the range of 3.0 to 8.5.

33. The aqueous pharmaceutical solution of claim 29, wherein the aqueous pharmaceutical solution further comprises at least one enzyme inhibitor selected from the group consisting of dopa decarboxylase (DDC) inhibitors, catechol-o-methyltransferase (COMT) inhibitors and monoamino oxidase (MAO-B) inhibitors.

34. The aqueous pharmaceutical solution of claim 33, wherein said enzyme inhibitor is:
a dopa decarboxylase (DDC) inhibitor selected from the group consisting of carbidopa, benserazide, methyldopa, and alpha-difluoromethyl-DOPA (DFMD);
a catechol-o-methyltransferase (COMT) inhibitor selected from the group consisting of entacapone, tolcapone, and nitecapone;
a monoamino oxidase (MAO-B) inhibitor selected from the group consisting of Rasagiline, Selegiline and Safinamide; or
a combination thereof.

35. The aqueous pharmaceutical solution of claim 29, wherein the aqueous pharmaceutical solution has a pH of 4.0 to 7.5.

36. The aqueous pharmaceutical solution of claim 29, wherein the aqueous stock solution comprises at least 10 mg/ml levodopa.

37. The aqueous pharmaceutical solution of claim 29, wherein the aqueous stock solution has a pH of less than 2.0.

38. The aqueous pharmaceutical solution of claim 29, wherein the aqueous stock solution comprises at least one physiologically acceptable acid.

39. The aqueous pharmaceutical solution of claim 38, wherein the physiologically acceptable acid comprises a mineral acid.

40. The aqueous pharmaceutical solution of claim 39, wherein the mineral acid comprises hydrochloric acid (HCl) and the aqueous stock solution comprises at least 30 mM HCl.

41. The aqueous pharmaceutical solution of claim 38, wherein the physiologically acceptable acid comprises acetic acid.

42. The aqueous pharmaceutical solution of claim 29, wherein the aqueous buffering solution has a pH of 4.0 to 12.

43. The aqueous pharmaceutical solution of claim 29, wherein the aqueous buffering solution comprises at least one buffer component having at least one pKa value in the range of 3 to 9.

44. The aqueous pharmaceutical solution of claim 43, wherein the buffer component comprises citric acid, or citric acid and phosphate, or trometamol (tris(hydroxymethyl) aminomethane).

45. The aqueous pharmaceutical solution of claim 43, wherein the buffer component comprises adipic acid, boric acid, calcium carbonate, calcium lactate, calcium phosphate, diethanolamine, glycine, maleic acid, meglumine, methionine, monosodium glutamate, potassium citrate, sodium acetate, sodium bicarbonate, sodium, sodium carbonate, sodium citrate dihydrate, sodium lactate, sodium phosphate dibasic, sodium phosphate monobasic, or a mixture of two or more thereof.

46. The aqueous pharmaceutical solution of claim 29, wherein the pharmaceutical solution does not comprise glucose.

47. The method of claim 32, wherein the aqueous pharmaceutical solution further comprises at least one enzyme inhibitor selected from the group consisting of dopa decarboxylase (DDC) inhibitors, catechol-o-methyltransferase (COMT) inhibitors and monoamino oxidase (MAO-B) inhibitors.

48. The method of claim 47, wherein said enzyme inhibitor is:
a dopa decarboxylase (DDC) inhibitor selected from the group consisting of carbidopa, benserazide, methyldopa, and alpha-difluoromethyl-DOPA (DFMD);
a catechol-o-methyltransferase (COMT) inhibitor selected from the group consisting of entacapone, tolcapone, and nitecapone;
a monoamino oxidase (MAO-B) inhibitor selected from the group consisting of Rasagiline, Selegiline and Safinamide; or
a combination thereof.

49. The method of claim 32, wherein the aqueous pharmaceutical solution has a pH of 4.0 to 7.5.

50. The method of claim 32, wherein the aqueous stock solution comprises at least 10 mg/ml levodopa.

51. The method of claim 32, wherein the aqueous stock solution has a pH of less than 2.0.

52. The method of claim 32, wherein the aqueous stock solution comprises at least one physiologically acceptable acid.

53. The method of claim 52, wherein the physiologically acceptable acid comprises a mineral acid.

54. The method of claim 53, wherein the mineral acid comprises hydrochloric acid (HCl) and the aqueous stock solution comprises at least 30 mM HCl.

55. The method of claim 52, wherein the physiologically acceptable acid comprises acetic acid.

56. The method of claim 32, wherein the aqueous buffering solution has a pH of 4.0 to 12.

57. The method of claim 32, wherein the aqueous buffering solution comprises at least one buffer component having at least one pKa value in the range of 3 to 9.

58. The method of claim 57, wherein the buffer component comprises citric acid, or citric acid and phosphate, or trometamol (tris(hydroxymethyl) aminomethane).

59. The method of claim 57, wherein the buffer component comprises adipic acid, boric acid, calcium carbonate, calcium lactate, calcium phosphate, diethanolamine, glycine, maleic acid, meglumine, methionine, monosodium glutamate, potassium citrate, sodium acetate, sodium bicarbonate, sodium, sodium carbonate, sodium citrate dihydrate, sodium lactate, sodium phosphate dibasic, sodium phosphate monobasic, or a mixture of two or more thereof.

60. The method of claim 32, wherein the pharmaceutical solution does not comprise glucose.

61. The kit of claim 30, wherein the aqueous stock solution further comprises at least one enzyme inhibitor selected from the group consisting of dopa decarboxylase (DDC) inhibitors, catechol-o-methyltransferase (COMT) inhibitors and monoamino oxidase (MAO-B) inhibitors.

62. The kit of claim 61, wherein said enzyme inhibitor is:
a dopa decarboxylase (DDC) inhibitor selected from the group consisting of carbidopa, benserazide, methyldopa, and alpha-difluoromethyl-DOPA (DFMD);
a catechol-o-methyltransferase (COMT) inhibitor selected from the group consisting of entacapone, tolcapone, and nitecapone;
a monoamino oxidase (MAO-B) inhibitor selected from the group consisting of Rasagiline, Selegiline and Safinamide; or
a combination thereof.

63. The kit of claim 30, wherein the aqueous stock solution comprises at least 10 mg/ml levodopa.

64. The kit of claim 30, wherein the aqueous stock solution has a pH of less than 2.0.

65. The kit of claim 30, wherein the aqueous stock solution comprises at least one physiologically acceptable acid.

66. The kit of claim 65, wherein the physiologically acceptable acid comprises a mineral acid.

67. The kit of claim 66, wherein the mineral acid comprises hydrochloric acid (HCl) and the aqueous stock solution comprises at least 30 mM HCl.

68. The kit of claim 65, wherein the physiologically acceptable acid comprises acetic acid.

69. The kit of claim 30, wherein the aqueous buffering solution has a pH of 4.0 to 12.

70. The kit of claim 30, wherein the aqueous buffering solution comprises at least one buffer component having at least one pKa value in the range of 3 to 9.

71. The kit of claim 70, wherein the buffer component comprises citric acid, or citric acid and phosphate, or trometamol (tris(hydroxymethyl) aminomethane).

72. The kit of claim 70, wherein the buffer component comprises adipic acid, boric acid, calcium carbonate, calcium lactate, calcium phosphate, diethanolamine, glycine, maleic acid, meglumine, methionine, monosodium glutamate, potassium citrate, sodium acetate, sodium bicarbonate, sodium, sodium carbonate, sodium citrate dihydrate, sodium lactate, sodium phosphate dibasic, sodium phosphate monobasic, or a mixture of two or more thereof.

73. The kit of claim 30, wherein the kit does not comprise glucose.

74. The kit of claim 31, wherein the at least one enzyme inhibitor is selected from the group consisting of dopa decarboxylase (DDC) inhibitors, catechol-o-methyltransferase (COMT) inhibitors and monoamino oxidase (MAO-B) inhibitors.

75. The kit of claim 74, wherein said enzyme inhibitor is:
a dopa decarboxylase (DDC) inhibitor selected from the group consisting of carbidopa, benserazide, methyldopa, and alpha-difluoromethyl-DOPA (DFMD);
a catechol-o-methyltransferase (COMT) inhibitor selected from the group consisting of entacapone, tolcapone, and nitecapone;
a monoamino oxidase (MAO-B) inhibitor selected from the group consisting of Rasagiline, Selegiline and Safinamide; or
a combination thereof.

76. The kit of claim 31, wherein the aqueous stock solution comprises at least 10 mg/ml levodopa.

77. The kit of claim 31, wherein the aqueous stock solution has a pH of less than 2.0.

78. The kit of claim 31, wherein the physiologically acceptable acid comprises a mineral acid.

79. The kit of claim 78, wherein the mineral acid comprises hydrochloric acid (HCl) and the aqueous stock solution comprises at least 30 mM HCl.

80. The kit of claim 31, wherein the physiologically acceptable acid comprises acetic acid.

81. The kit of claim 31, wherein the aqueous buffering solution has a pH of 4.0 to 12.

82. The kit of claim 31, wherein the at least one buffer component has at least one pKa value in the range of 3 to 9.

83. The kit of claim 82, wherein the buffer component comprises citric acid, or citric acid and phosphate, or trometamol (tris(hydroxymethyl) aminomethane).

84. The kit of claim 82, wherein the buffer component comprises adipic acid, boric acid, calcium carbonate, calcium lactate, calcium phosphate, diethanolamine, glycine, maleic acid, meglumine, methionine, monosodium glutamate, potassium citrate, sodium acetate, sodium bicarbonate, sodium, sodium carbonate, sodium citrate dihydrate, sodium lactate, sodium phosphate dibasic, sodium phosphate monobasic, or a mixture of two or more thereof.

85. The kit of claim 31, wherein the kit does not comprise glucose.

* * * * *